US011471492B2

(12) United States Patent
Bloemen et al.

(10) Patent No.: US 11,471,492 B2
(45) Date of Patent: Oct. 18, 2022

(54) COMPOSITIONS FOR TREATMENT OF OSTEOCHONDRAL DISORDERS

(71) Applicant: KATHOLIEKE UNIVERSITEIT LEUVEN, Leuven (BE)

(72) Inventors: Veerle Bloemen, Brussels (BE); Johanna Bolander, Oud-Heverlee (BE); Frank Luyten, Kraainem (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 189 days.

(21) Appl. No.: 15/578,059

(22) PCT Filed: May 27, 2016

(86) PCT No.: PCT/EP2016/062078
§ 371 (c)(1),
(2) Date: Nov. 29, 2017

(87) PCT Pub. No.: WO2016/193175
PCT Pub. Date: Dec. 8, 2016

(65) Prior Publication Data
US 2018/0153940 A1 Jun. 7, 2018

(30) Foreign Application Priority Data

May 29, 2015 (GB) .................................. 1509264.6

(51) Int. Cl.
| | | |
|---|---|---|
| *A61K 35/28* | (2015.01) | |
| *C12N 5/077* | (2010.01) | |
| *C12N 5/00* | (2006.01) | |
| *A61P 19/02* | (2006.01) | |
| *A61P 19/04* | (2006.01) | |
| *A61P 19/10* | (2006.01) | |

(52) U.S. Cl.
CPC .............. *A61K 35/28* (2013.01); *A61P 19/02* (2018.01); *A61P 19/04* (2018.01); *A61P 19/10* (2018.01); *C12N 5/0012* (2013.01); *C12N 5/0037* (2013.01); *C12N 5/0654* (2013.01); *C12N 5/0655* (2013.01); *C12N 2500/25* (2013.01); *C12N 2500/33* (2013.01); *C12N 2500/38* (2013.01); *C12N 2500/46* (2013.01); *C12N 2500/98* (2013.01); *C12N 2500/99* (2013.01); *C12N 2501/155* (2013.01); *C12N 2501/37* (2013.01); *C12N 2501/39* (2013.01); *C12N 2501/395* (2013.01); *C12N 2506/1392* (2013.01); *C12N 2513/00* (2013.01); *C12N 2533/18* (2013.01); *C12N 2533/54* (2013.01); *C12N 2533/78* (2013.01)

(58) Field of Classification Search
None
See application file for complete search history.

(56) References Cited

U.S. PATENT DOCUMENTS

| | | | |
|---|---|---|---|
| 4,968,590 A | 11/1990 | Kuberasampath et al. | |
| 5,011,691 A | 4/1991 | Oppermann et al. | |
| 5,496,552 A | 3/1996 | Kuberasampath et al. | |
| 5,674,844 A | 10/1997 | Kuberasampath et al. | |
| 5,939,323 A * | 8/1999 | Valentini .............. | C12N 5/0068 424/426 |
| 6,333,312 B1 | 12/2001 | Kuberasampath et al. | |
| 2001/0039050 A1* | 11/2001 | Luyten ................. | C12N 5/0655 435/387 |
| 2010/0099190 A1* | 4/2010 | Wang ................... | C12N 5/0663 435/402 |
| 2016/0038544 A1* | 2/2016 | Keller .................... | A61P 19/10 424/93.7 |
| 2016/0264936 A1 | 9/2016 | Nakano et al. | |

FOREIGN PATENT DOCUMENTS

| | | | | |
|---|---|---|---|---|
| WO | 9859035 A2 | | 12/1998 | |
| WO | WO-9859035 A2 * | | 12/1998 | ........... C12N 5/0655 |
| WO | 2010003062 A2 | | 1/2010 | |
| WO | 2012013969 A1 | | 2/2012 | |
| WO | WO-2014015109 A1 * | | 1/2014 | ........... C12N 5/0655 |
| WO | 2015068505 A1 | | 5/2015 | |

OTHER PUBLICATIONS

Eyckmans (Species Specificity of Ectopic Bone Formation Using Periosteum-Derived Mesenchymal Progenitor Cells, 2006) (Year: 2006).*
Asahina et al., "Human Osteogenic Protein-1 Induces Chondroblastic, Osteoblastic, and/or Adipocytic Differentiation of Clonal Murine Target Cells," Experimental Cell Research, vol. 222, 1996, pp. 38-47.
Bolander et al., "The Combined Mechanism of Bone Morphogenetic Protein- and Calcium Phosphate-Induced Skeletal Tissue Formation by Human Periosteum Derived Cells," European Cells and Materials, vol. 31, 2016, pp. 11-25.
De Bari et al., "Mesenchymal Multipotency of Adult Human Periosteal Cells Demonstrated by Single-Cell Lineage Analysis," Arthritis & Rheumatism, vol. 54, No. 4, Apr. 2006, pp. 1209-1221.
Dominici et al., "Minimal Criteria for Defining Multipotent Mesenchymal Stromal Cells. The International Society for Cellualr Therapy Position Statement", Cytotherapy, vol. 8, No. 4, 2006, pp. 315-317.

(Continued)

*Primary Examiner* — Nghi V Nguyen
(74) *Attorney, Agent, or Firm* — Workman Nydegger

(57) ABSTRACT

The application provides biocompatible carriers comprising bone forming and/or cartilage forming cells and methods for making them. The application further provides pharmaceutical compositions comprising said ATMPs and method of treatments using said ATMPs. The application further relates to said ATMPS for use in the treatment of bone disorders, cartilage disorders and joint disorders. The current invention further relates to method of treatments of bone disorders, cartilage disorders and joint disorders.

20 Claims, 49 Drawing Sheets

(56) References Cited

OTHER PUBLICATIONS

Eyckmans et al., "Species Specificity of Ectopic Bone Formation Using Periosteum-Derived Mesenchymal Progenitor Cells," Tissue Engineering, vol. 12, No. 8, 2006, pp. 2203-2213.

Eyckmans et al., "A Clinically Relevant Model of Osteoinduction: A Process Requiring Calcium Phosphate and BMP/Wnt Signalling," Journal of Cellular and Molecular Medicine, vol. 14, No. 6B, 2010, pp. 1845-1856.

Great Britain Search Report from GB Application No. GB1509264.6, dated Feb. 26, 2016.

Griffith et al., "Three-Dimensional Structure of Recombinant Human Osteogenic Protein 1: Structural Paradigm for the Transforming Growth Factor β Superfamily," Proceedings of the National Academy of Sciences of the United States of America, vol. 93, Jan. 1996, pp. 878-883.

Guan et al., "Pluripotency of Spermatogonial Stem Cells From Adult Mouse Testis," Nature, vol. 440, Apr. 27, 2006, pp. 1199-1203.

Harrison, Jr et al., "Osteogenin Promotes Reexpression of Cartilage Phenotype by Dedifferentiated Articular Chondrocytes in Serum-Free Medium," Experimental Cell Research, vol. 192, 1991, pp. 340-345.

Hoffmann et al., "Perspectives in the Biological Function, the Technical and Therapeutic Application of Bone Morphogenetic Proteins," Applied Microbiology and Biotechnology, vol. 57, Aug. 7, 2001, pp. 294-308.

International Search Report from PCT Application No. PCT/EP2016/062078, dated Aug. 23, 2016.

Jones et al., "Osteogenic Protein-1 (OP-1) Expression and Processing in Chinese Hamster Ovary Cells: Isolation of a Soluble Complex Containing the Mature and Pro-Domains of OP-1," Growth Factors, vol. 11, 1994, pp. 215-225.

Kwon et al., "Modulation of BMP-2-Induced Chondrogenic Versus Osteogenic Differentiation of Human Mesenchymal Stem Cells by Cell-Specific Extracellular Matrices," Tissue Engineering: Part A, vol. 19, No. 1 & 2, 2013, pp. 49-58.

Leijten et al., "Cell Based Advanced Therapeutic Medicinal Products for Bone Repair: Keep it Simple?," Advanced Drug Delivery Reviews, vol. 84, 2015, pp. 30-44.

Ma et al., "Concise Review: Cell-Based Strategies in Bone Tissue Engineering and Regenerative Medicine," Stem Cells Translational Medicine, Dec. 3, 2013, pp. 98-107.

Neumann et al., "BMP7 Promotes Adipogenic by Not Osteo-/Chondrogenic Differentiation of Adult Human Bone Marrow-Derived Stem Cells in High-Density Micro-Mass Culture," Journal of Cellular Biochemistry, vol. 102, 2007, pp. 626-637.

Teixeira et al., "High Throughput Generated Micro-Aggregates of Chondrocytes Stimulate Cartilage Formation In Vitro and In Vivo," European Cells and Materials, vol. 23, 2012, pp. 387-399.

Okita et al., "Generation of Germline-Competent Induced Pluripotent Stem Cells," Nature, vol. 448, Jul. 19, 2007, pp. 313-318.

Reddi, "Bone Morphogenetic Proteins: From Basic Science to Clinical Applications," The Journal of Bone & Joint Surgery, vol. 83-A, Supplement 1, Part 1, 2001, pp. S1-1-S1-6.

Roberts et al., "The Combined Bone Forming Capacity of Human Periosteal Derived Cells and Calcium Phosphates," Biomaterials, vol. 32, Mar. 21, 2011, pp. 4393-4405.

Sampath et al., "Dissociative Extraction and Reconstitution of Extracellular Matrix Components Involved in Local Bone Differentiation," Proceedings of the National Academy of Sciences of the United States of America, vol. 78, No. 12, Dec. 1981, pp. 7599-7603.

Sampath et al., "Isolation of Osteogenin, an Extracellular Matrix-Associated, Bone-Inductive Protein, by Heparin Affinity Chromatography," Proceedings of the National Academy of Sciences of the United States of America, vol. 84, Oct. 1987, pp. 7109-7113.

Takahashi et al., "Induction of Pluripotent Stem Cells from Mouse Embryonic and Adult Fibroblast Cultures by Defined Factors," Cell, vol. 126, Aug. 25, 2006, pp. 663-676.

Takahashi et al., "Induction of Pluripotent Stem Cells from Adult Human Fibroblasts by Defined Factors," Cell, vol. 131, Nov. 30, 2007, pp. 861-872.

Urist et al., "Purification of Bovine Bone Morphogenetic Protein by Hydroxyapatite Chromatography," Proceedings of the National Academy of Sciences of the United States of America, vol. 81, Jan. 1984, pp. 371-375.

Urist et al., "Human Bone Morphogenetic Protein (hBMP) (41630)," Proceedings of the Society for Experimental Biology and Medicine, vol. 173, 1983, pp. 194-199.

Van Gastel et al., "Expansion of Murine Periosteal Progenitor Cells With Fibroblast Growth Factor 2 Reveals an Intrinsic Endochondral Ossification Program Mediated by Bone Morphoenetic Protein 2," Stem Cells, Jul. 3, 2014, pp. 2407-2418.

Wang et al., "Recombiant Human Bone Morphogenetic Protein Induces Bone Formation," Proceedings of the National Academy of Sciences of the United States of America, vol. 87, Mar. 1990, pp. 2220-2224.

Wilmut et al., "Viable Offspring Derived from Fetal and Adult Mammalian Cells," Nature, vol. 385, Feb. 27, 1997, pp. 810-813.

Wozney et al., "Novel Regulators of Bone Formation: Molecular Clones and Activities," Science, vol. 242, Downloaded Feb. 26, 2014, pp. 1528-1534.

Ying et al., "Changing Potency by Spontaneous Fusion," Nature, vol. 416, Apr. 4, 2002, pp. 545-548.

European Office Communication from EP Application No. 16727156.8, dated Jan. 21, 2019.

Office Action from corresponding EP Application No. 16727156.8, dated Apr. 14, 2020.

Office Action from corresponding European Application No. 16727156.8, dated Mar. 5, 2021.

Annex to the communication dated Jun. 17, 2020 for EP Application No. 16727156.

Bolander et al., "Pre-culture and BMP-2 stimulation under serum freeconditions enhances osteochondrogenic differentiation and BMP signalling in human periosteum derived", Biomaterials and Regenerative Medicine, Date: Jul. 8, 2013-Jul. 12, 2013, Location: Riva Del Garda, Italy, Jul. 1, 2013 (Jul. 1, 2013), XP055703845, Retrieved from the Internet: URL:https://lirias.kuleuven.be/1674550?1imo=0.

* cited by examiner

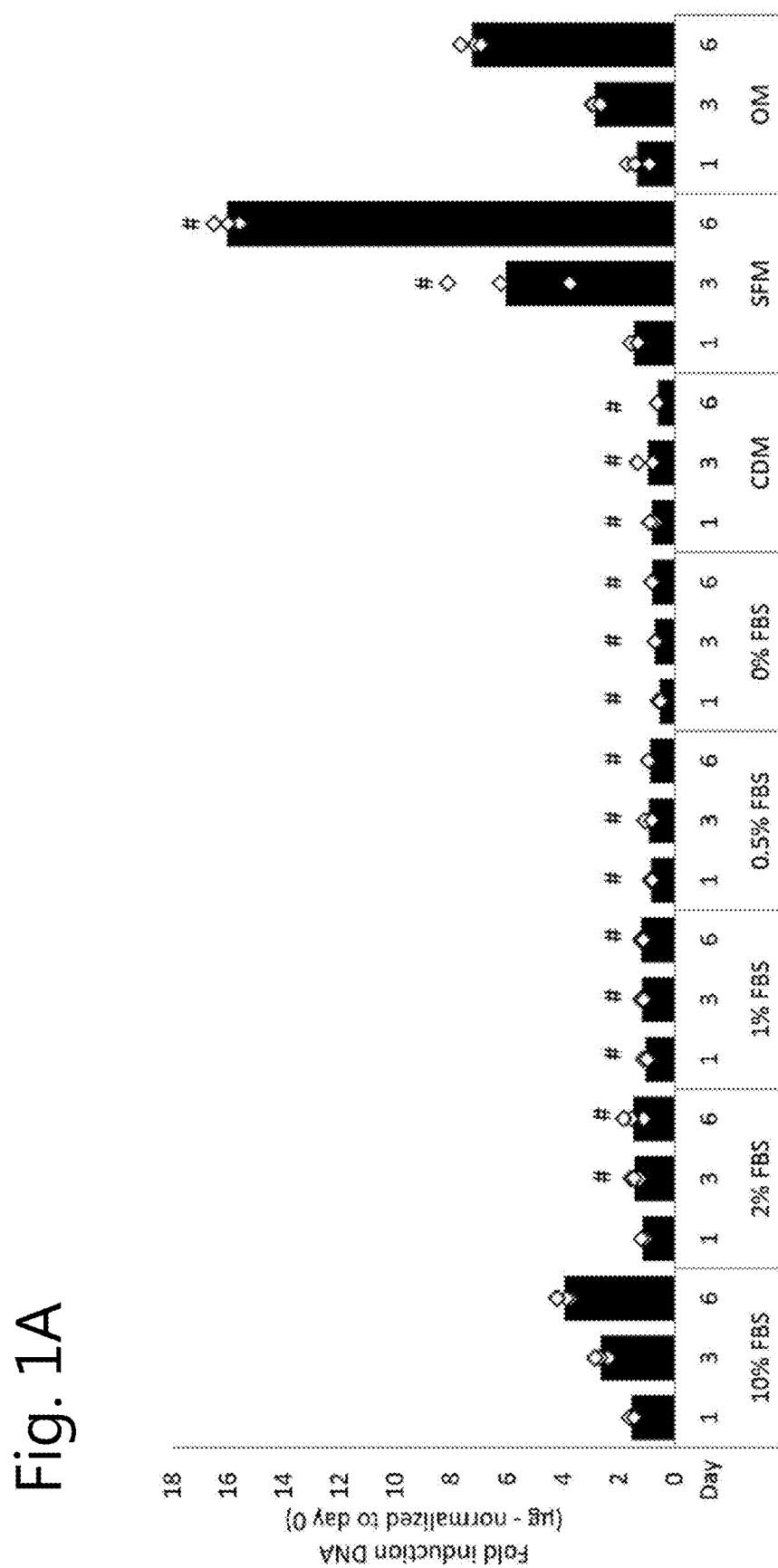

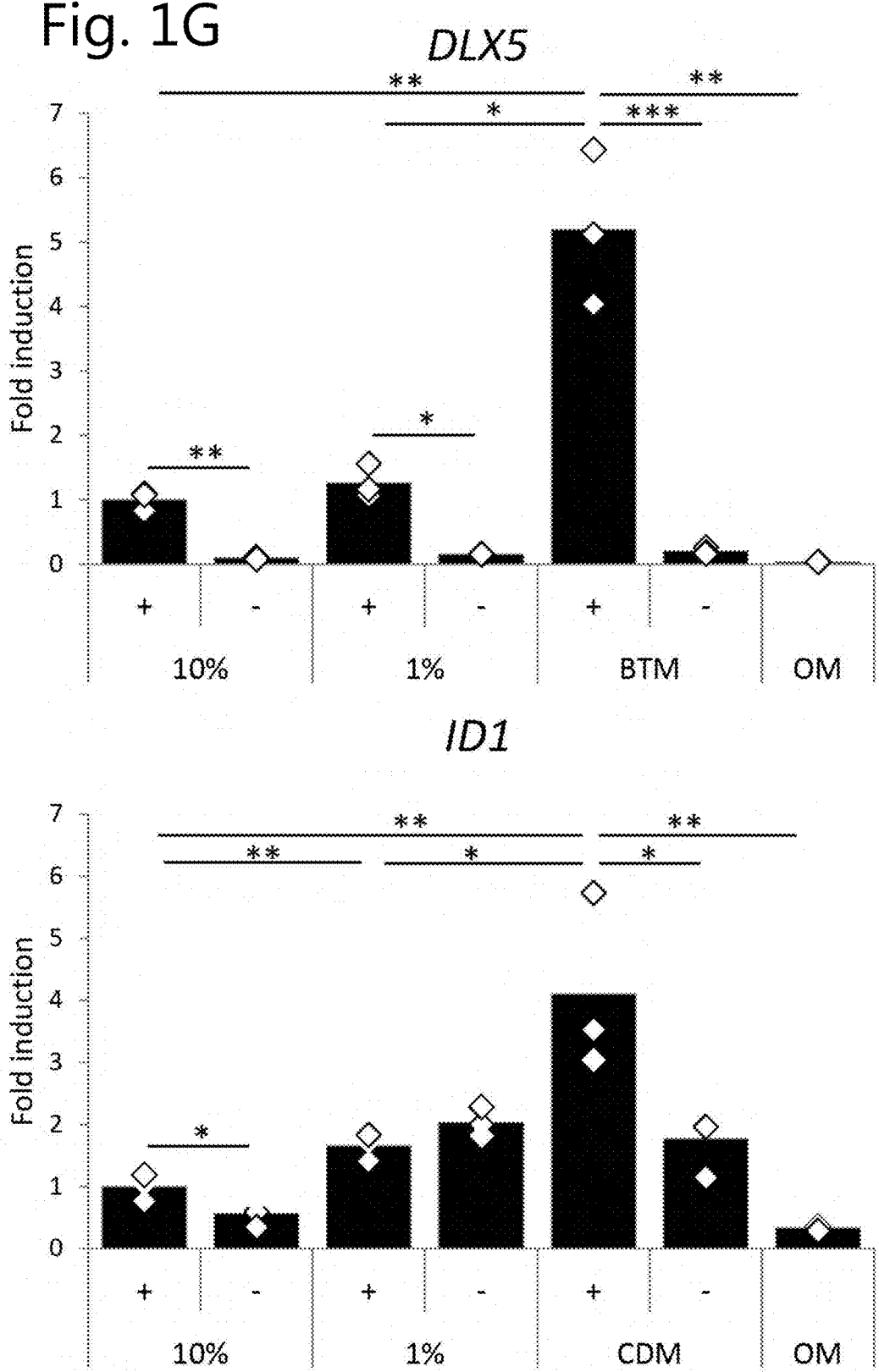

Fig. 4A(1)
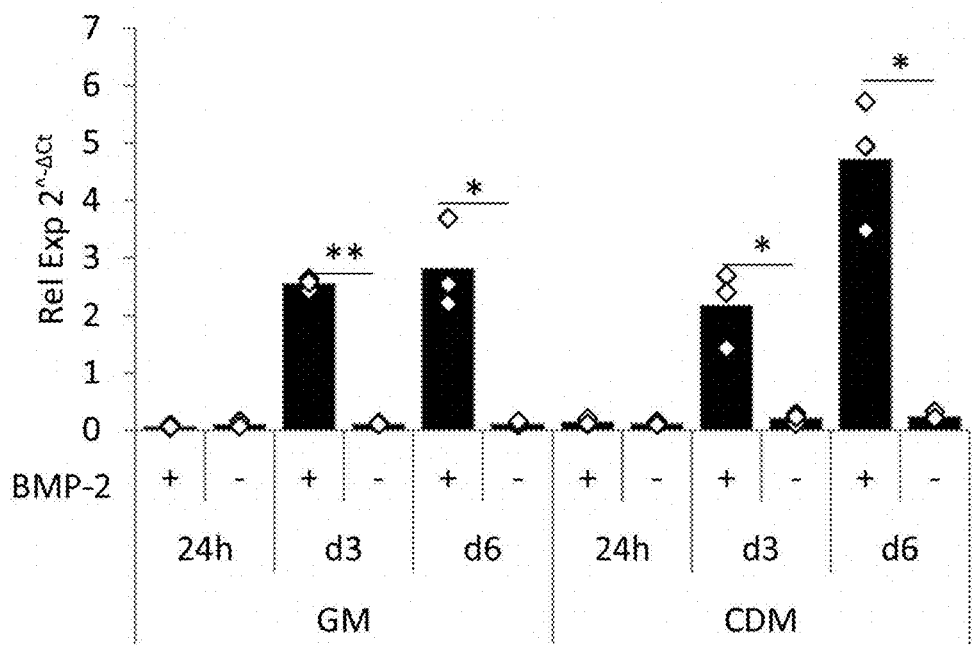
Fig. 4A(2)
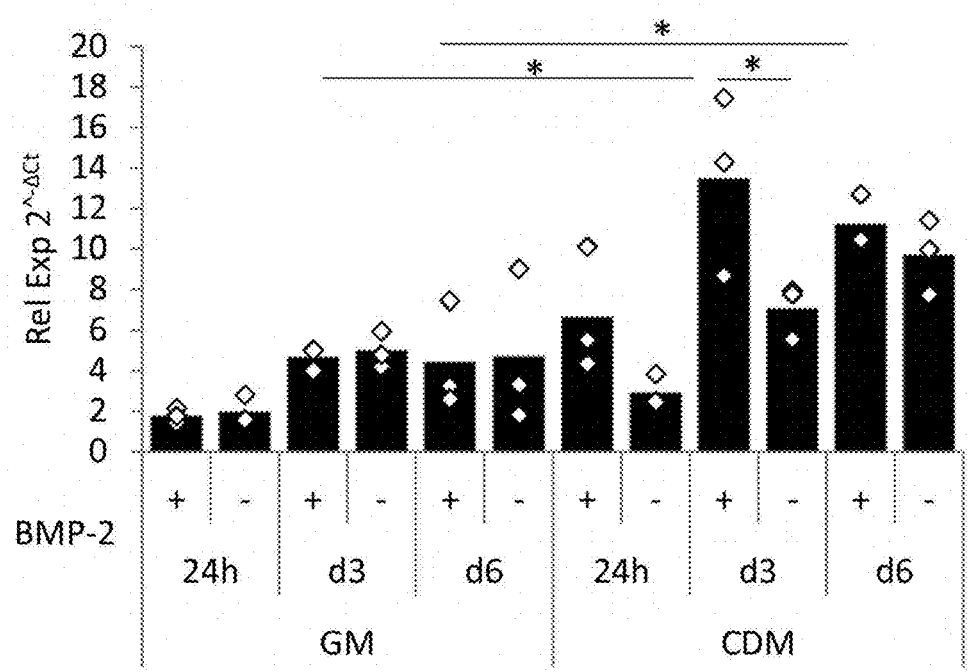

Fig. 4A(3)
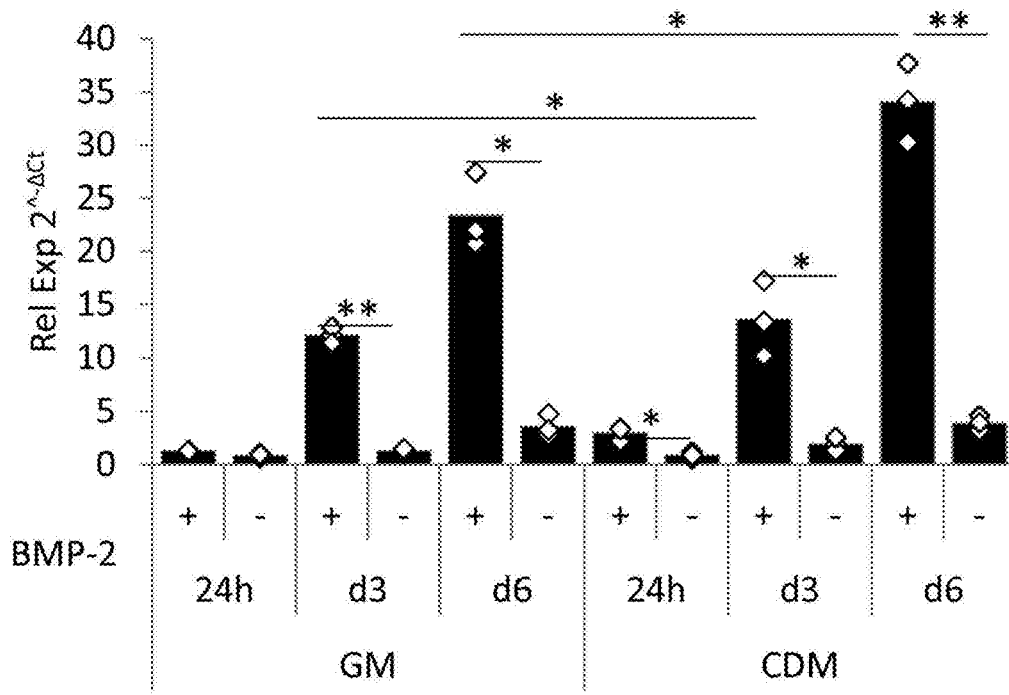
Fig. 4A(4)
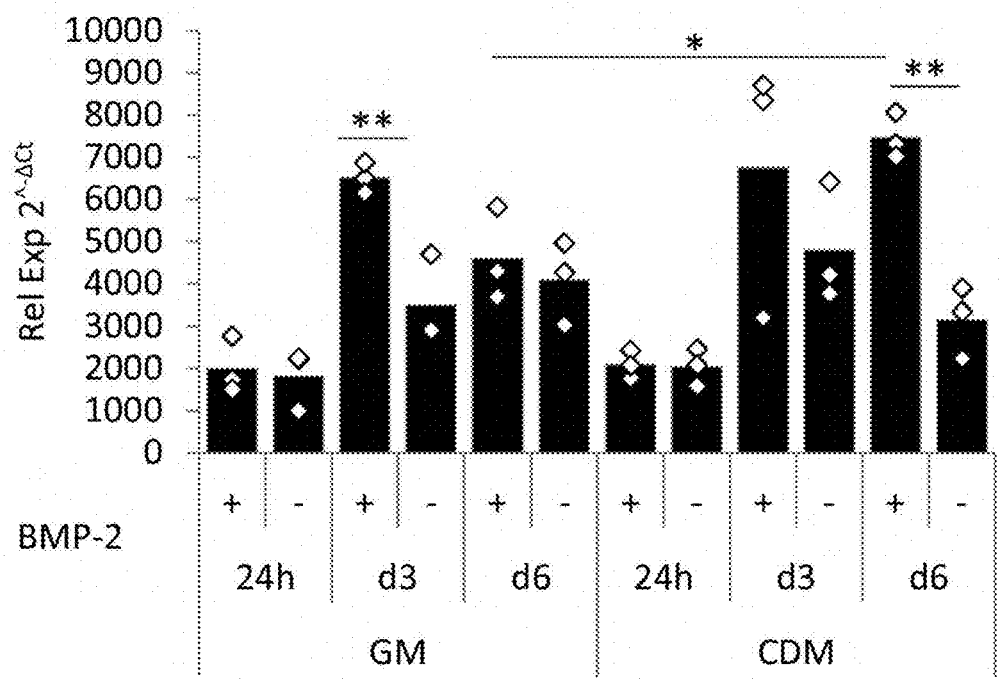

Fig. 4A(5)
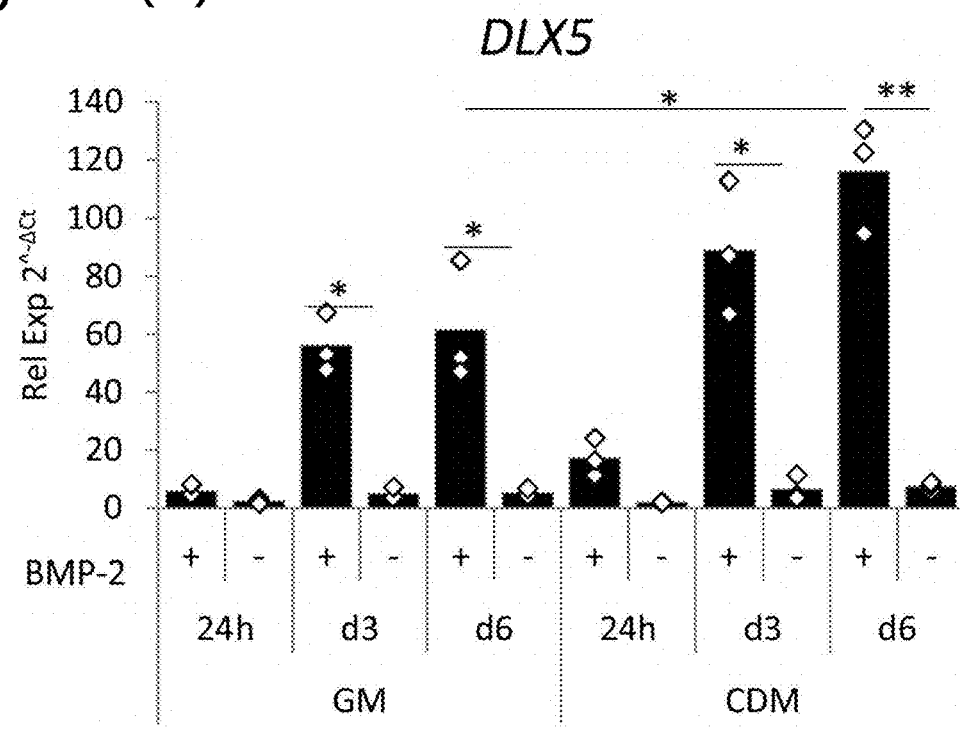
Fig. 5A
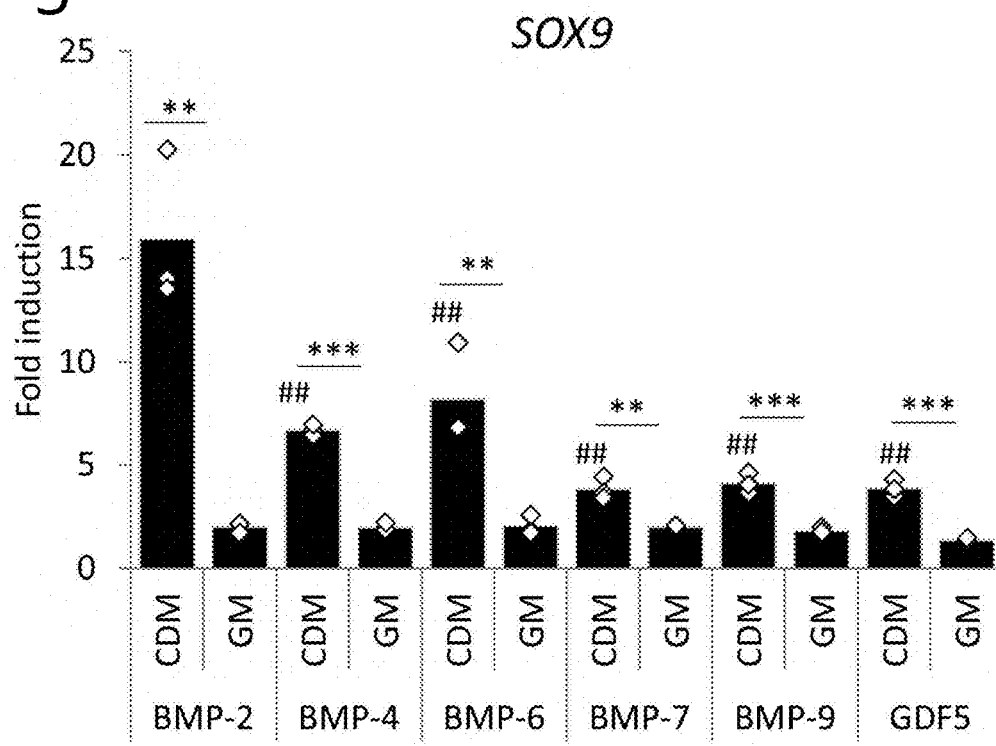

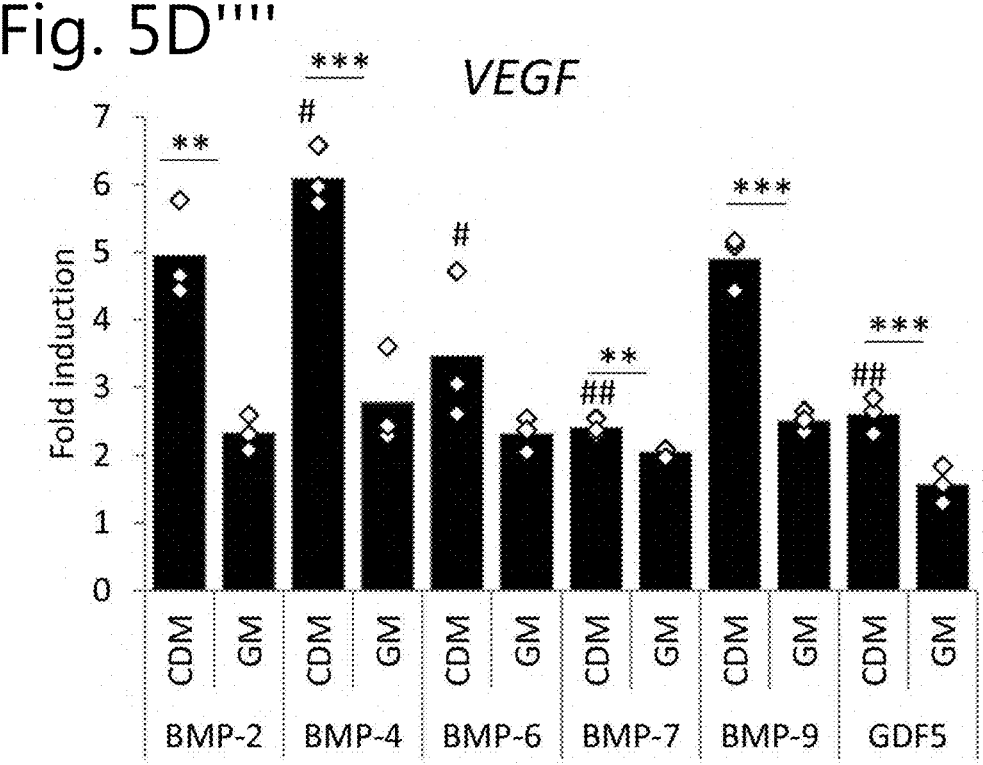
Fig. 5D""
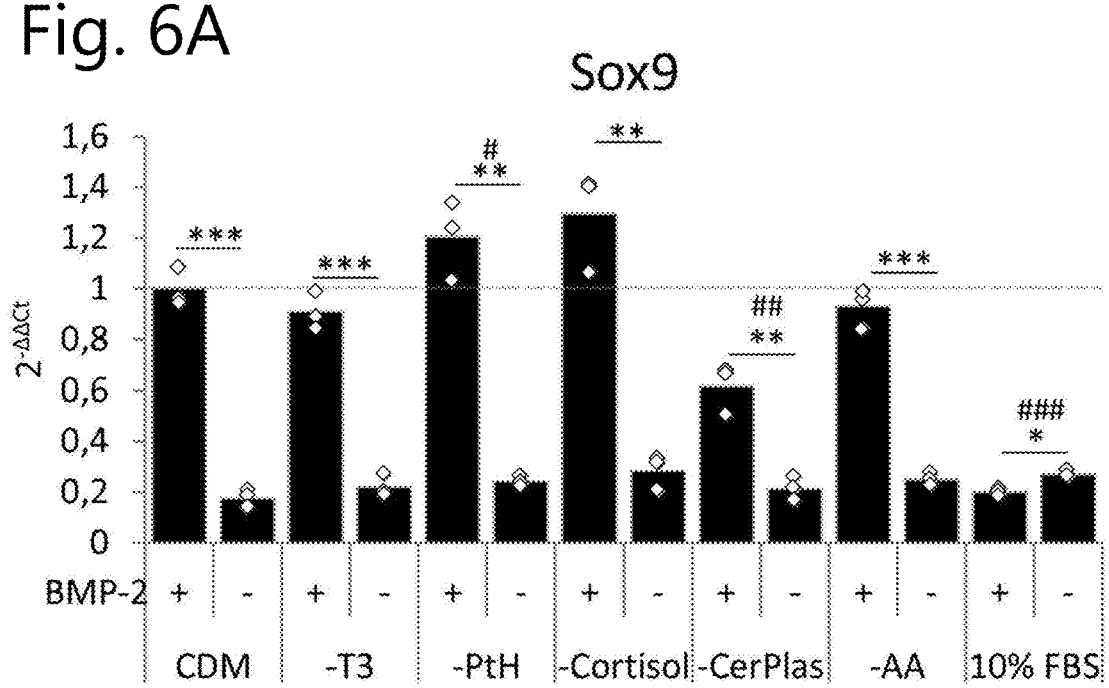
Fig. 6A

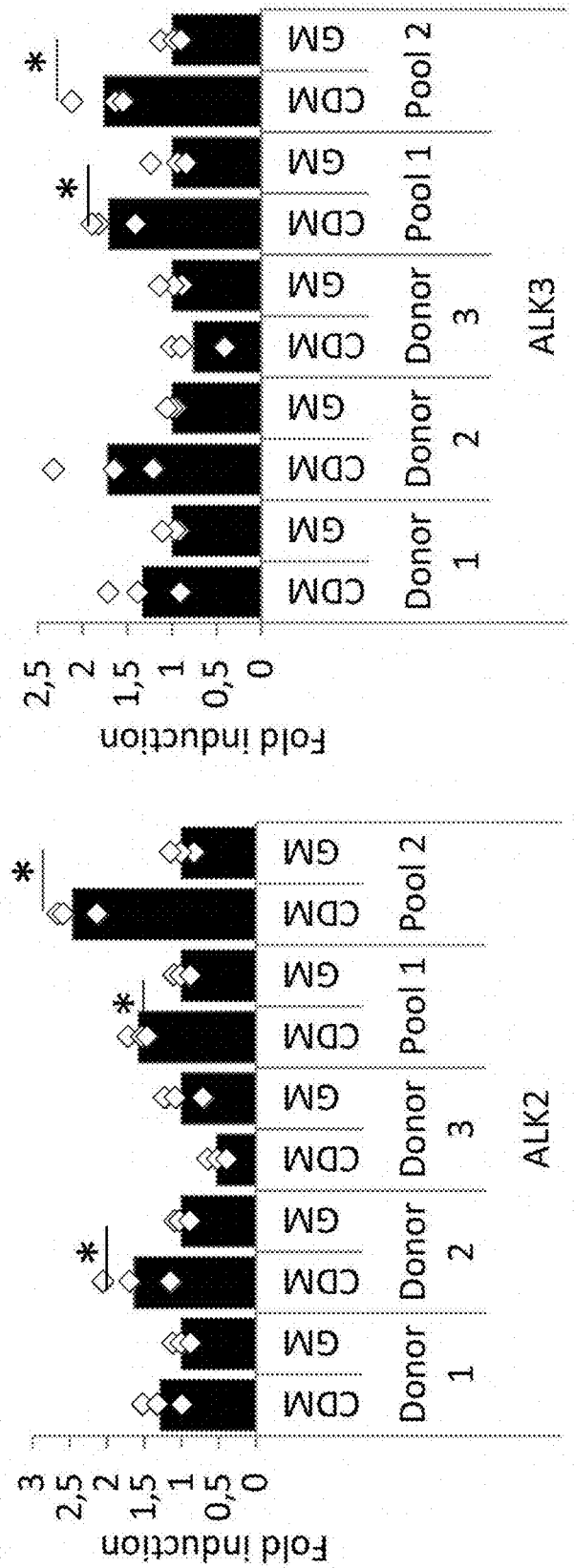
Fig. 8B(1)

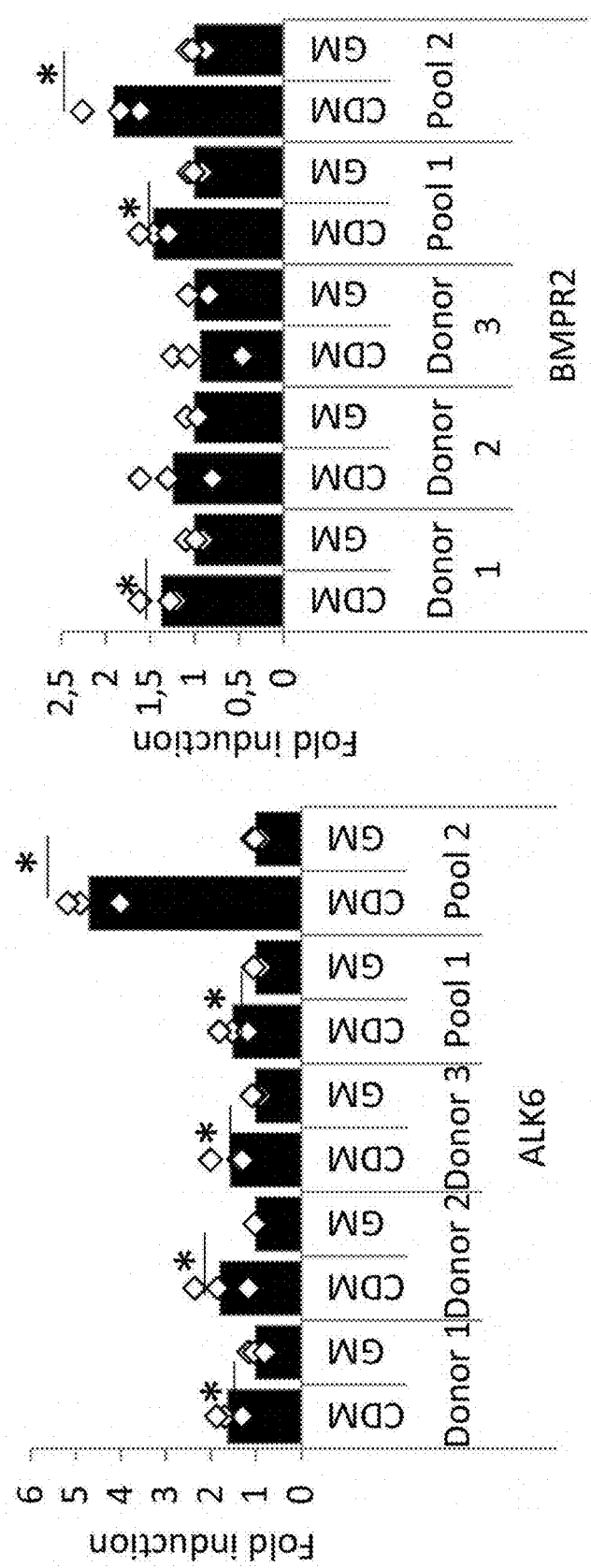

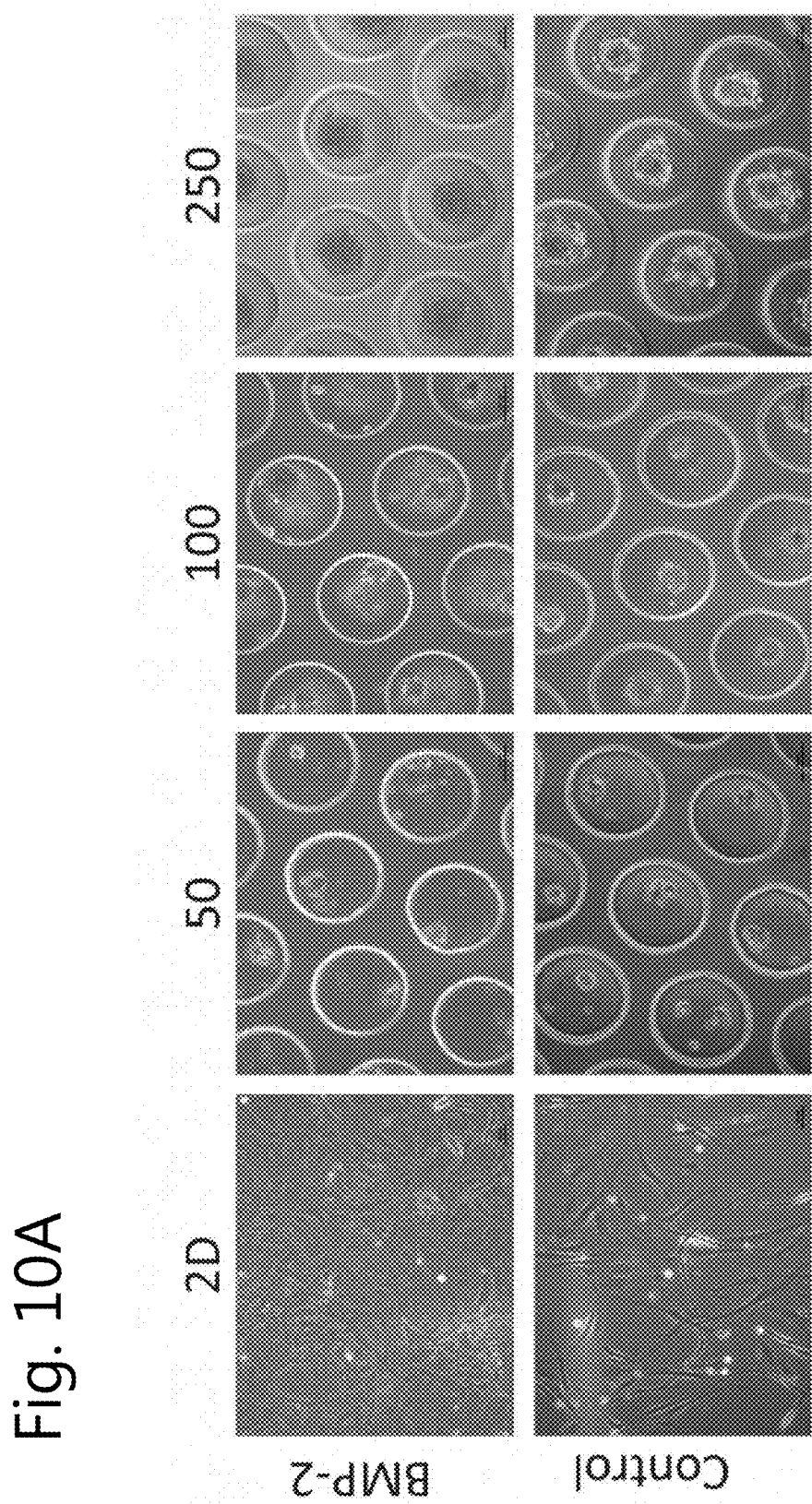

Fig. 10B
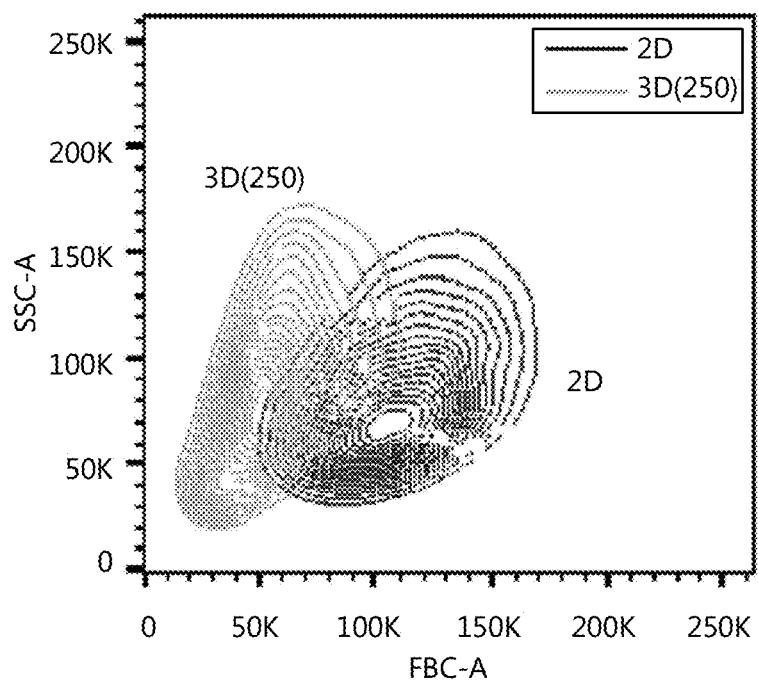
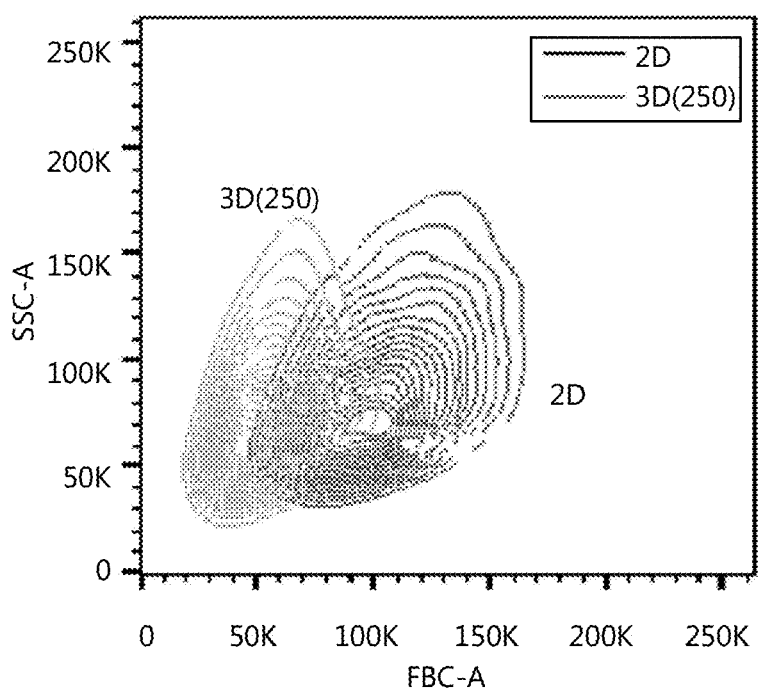

Fig. 12A(1)
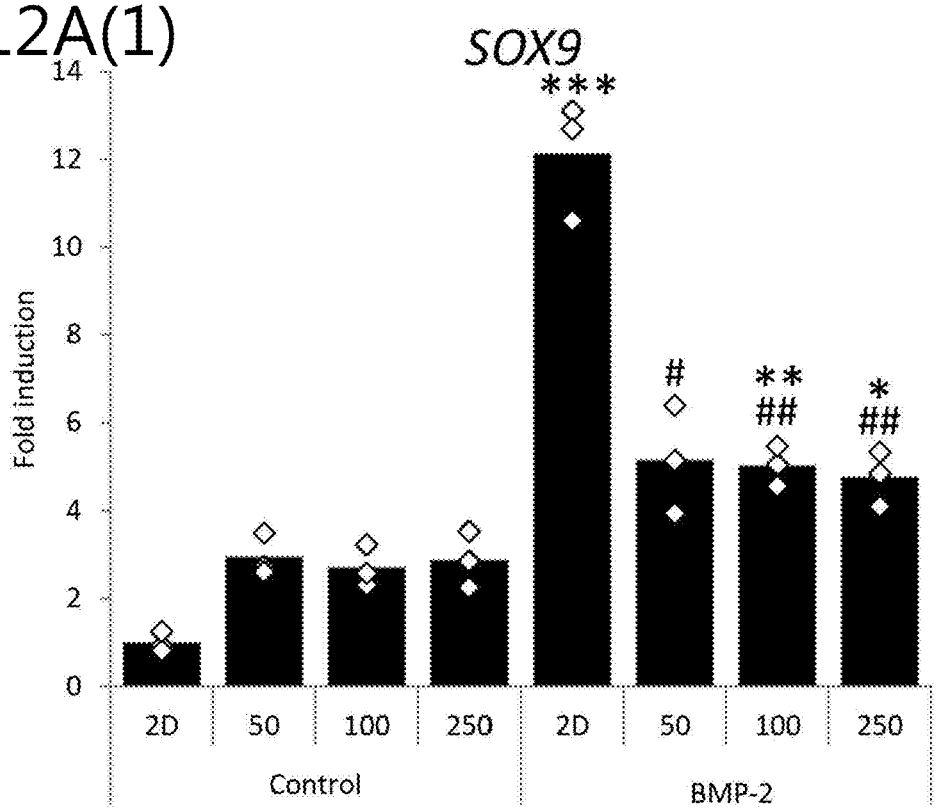
Fig. 12A(2)
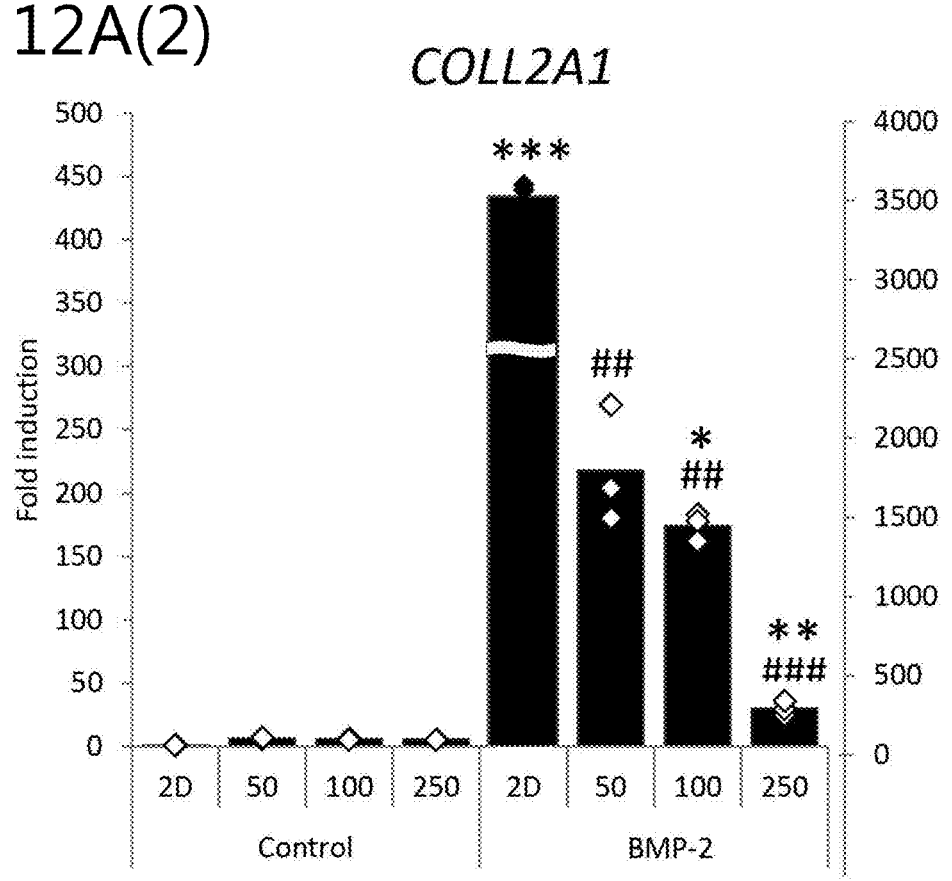

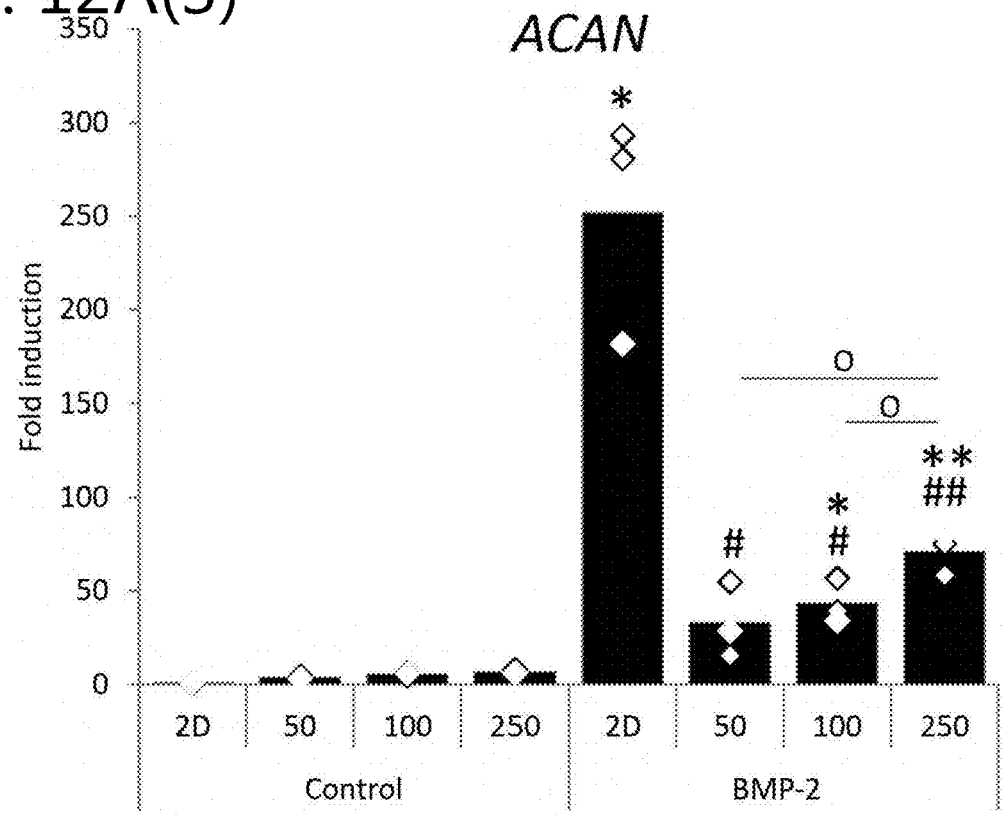
Fig. 12A(3)
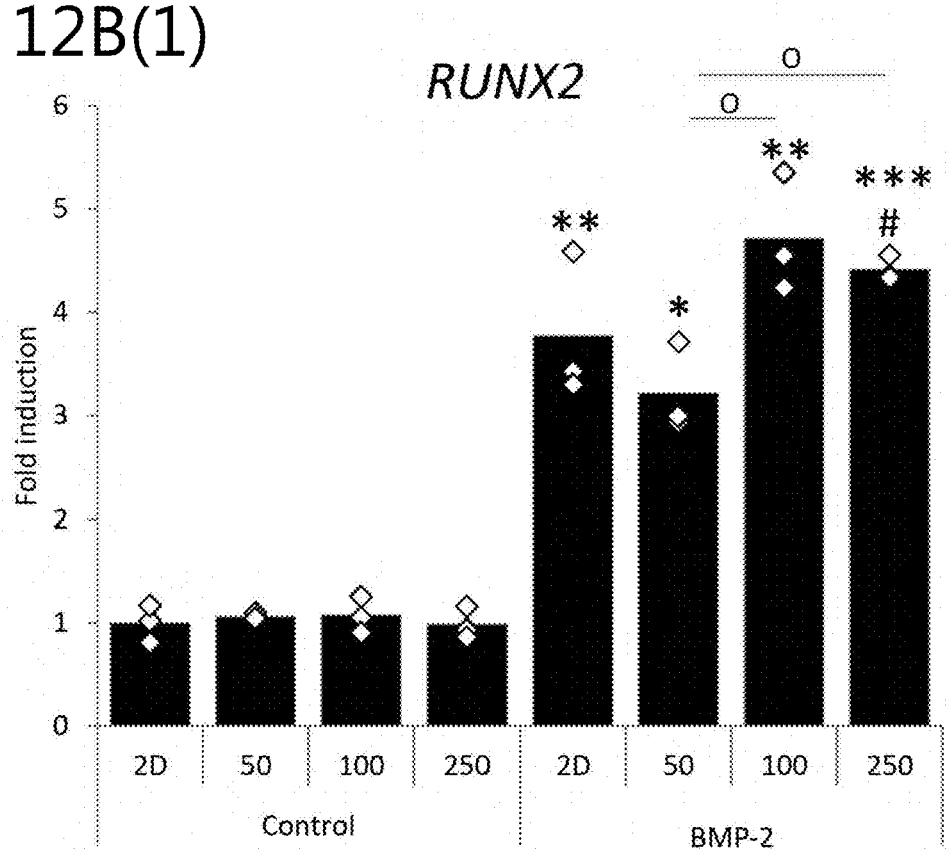
Fig. 12B(1)

Fig. 12B(2)
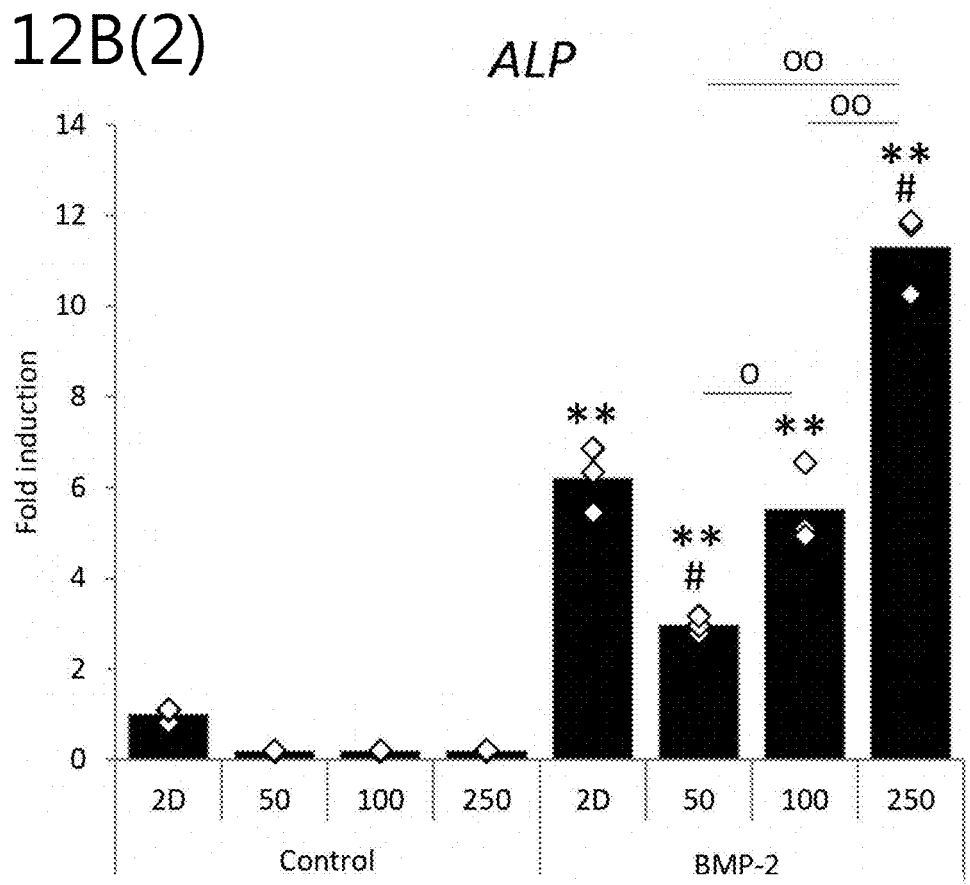
Fig. 12B(3)
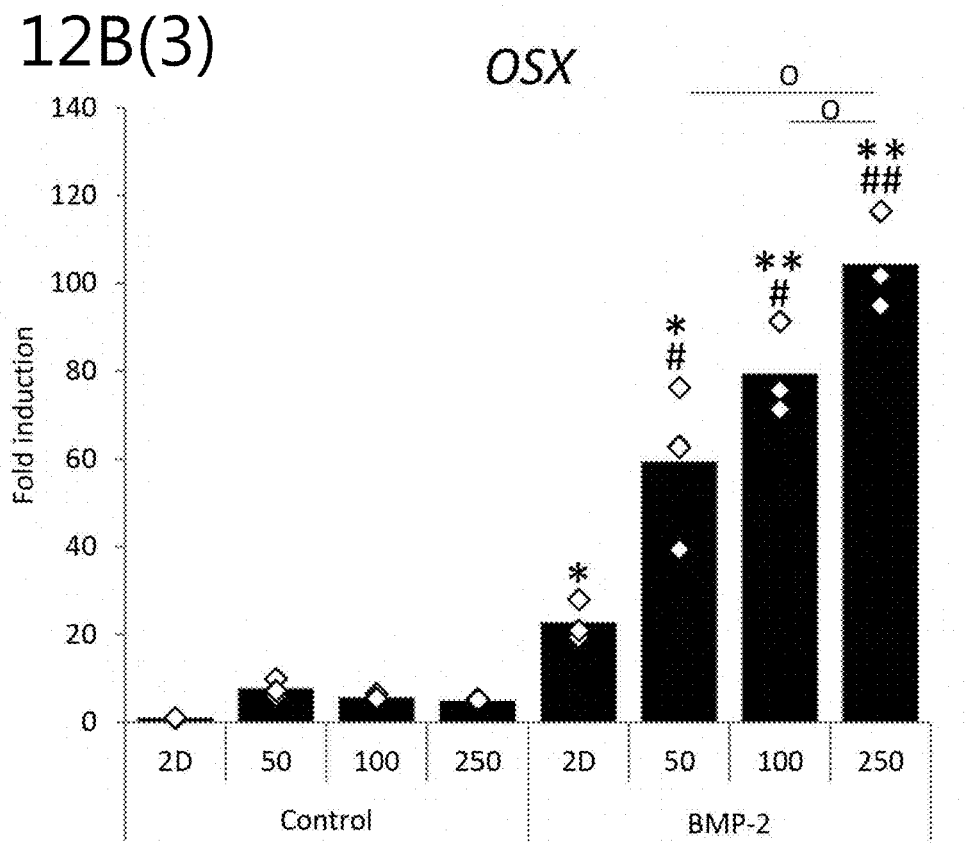

Fig. 12C(1)
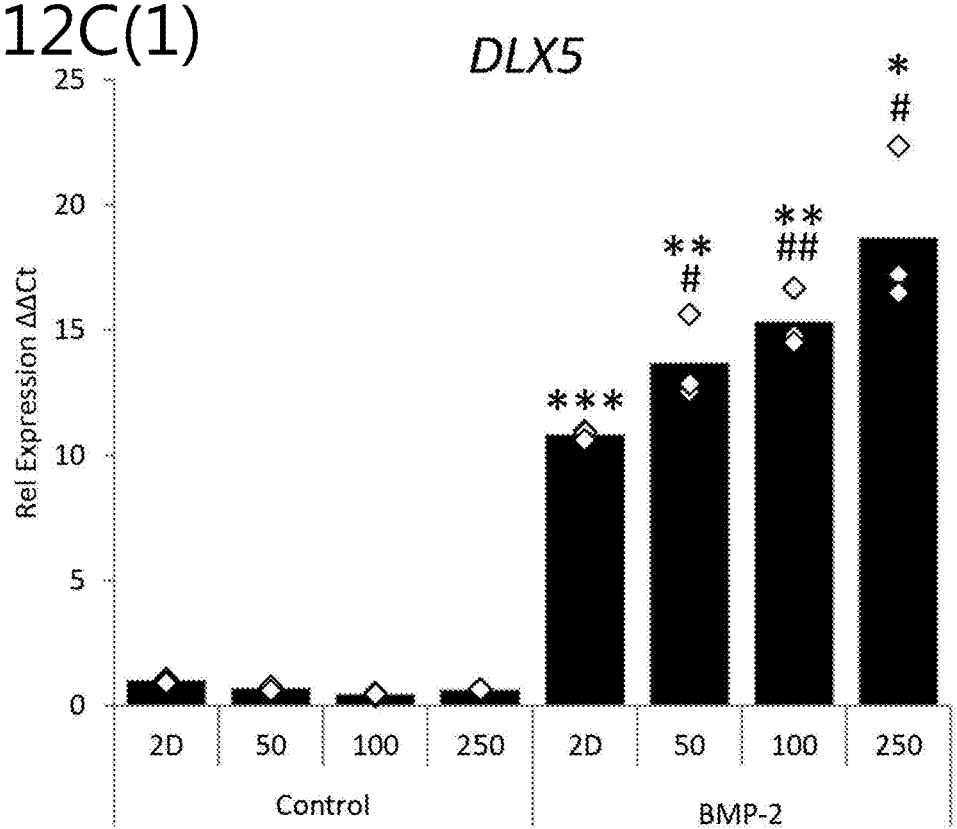
Fig. 12C(2)
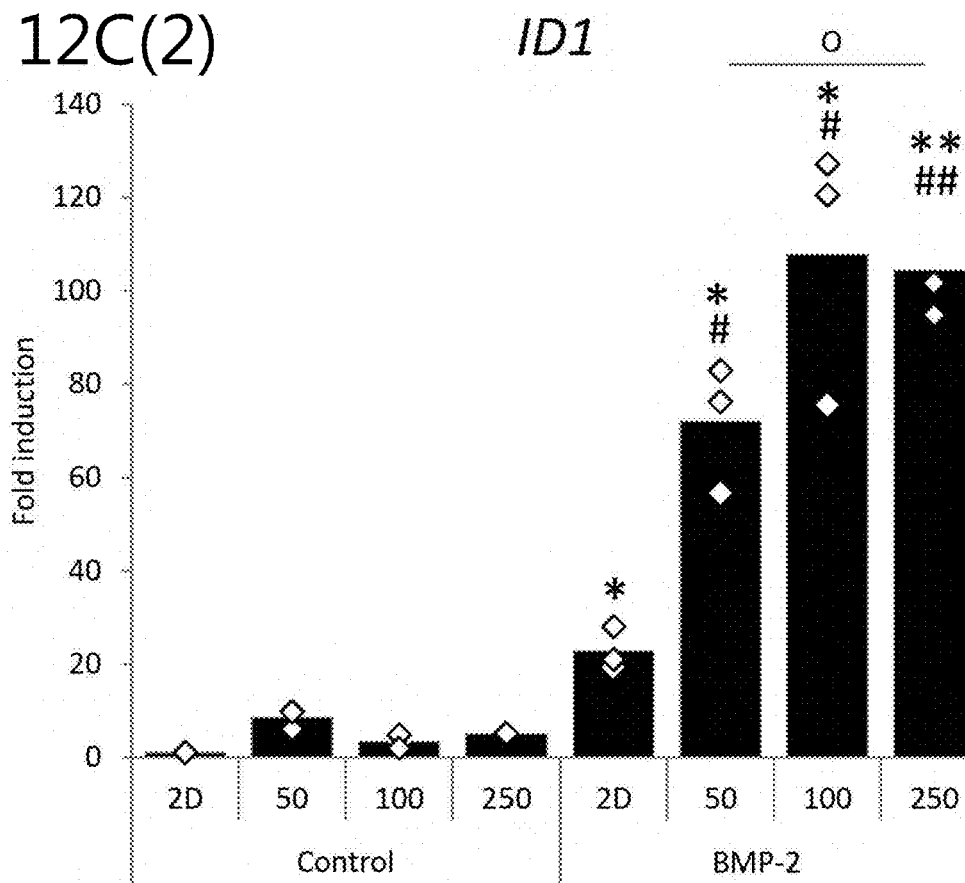

Fig. 12C(3)
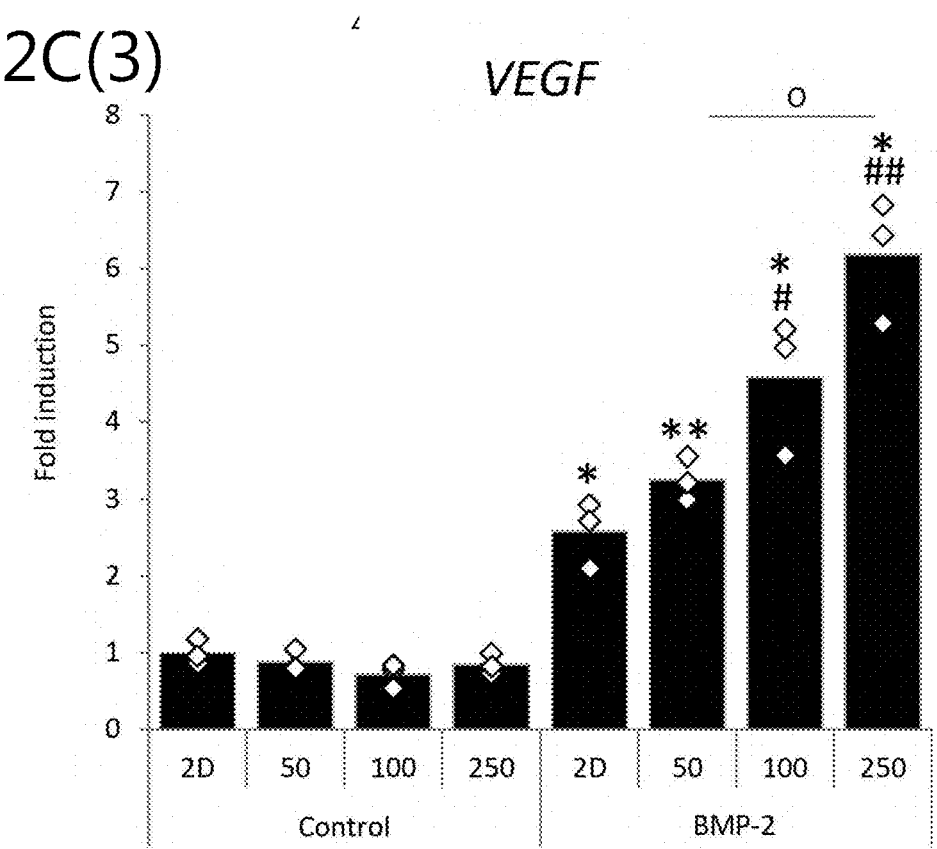
Fig. 13A
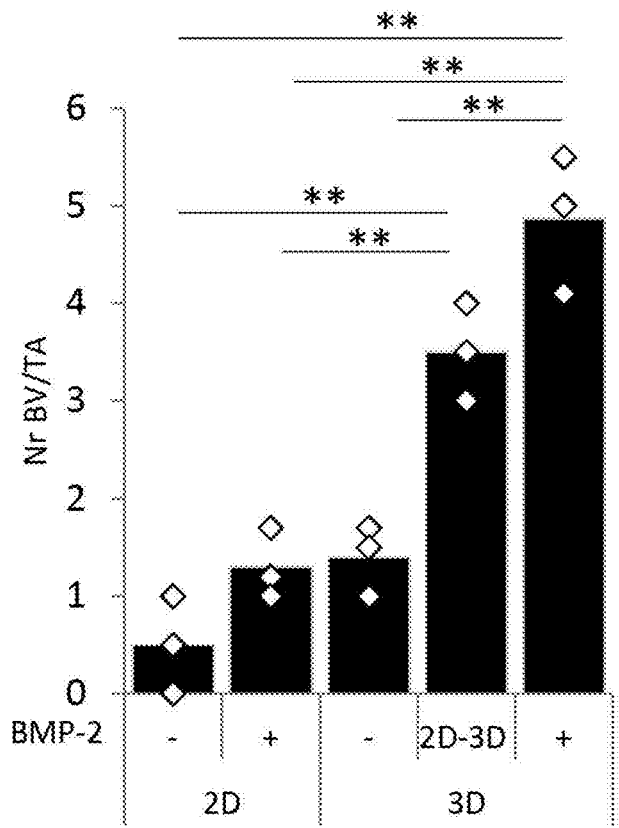

COMPOSITIONS FOR TREATMENT OF OSTEOCHONDRAL DISORDERS

FIELD OF THE INVENTION

The application provides novel cell based biocompatible carrier comprising bone forming and/or cartilage forming cells (ATMPs) and methods for making them. The application further provides pharmaceutical compositions comprising said ATMPs and method of treatments using said ATMPs. The application further relates to said ATMPS for use in the treatment of bone disorders, cartilage disorders and joint disorders. The current invention further relates to method of treatments of bone disorders, cartilage disorders and joint disorders.

BACKGROUND OF THE INVENTION

Since the introduction of tissue engineering, cell-based advanced therapy medicinal products (ATMPs) for bone regenerative strategies have drawn significant attention for clinical applications (Ma et al. (2014) *Stem Cells Transl Med* 3, 98-107). The classical elements in this strategy include cells, growth factors and a carrier material. Cells provide the driving force for bone formation, the biomaterials provide physical accommodations for the implanted cells and the growth factors act as osteoinductive molecules. For this approach, bone morphogenetic protein-2 (BMP-2), clinically approved by the FDA, is one of the most investigated growth factors in skeletal regenerative medicine. This is due to its potency in committing precursor cells towards the osteo/chondrogenic lineages in vitro as well as during in vivo postnatal fracture healing. During the latter, human periosteum derived cells (hPDC or hPDCs) are crucial, since post BMP-2 activation, these are the main contributing cells to the healing process and they possess mesenchymal stem cell characteristics at the single cell level. Standard culture of hPDCs is carried out in media containing 10% fetal bovine serum (FBS) due to its proliferative effect. However, post expansion, when engineering osteo/chondrogenic constructs based on BMP-technology, the presence of growth factors, hormones and cytokines in the serum may interfere with the effect of the BMP. Moreover, the use of FBS limits the success for clinical translation since the variability of the serum, which is specific for each individual, leads to an uncontrolled experimental outcome.

In terms of translation, clinical achievements within regenerative medicine are until today not meeting the need. Major drawbacks in current achievements include uncontrolled tissue formation, lack of integration with host tissue, unknown mechanism of action of the cell-based ATMP. Moreover, side effects due to the use of unnatural high amounts of BMPs limits translation of current ATMPs. In order to enhance the performance of implanted cells, preconditioning of the progenitor cell population is an attractive approach.

Accordingly, there remains a need for safer and better methods to treat bone disorders with an appropriate ATMP.

SUMMARY OF THE INVENTION

One aspect of the invention relates to methods for producing a cellular composition, comprising the steps of: (a) culturing mesenchymal stem cells in a serum free medium without BMP; (b) culturing the stem cells obtained after step (a) in serum free medium in the presence of BMP, optionally under conditions allowing the aggregation of cells; and (c) seeding/encapsulating the cells obtained after step (b) on/into a biocompatible carrier.

Optionally step (b) is performed under conditions allowing the aggregation of cells.

The mesenchymal stem cells are typically periosteum derived cells.

Typically biocompatible carriers comprise natural or biomimetic collagen, calcium phosphate, carboxy methyl cellulose or combinations thereof, for example calcium phosphate scaffolds such as BioOss, Copios, Nuoss or Chronos.

In specific embodiments, step (a) and step (b) are performed for at least 24 hours.

In other specific embodiments, step (a) is performed for about 1 to about 6 days, and step (b) is performed for between 1 to about 28 days.

In other specific embodiments, step (a) is performed for about 3 to about 6 days, and step (b) is performed for between 1 to about 28 days.

In other specific embodiments step (a) is performed for about 6 days and step (b) is performed for 1 to about 28 days.

Typically the BMP is selected from the group consisting of BMP2, BMP4, BMP6, BMP7, BMP9, GDF5, and TGFβ, or any combinations thereof.

More specifically the BMP is BMP2, BMP6 or a combination of BMP-2 and BMP-6.

In certain embodiments BMP in step (b) is used in a concentration of about 2 to 2000 ng/ml serum free medium.

In more specific embodiments BMP in step (b) is used in a concentration of about 100 ng/ml serum free medium.

In certain embodiments, the methods further comprise in step (b) a growth factor selected from the group consisting of TGFbeta1, FGF2 and GDF5 or any combination thereof, and this for example in a concentration of about 0.01 ng to about 100 ng/ml serum free medium.

More specifically the growth factor in step (b) is used in a concentration of about 0.01 ng to about 10 ng/ml serum free medium, and more specifically TGFbeta1 is about 0.1 ng/ml serum free medium, FGF2 is about 0.2 ng/ml serum free medium, and for GDF5 is about 1 ng/ml serum free medium.

In specific embodiments cells are cultured in step (b) with BMP and with TGFbeta1 at a concentration of about 0.1 ng/ml serum free medium, with FGF2 at a concentration of about 0.2 ng/ml serum free medium, and with GDF5 at a concentration of about 1 ng/ml serum free medium; and wherein said BMP is a combination of BMP2 and BMP6 at a concentration of about 100 ng/ml serum free medium for each BMP2 and BMP6.

In a specific embodiment the serum free medium comprises two basal cell culture media in a ratio of about 1:1 (v/v), Insulin, Transferrin, Selenium, α-ketoglutarate, Ceruloplasmin, Cholesterol, Phosphatidyl ethanolamine, α-tochoferol acid succinate.

Reduced glutathione, Taurine and L-ascorbic acid 2-sulphate.

In more specific embodiments the serum free medium further comprises one or more of ceruloplasmin, triiodothyronine, hydrocortisone, and parathyroid hormone.

Another aspect of the invention relates to cellular compositions comprising a serum free medium comprising at least one BMP and a biocompatible carrier with mesenchymal stem cells stimulated towards the osteochondral lineage, obtainable by the methods as described above.

Herein the stem cells can occur partially as cell aggregates.

The stem cells are typically periosteum derived cells.

The biocompatible carrier typically comprises collagen, calcium phosphate, carboxy methyl cellulose, hydrogel or combinations thereof.

Examples of biocompatible carriers are calcium phosphate scaffold such as BioOss®, Copios®, Nuoss™ or Chronos®.

Another aspect relates to pharmaceutical compositions comprising the cellular composition described above and a pharmaceutically acceptable carrier, excipient or solution.

Another aspect relates to pharmaceutical compositions comprising the cellular composition described above for use as a medicament, for example for use in the treatment of a bone, cartilage or joint disorder.

Examples hereof are a bone fracture, a non-healing bone defect, an osteochondral defect or damaged joint surface, or a metabolic bone disease.

Another aspect of the invention relates to methods of treatment of a bone, cartilage or joint disorder in an animal, comprising the administration of a cellular composition as described above.

Another aspect of the invention relates to the use of a serum free medium without BMP and a serum free medium with BMP in a sequential use for the differentiation of mesenchymal stem cells into the osteochondral lineage.

The present inventors have found a method to enhance the performance of implanted cells, by preconditioning the progenitor stem cell population.

Moreover, the present invention provides for a more robust long-term outcome by designing a tissue intermediate which is aimed to restore or regenerate a damaged tissue in a collaborative effort between the implant or ATMP and the body's own natural healing processes, in place of stimulating tissue formation in an autonomous manner (Leijten et al, (2014) *Adv Drug Deliv Rev* 84, 30-44).

More in particular, the present inventors use a media which does not induce proliferation, but rather maintain cell viability. Upon BMP supplementation, such as BMP-2, the media support osteochondrogenic differentiation by stem cells such as Periosteum derived cells, e.g. hPDCs. The present inventors found serum free chemically defined media (SFM) which fulfilled these requirements (Harrison E. T., Jr. et al. (1991) *Exp Cell Res.* 192, 340-355; US20010039050), and further explored the use of these types of media in order to find a better, efficient and more robust cell-based strategy, suitable in the development of cell-based translational ATMPs which were defined as a chemically defined BMP-Technology Media (CDM).

In fact, cells stimulated with this kind of medium displayed an unexpected superior differentiation profile as compared to cells stimulated under serum containing conditions. Subsequently, a two-step differentiation protocol was developed where cells were preconditioned in said serum free medium prior to BMP stimulation such as with addition of exogenous BMP-2 to said medium. The pre-culture affects the cellular phenotype which leads to an elevated response to BMP-stimulation, resulting in enhanced cartilage and bone formation in vivo. Subsequently a biomimicking system was developed where BMP (such as BMP-2) stimulated cellular aggregates formed a tissue intermediate which upon in vivo implantation forms cartilage after one week in vivo. These results revealed a cell-based construct, developed with clinical translation in mind, where a media specific cell-enrichment leads to more efficient cartilage formation in vivo, implying better treatment than the current alternatives for bone disorders.

Some basic aspects of the current invention relate to the pre-culture of stem cells, such as hPDCs, in serum free media, such as the CDM, leading to those cells losing their MSC phenotype and about 50% become positive for CD34. Further stimulation of these cells with BMPs for about another 6 days after the pre-culture, showed a more potent response to said BMP-stimulation (by BMP-2, BMP-4, BMP-6, BMP-7, BMP-9 and GDF5) when scoring for osteogenic or chondrogenic differentiation. Upon in vivo implantation, they form more cartilage 3 weeks post implantation. This phenomenon is further improved in combination with (micro)aggregation.

The present invention is based on the unexpected finding that certain treatment of cells, including specific culturing in serum-free conditions, results in cell-based ATMPs with improved in vivo properties and capacities. Said treatments or specific culture conditions or combinations are not suggested by the prior art, and said ATMPs show unexpected biological properties, in particular have significant capacities in the treatment of bone disorders, cartilage disorders and joint disorders. Said improved biological properties relate to an improved in vivo effect, compared to untreated or not pre-conditioned cells in ATMPs or any other cell based ATMP that is currently known.

The application discloses an ATMP comprising:
  (i) stem cells that are cultured in serum free medium and said medium comprises at least one BMP and said stem cells are at least partly grown in aggregates; and
  (ii) a biocompatible carrier.

The stem cells can be mesenchymal cells, such as periosteum derived cells.

The cells are typically mammalian cells, more specifically human cells.

Examples of biocompatible carriers comprise collagen, calcium phosphate, carboxy methyl cellulose, hydrogel or combinations thereof.

Examples of calcium phosphate scaffolds are BioOss®, Copios®, Nuoss™ or Chronos®.

The application discloses methods for making an ATMP, comprising:
  (a) culturing stem cells/in a serum free medium without BMP;
  (b) then the cells of step (a) are further cultured in aggregates;
  (c) then the cells of step (b) are further cultured in the presence of BMP; and
  (d) then the cells of step (c) are seeded to a biocompatible carrier.

The stem cells are typically mesenchymal cells, such as periosteum derived cells.

The stem cells are typically are mammalian cells, more specifically human cells.

Examples of biocompatible carriers comprise collagen, calcium phosphate, carboxy methyl cellulose or combinations thereof.

Examples of calcium phosphate scaffolds are BioOss, Copios, Nuoss or Chronos.

In the method, typically step (a) is at least 1 day and step (b) and (c) are at least 24 hours.

In the method, typically step (a) is about 3 to about 6 days, and step (b) and (c) are between 1 to about 28 days, and (b) and (c) start simultaneously after step (a).

In the method, typically step (a) is about 6 days and step (b) and (c) are 1 to about 28 days, and step (b) and (c) start simultaneously after step (a).

In the method, the BMP can be BMP2, BMP4, BMP6, BMP7, BMP9, GDF5, TGFβ, or any combination thereof.

More specific the BMP in step (c) is selected from the group: BMP2, BMP6 or a combination of BMP-2 and BMP-6.

The BMP in step (c) can be used in a concentration of about 2 to 2000 ng/ml, for example said BMP is used in a concentration of about 100 ng/ml.

In step (c) BMP can be added together with an extra growth factor selected from the group consisting of: TGF-beta1, FGF2, GDF5 or any combination thereof.

The said extra growth factor in step (c) is for example added such that the final concentration in the culture is about 0.01 ng/ml to about 100 ng/ml.

The said extra growth factor in step (c) is for example added such that the final concentration in the culture is about 0.01 ng/ml to about 10 ng/ml, and more specifically for TGFbeta1 is about 0.1 ng/ml, for FGF2 is about 0.2 ng/ml, and for GDF5 is about 1 ng/ml.

In step (c) the cells can be cultured with BMP together with the extra growth factors TGFbeta1 at a concentration of about 0.1 ng/ml, FGF2 at a concentration of about 0.2 ng/ml, and GDF5 at a concentration of about 1 ng/ml; and wherein said BMP is a combination of BMP2 and BMP6 at a concentration of about 100 ng/ml for each BMP2 and BMP6.

An example of a serum free medium which can be used comprises: two basal cell culture media in a ratio of about 1:1 (v/v), Insulin, Transferrin, Selenium, α-ketoglutarate, Ceruloplasmin, Cholesterol, Phosphatidyl ethanolamine, α-tochoferol acid succinate, Reduced glutathione, Taurine and L-ascorbic acid 2-sulphate.

The medium can further comprise triiodothyronine, and/or hydrocortisone, and/or parathyroid hormone.

The cells as obtained or obtainable by the application for use as a medicine for the treatment of an animal having a bone or cartilage or joint disorder, such as a bone fracture, a non-healing bone defect, an osteochondral defect or damaged joint surface, or a metabolic bone disease.

Any eukaryotic cell can be used in the initial step of culturing the stem cells as long as it has a phenotype of a cell that is a primitive mesenchymal phenotype. Such a cell could express membrane markers such as CD73, CD90 or CD105, transcription factors such as PRX1/2 or cytoskeletal elements such as nestin and αSMA (alpha smooth muscle actin) and display multipotent differentiation capacity under standard in vitro conditions as known to a person skilled in the art. For stem cells, for example embryonic stem cells or reprogrammed somatic cells (IPSC) or partially reprogrammed somatic cells, it is required that such stem cells are first differentiated to such a primitive mesenchymal phenotype. At that moment, these differentiated cells can be used according to the methods of the present invention. The whole method, including such pre-differentiation of such stem cells together with the proliferation and differentiation methods as described in detail in this invention, are contemplated in the present invention. In one embodiment, such cells to be used in the initial step of culturing the (stem) cells express at least 1, 2, 3, 4, 5, 6, 7, 8 or 9 markers selected from the list containing: CD90, CD44, CD105, CD146, CD73, CD166, nestin, αSMA and PRX1 and are negative for one or more of CD34, CD45 and CD14. In one embodiment such cells to be used in said initial step are cells that are derived from neural crest and meso-endodermal lineage during development. Such cells include but are not limited to hematopoietic (stem) cells and other stem cells derived from neural crest.

The invention is also directed to methods of using the ATMP produced by the methods of the present invention for the treatment of bone disorders, in particular bone fractures, more particularly non-union fractures (bone fractures that do not heal naturally).

Other embodiments, objects, features and advantages will be set forth in the detailed description of the embodiments that follows. The summary above is to be considered as a brief and general overview of some of the embodiments disclosed herein, is provided solely for the benefit and convenience of the reader, and is not intended to limit in any manner the scope encompassed by the appended claims.

BRIEF DESCRIPTION OF THE DRAWINGS

FIGS. 1a-1h. Serum concentration in the medium affects cell proliferation and BMP-2 induced osteogenic differentiation.

Cell proliferation and viability was measured in hPDCs cultured for 6 days in growth medium containing 0-10% FBS, an in-house serum free chemically defined medium (CDM or BTM), a commercial serum free medium (SFM) or standard osteogenic medium (OM). DNA quantification was performed after 1, 3 or 6 days of culture and normalized to DNA content at day 0 (FIG. 1a). Cell viability after 6 days was investigated by a live/dead staining and percentage of apoptotic cells were quantified (FIG. 1b). Elevated DNA content was confirmed upon BMP-2 supplementation (FIG. 1c), together with induced osteogenic differentiation confirmed by ALP-activity normalized to DNA content (FIG. 1d). Gene expression for, (FIG. 1e) chondrogenic markers displayed enhanced chondrogenic differentiation in cells stimulated with BMP-2 supplemented CDM as compared to serum containing conditions depicted by increased Sox9 and Aggrecan expression. (FIG. 1f) Up-regulated osteogenic differentiation depicted by Runx2 and Osterix expression in cells stimulated with BMP-2 supplemented CDM as compared to media containing serum. (FIG. 1g) Increased BMP-signalling was seen in cells stimulated with BMP-2 supplemented CDM depicted by enhanced expression of ID1 and Dlx5. (FIG. 1h) An ID1 reporter cell line was used to detect active BMP-levels in freshly made (FrM) and conditioned media (CoM). Higher level of active BMPs could be detected in conditioned media as compared to stimulation media in BMP-2 supplemented CDM and 10% FBS. Higher amount of BMPs were also found in fresh BMP-2 supplemented CDM as compared to 10% FBS. No difference was detected in media containing 1% FBS. Low levels of BMPs were detected in conditioned media from cells stimulated with standard osteogenic media (OM). Statistical significance to standard culture media containing 10% FBS: #: <0.05.

After 6 days of pre-culture under serum free conditions, a change in progenitor cell phenotype can be seen. (FIG. 2a) DNA quantification after 6 days in cells pre-conditioned in CDM or GM normalized to day 0. (FIG. 2b) DNA per cell after 6 days of pre-conditioning. Pre-conditioning induced elevated expression of cell cycle regulators (FIG. 2c) CDK1, (FIG. 2d) CCNE1 and (FIG. 2e) BIRC5. mRNA transcript analysis of (FIG. 2f) BMP type 1 and type 2 receptors, (FIG. 2g) CD34 and osteogenesis-related markers FGF2, VEGF and MMP9.

Figure 3A:
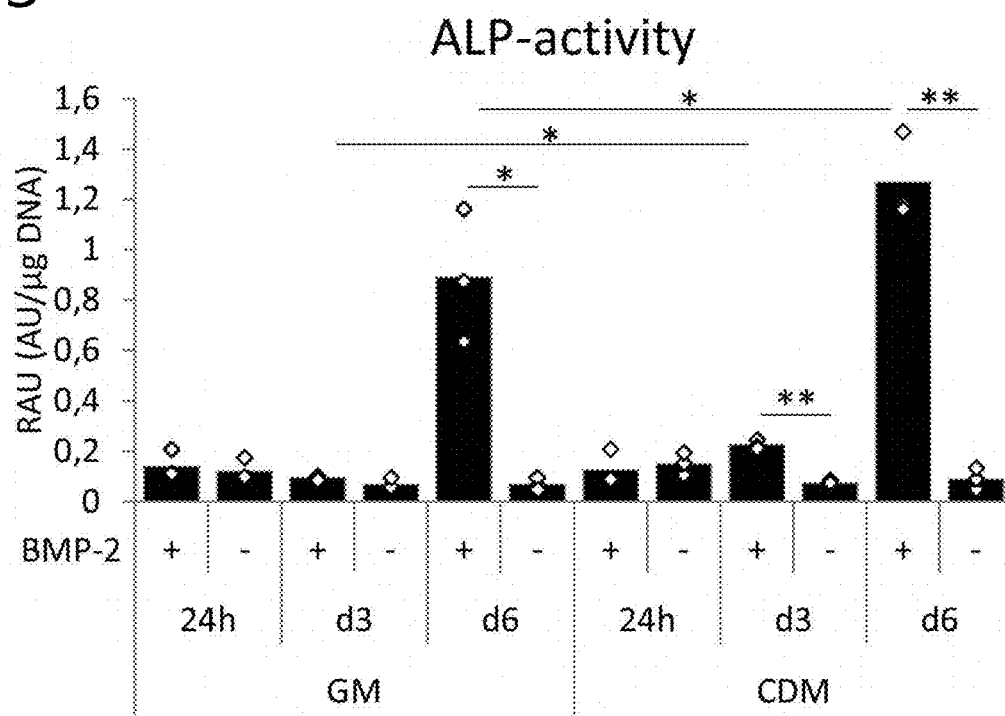
FIGS. 3a-3e. Serum free pre-culture enhance BMP-2 induced differentiation.
Figure 3B:
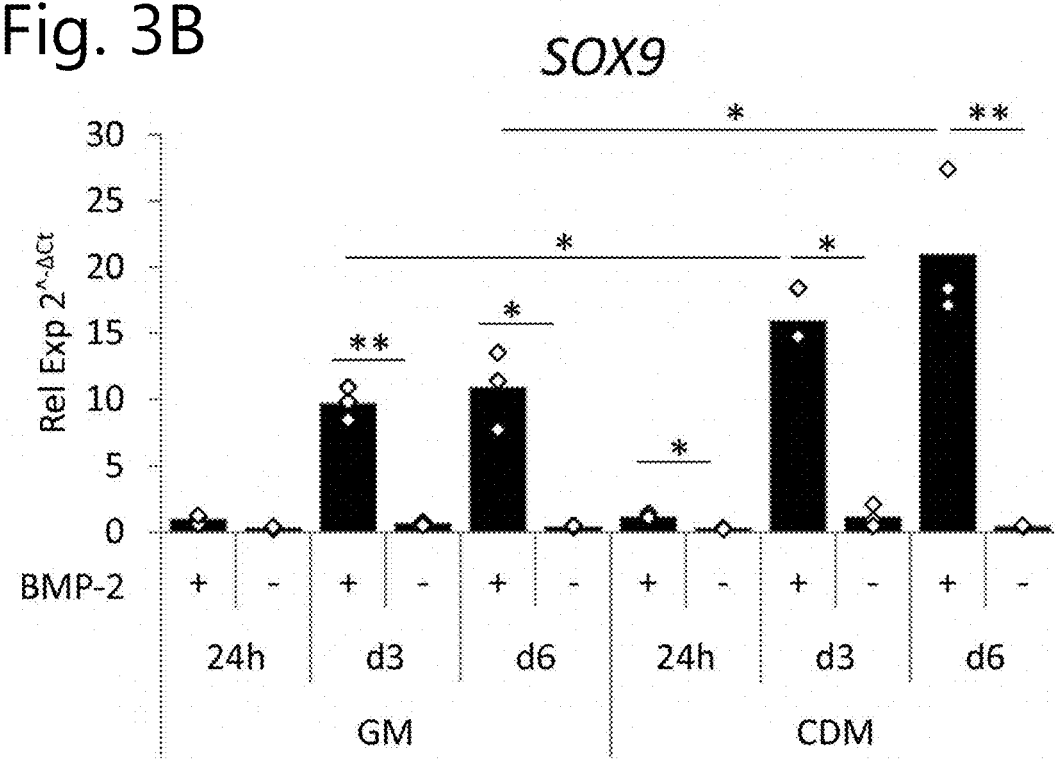
Figure 3C:
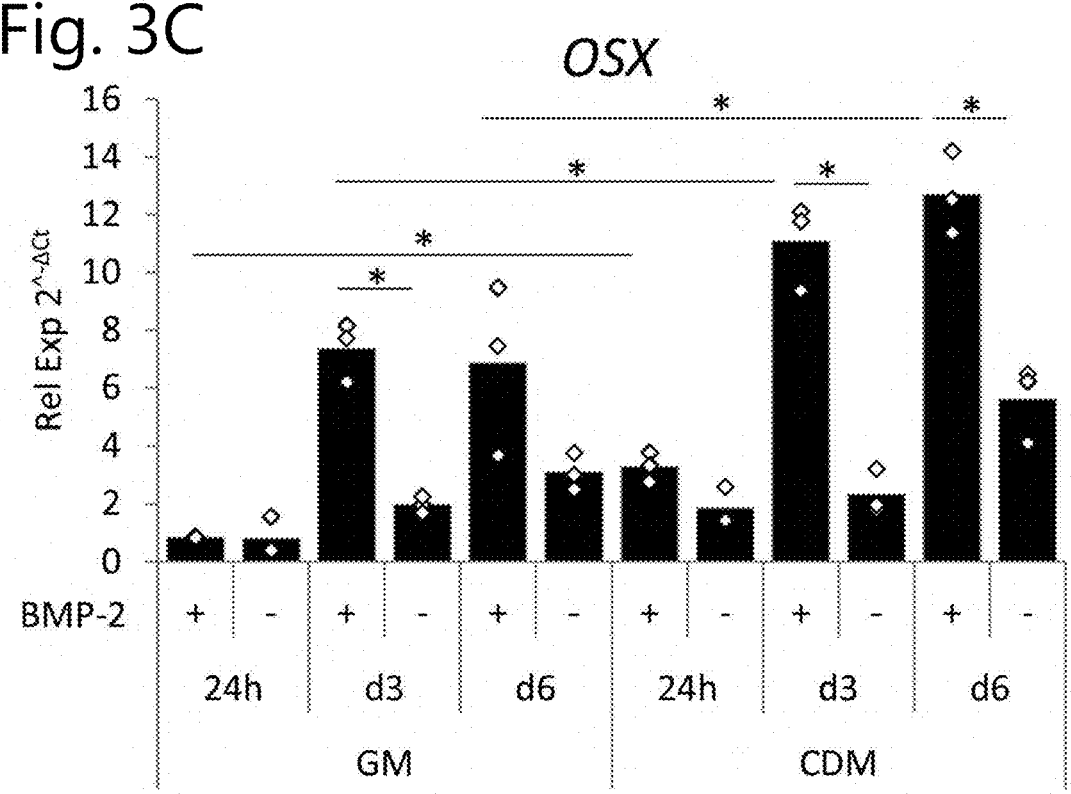
Figure 3D:
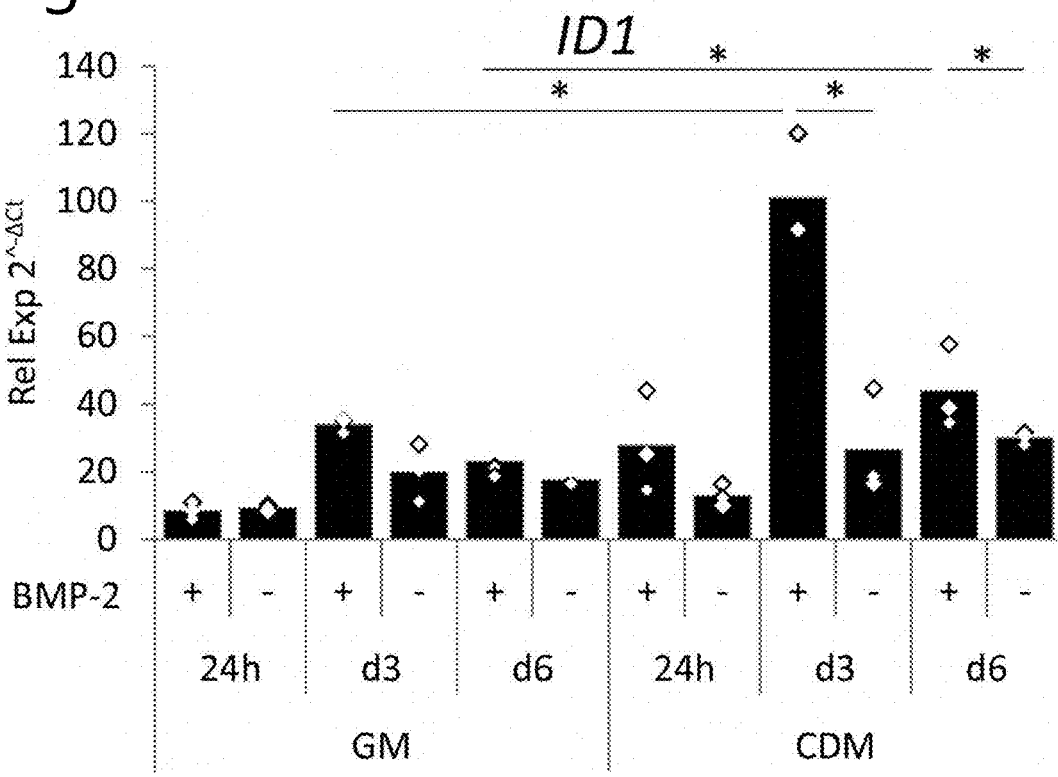
Figure 3E:
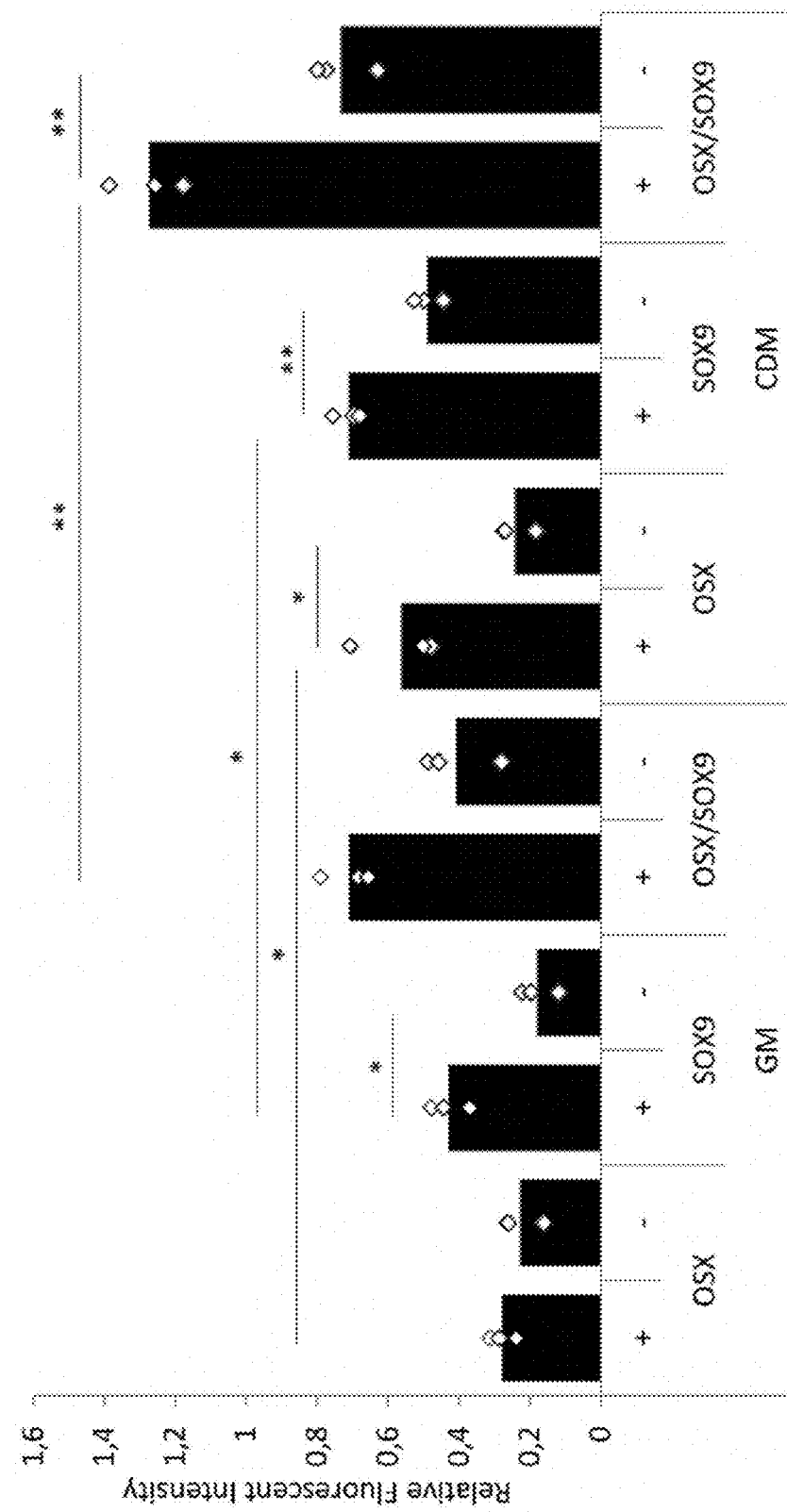

After 6 days of pre-culture followed by 6 days of BMP-2 stimulation in CDM, a difference in response to BMP-2 was seen. BMP-2 stimulation induced elevated ALP activity in CDM pre-cultured cells after 3 days of stimulation (FIG. 3a). On gene expression level, elevated (FIG. 3b) Sox9, (FIG. 3c) Osterix and (FIG. 3d) ID1 expression was depicted after 24 h, 3 and 6 days of BMP-2 stimulation. The serum-free pre-culture leads to a robust differentiation of the cell population, towards a dual osteo/chondrogenic lineage. Immunohistochemistry for chondrogenic marker Sox9 and Osteogenic marker Osterix with DAPI as nuclear stain confirmed a dual osteo/chondrogenic differentiation profile in cells pre-cultured in CDM followed by BMP-2 stimulation confirmed by quantification (FIG. 3e).

FIG. 4a, inclusive of FIGS. 4a(1)-4a(5). Serum free pre-culture enhance BMP-2 induced differentiation.

After 6 days of pre-culture followed by 6 days of BMP-2 stimulation in CDM, a difference in response to BMP-2 was seen upon analysis mRNA transcript for additional markers: COLL2A1 (FIG. 4a(1)), COLL10A1 (FIG. 4a(2)), RUNX2 (FIG. 4a(3)), COLL1A1 (FIG. 4a(4)), and DLX5 (FIG. 4a(5)).

FIGS. 5a-5d''''. The enhanced stimulatory potential in CDM pre-conditioned cells was not BMP-2 specific.

Figure 5B:
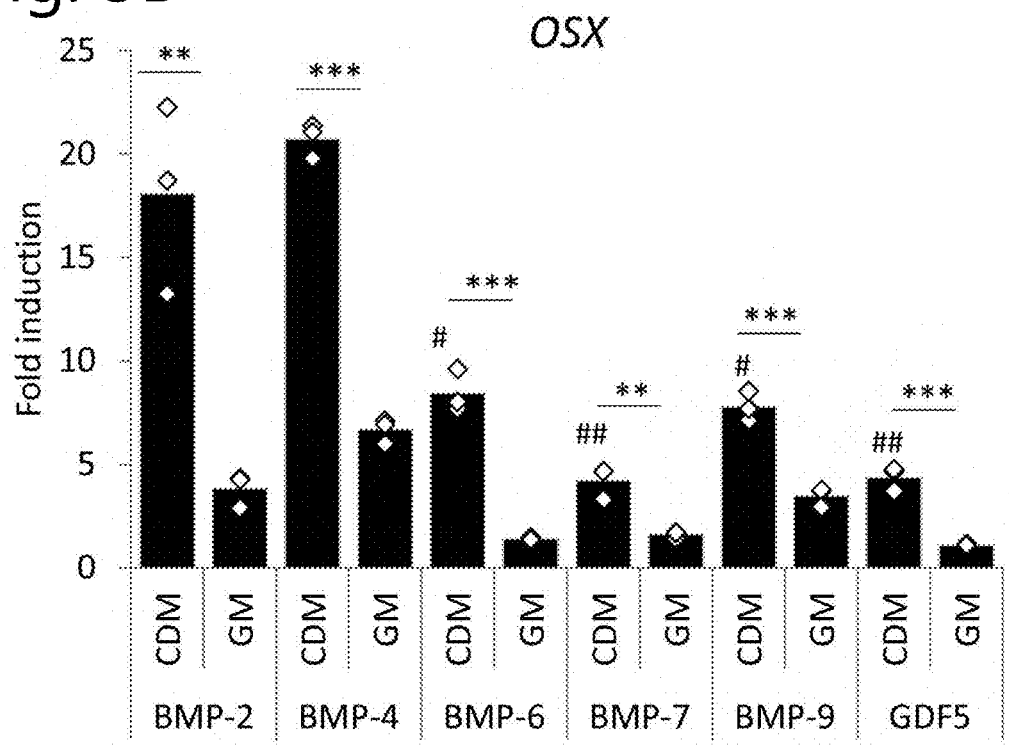
Figure 5C:
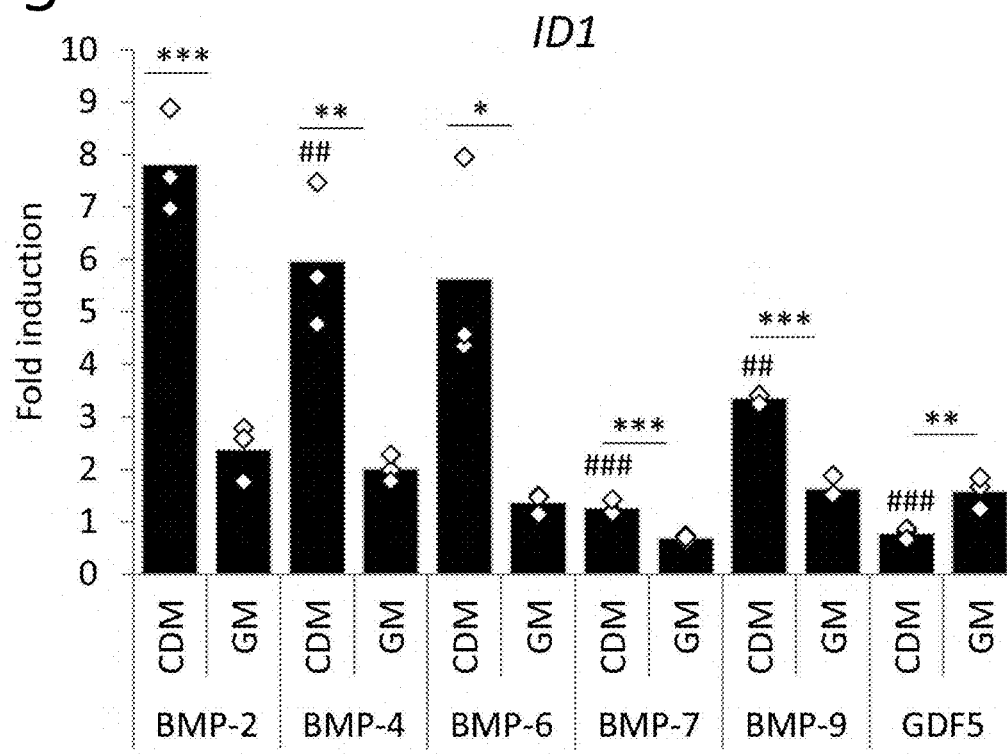
Figure 5D:
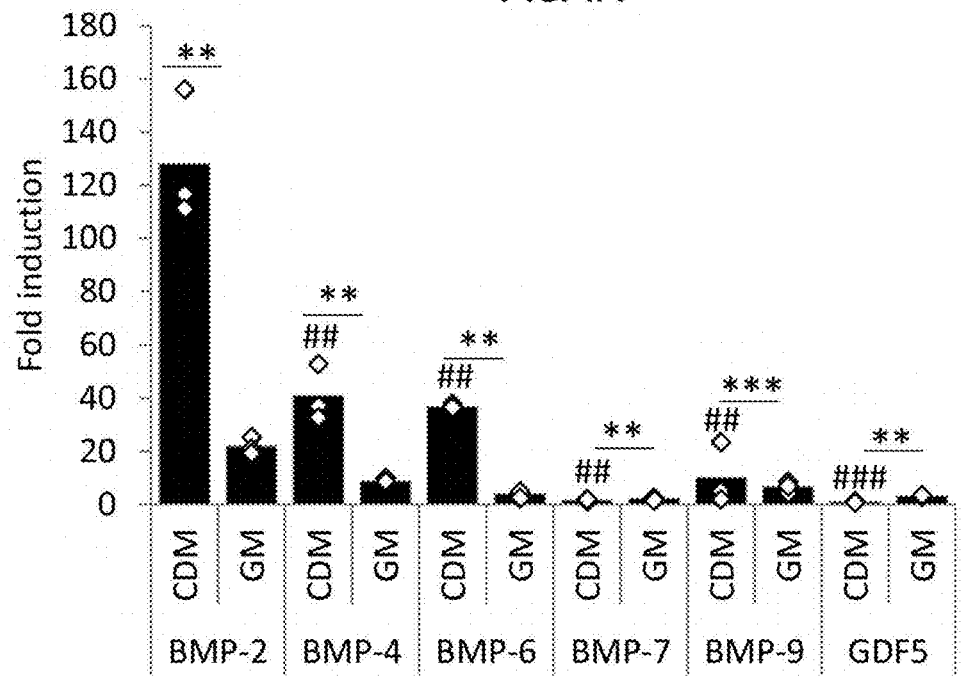
Figure 5D:
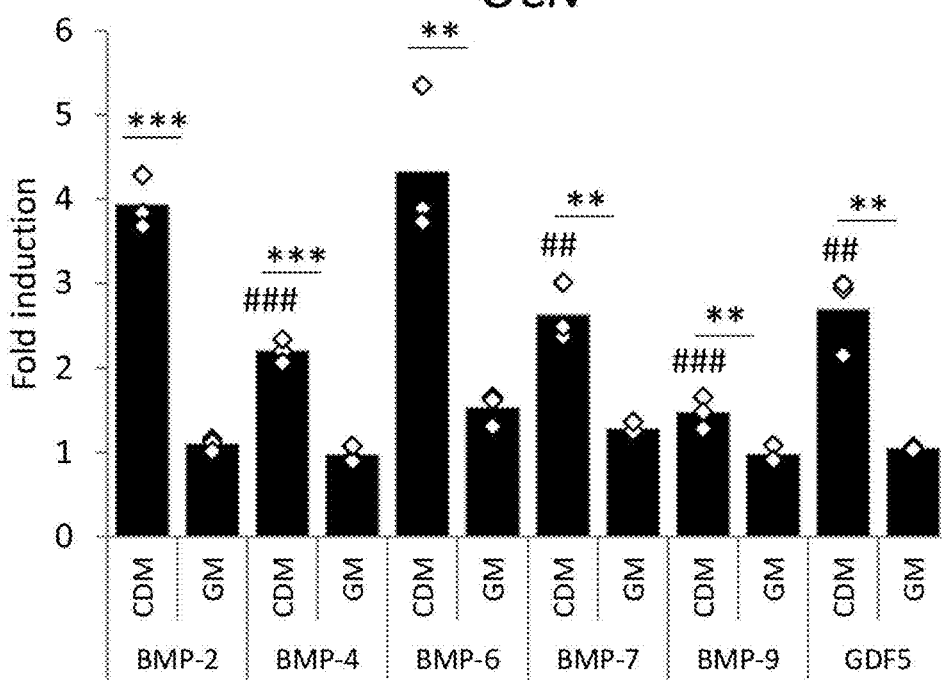
Figure 5D:
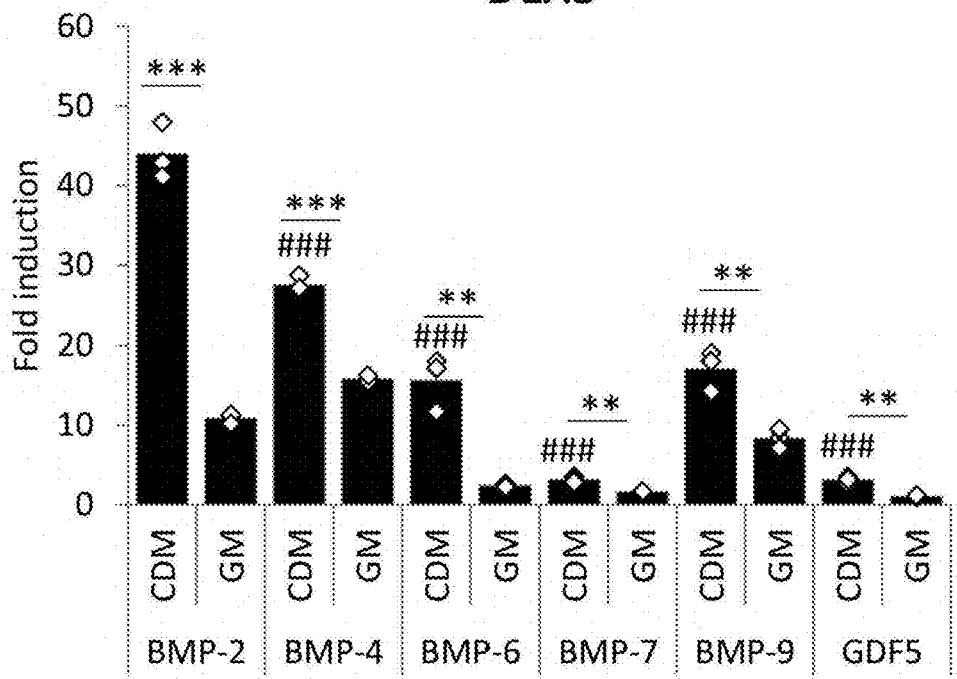
Figure 5D:
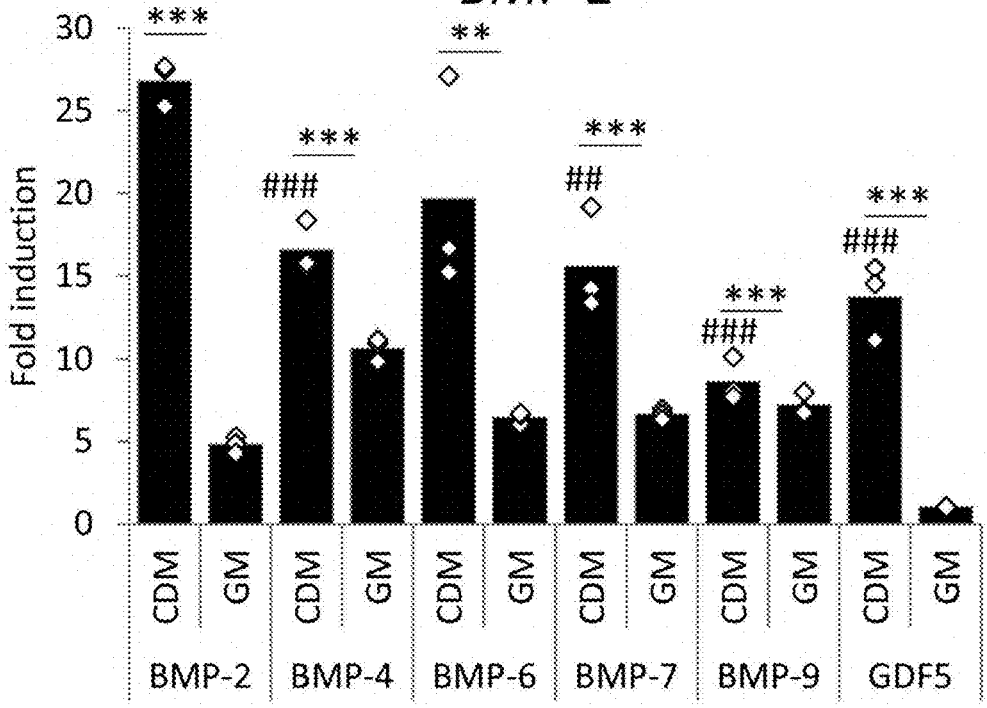
Figure 6B:
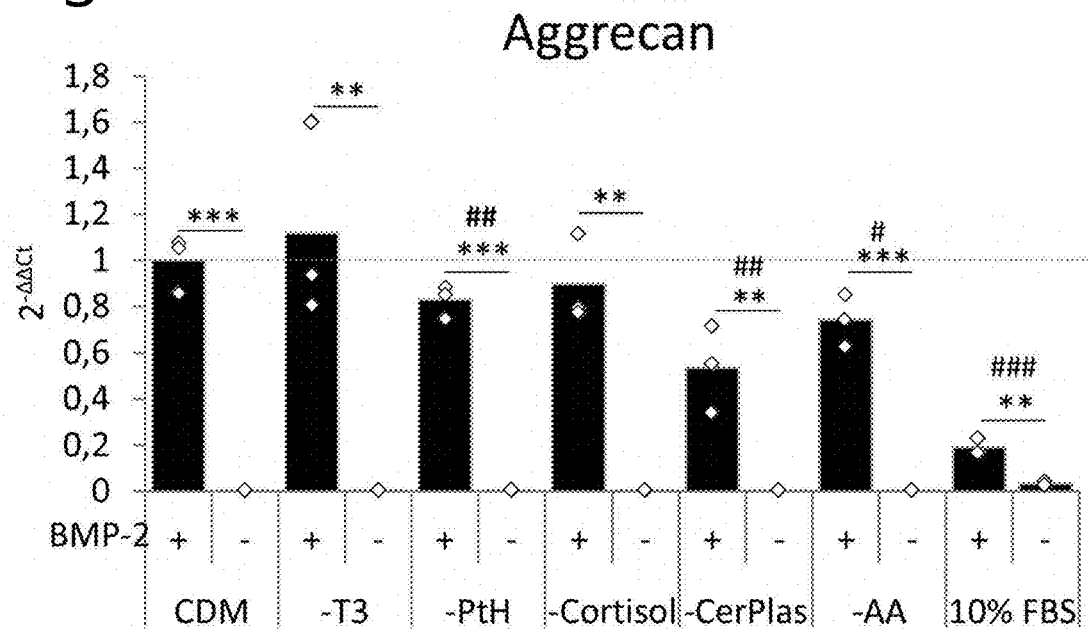
Figure 6C:
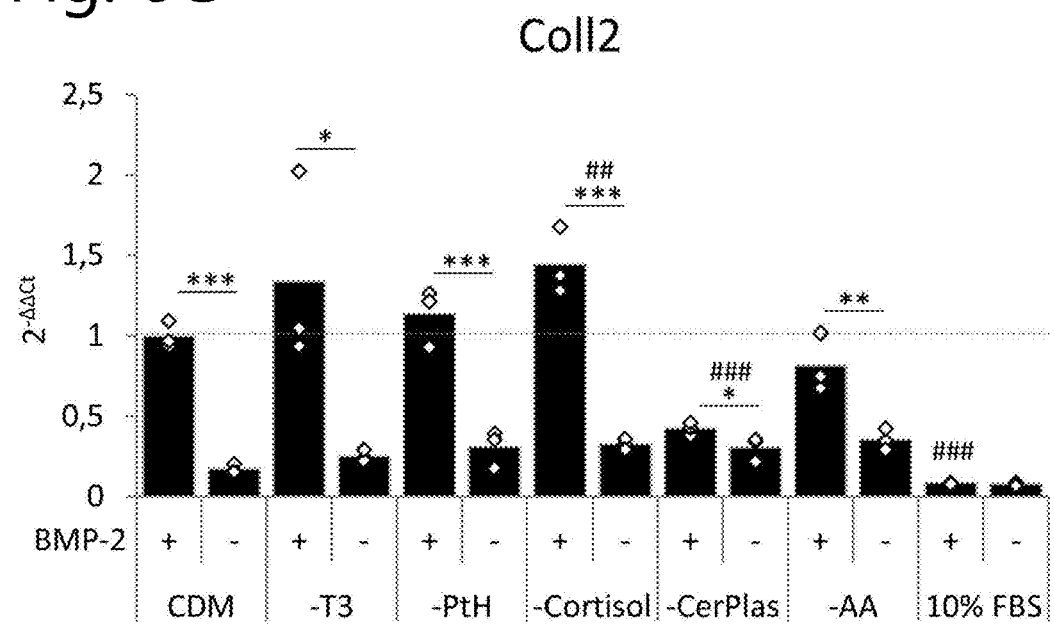
Figure 6D:
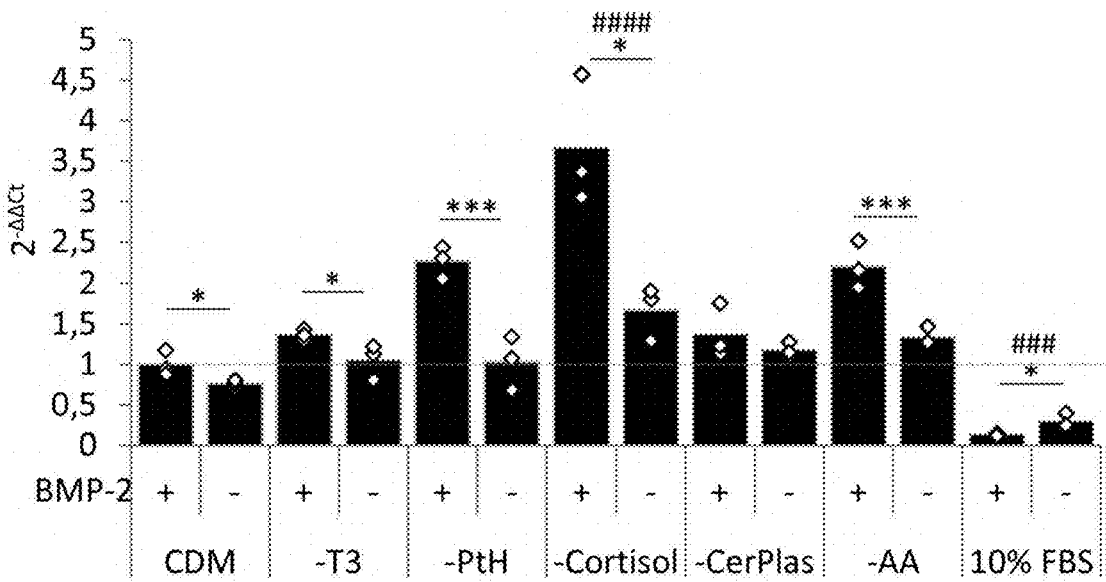
Figure 6E:
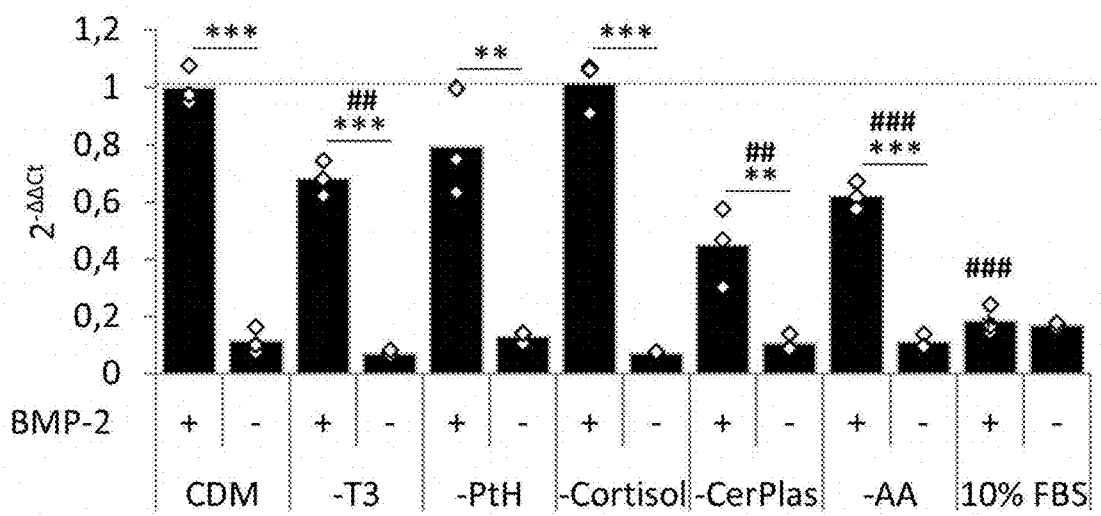
Figure 6F:
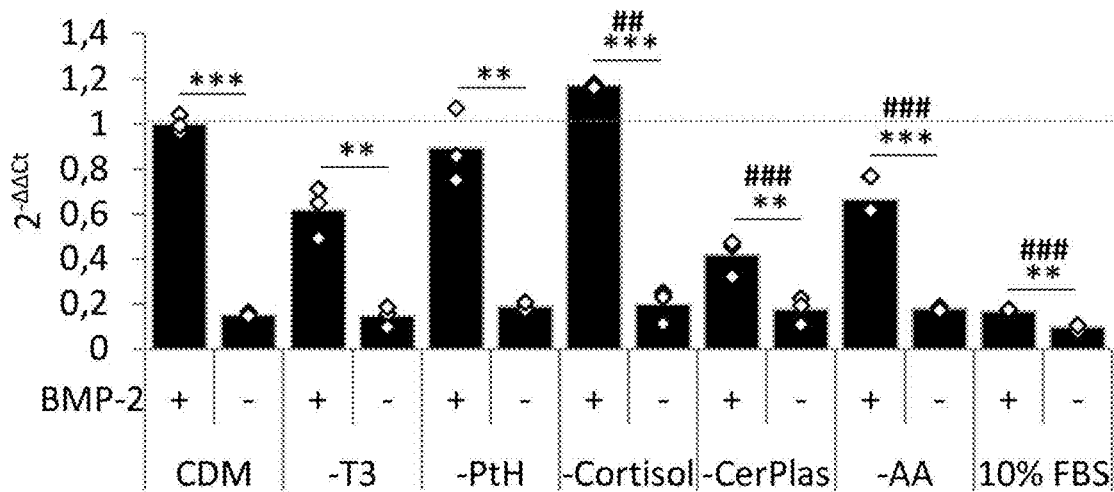
Figure 6G:
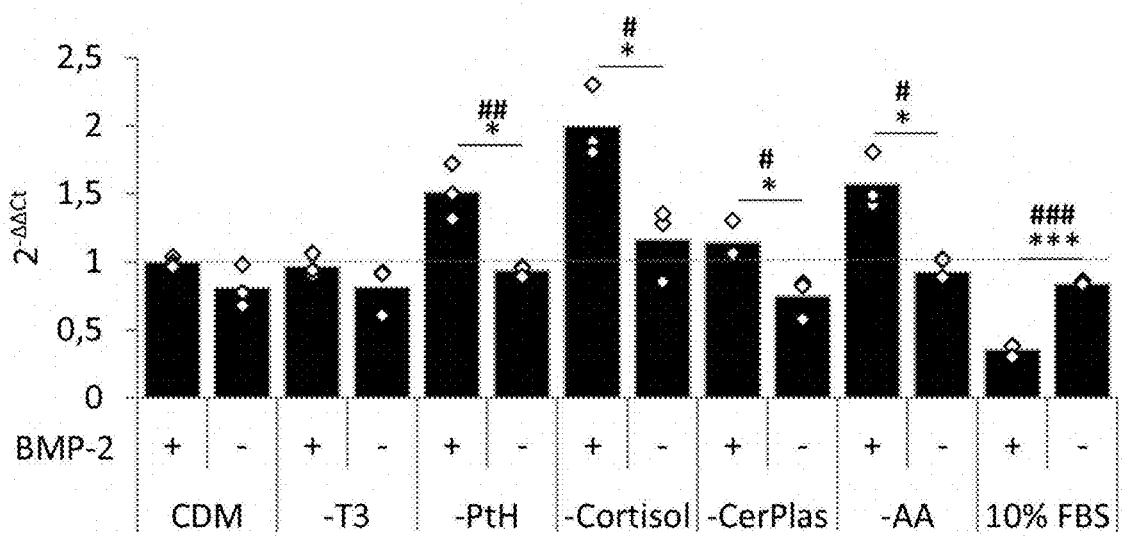
Figure 6H:
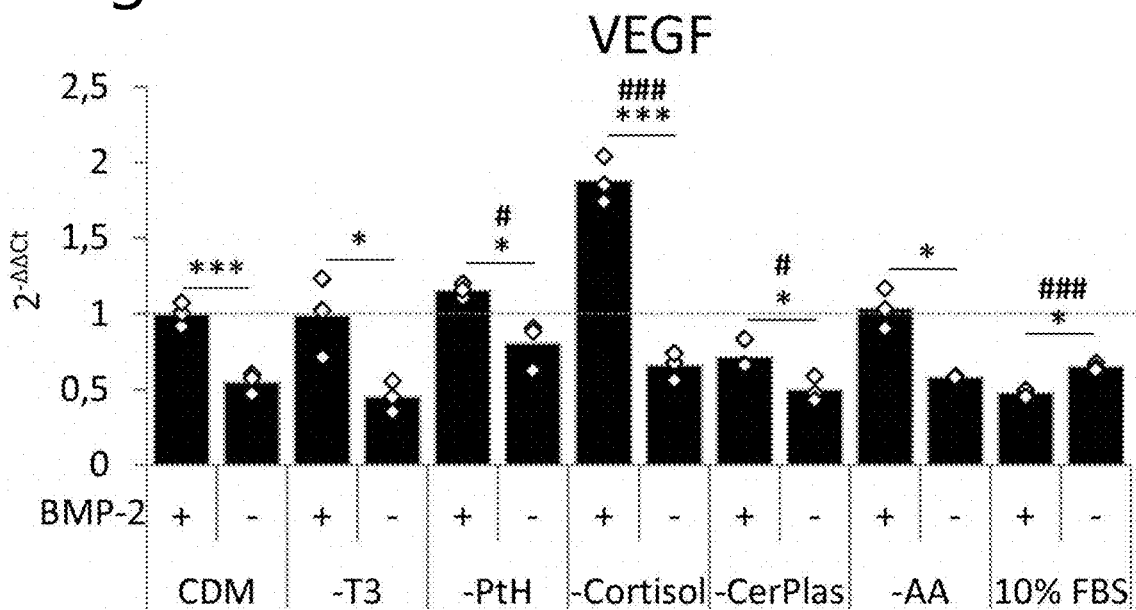
Figure 6I:
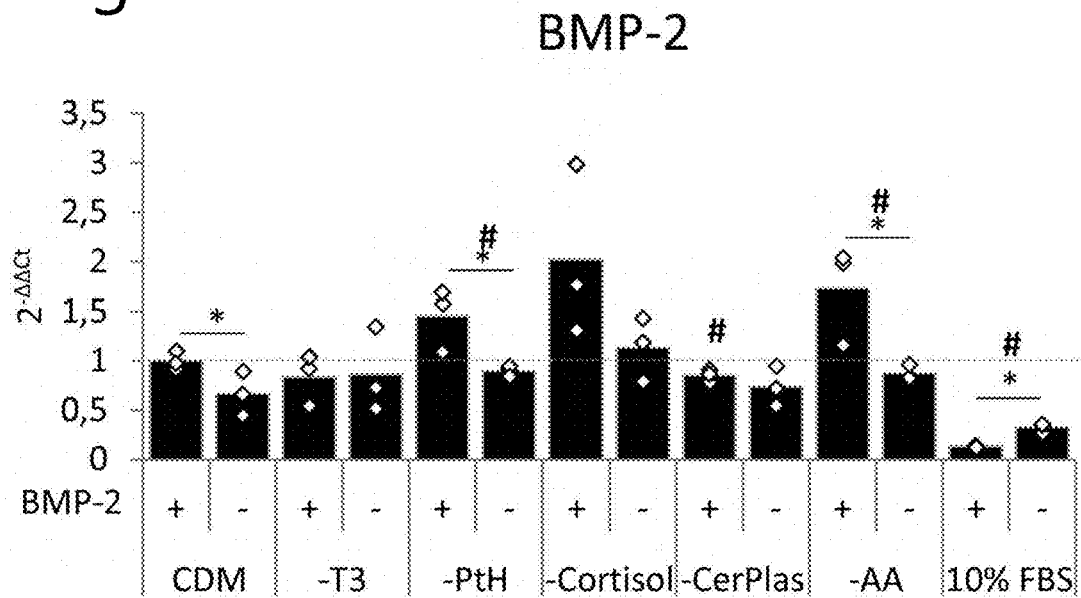
Figure 6J:
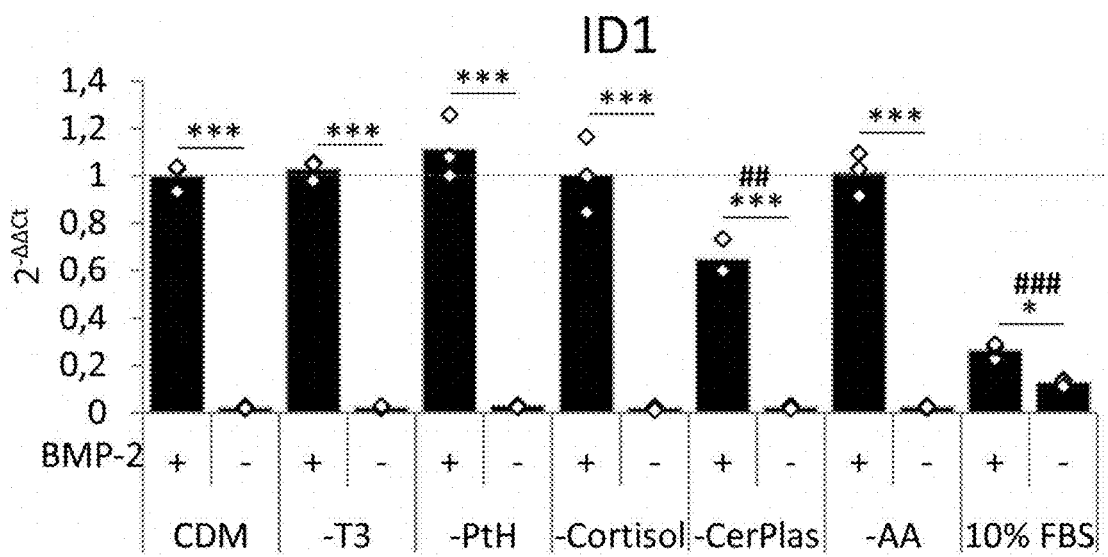

Serum free pre-conditioning led to enhanced osteochondrogenic differentiation in vitro upon stimulation with several BMP-ligands. After 6 days of pre-conditioning in CDM or GM followed by 6 days of BMP-2 stimulation in CDM, a difference in response to BMP-2 was observed. mRNA transcript analysis after pre-conditioning of hPDCs followed by 6 days of stimulation of BMP-2, BMP-6, BMP-7, BMP-9 and GDF5 depicted by (FIG. 5a) SOX9, (FIG. 5b) OSX and (FIG. 5c) ID1, ACAN (FIG. 5d), OCN (FIG. 5d'), DLX5 (FIG. 5d''), BMP-2 (FIG. 5d'''), and VEGF (FIG. 5d''''). Statistical significance to BMP-2 stimulated samples: #: <0.05, ##: <0.01, ###: <0.001, n=3).

FIGS. 6a-6j. Removal of components in CDM improve the stimulatory effect of BMPs.

Upon pre-conditioning following BMP-stimulation in CDM, in which specific components have been removed, an effect on differentiation was seen. mRNA transcript analysis for each of Sox9 (FIG. 6a), Aggrecan (FIG. 6b), Coll2 (FIG. 6c), CollX (FIG. 6d), Runx2 (FIG. 6e), Osterix (FIG. 6f), Osteocalcin (FIG. 6g), VEGF (FIG. 6h), BMP-2 (FIG. 6i), and ID1 (FIG. 6j) displayed the effect on marker genes for chondrogenesis and osteogenesis. Dotted line reflects expression level in complete CDM. Statistical significance to full media composition: #: <0.05, ##: <0.01, ###: <0.001, n=3).

FIGS. 7a-7e. CD34+ cells displayed a more potent osteo-chondro-progenitor cell population.

Following 6 days of pre-conditioning in CDM, the CD34+ cell population was separated and (FIG. 7a) the CD34+ cells displayed elevated expression of CD34 and (FIG. 7b) BMP-receptors. (FIG. 7c) Following 6 days of BMP-2 stimulation the CD34+ cells displayed elevated osteochondrogenic differentiation depicted by SOX9 and OSX expression. (FIG. 7d) Cluster analysis displayed correlation between the expression of CD34, BMP-receptors and differentiation markers. (FIG. 7e) A constellation plot displayed clear grouping of CD34$^+$ cells to the total cell population. The results are representative of two or more independent experiments.

FIGS. 8a-8g. The improved pre-conditioning effect was confirmed in young and adult donors.

(FIG. 8a) Pre-conditioning of individual donors (D1-3) and two different pools (P1-2) of cells of different gender and ages displayed elevated CD34 expression, (FIG. 8b) as well as adapted expression level of BMP type 1 and type 3 receptors. Expression of (FIG. 8c) SOX9, (FIG. 8d) OSX and (FIG. 8e): ID1 following BMP-2 stimulation. (FIG. 8f) Cluster correlation displayed association of pre-conditioning in CDM and expression levels of marker genes. (FIG. 8g) Constellation plot over the clustered data displayed grouping of the majority of CDM pre-conditioned cell populations over individual characteristics from the specific cell populations. The results are representative of two or more independent experiments.

Figure 9:
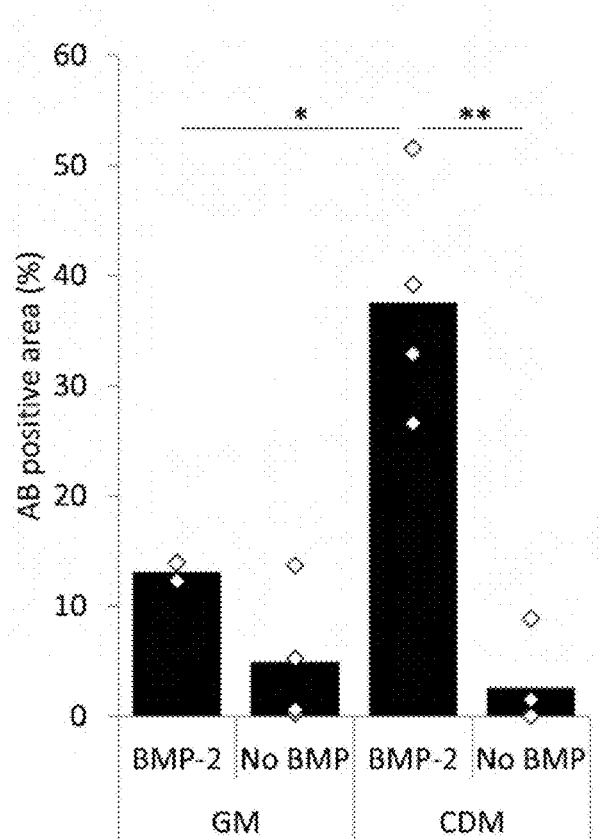

FIG. 9. In vitro BMP-2 stimulation of pre-conditioned hPDCs led to elevated in vivo cartilage formation.

In vitro pre-conditioning followed by BMP-2 stimulation and subsequent in vivo implantation leads to matrix formation. Upon quantification CDM pre-culture followed by BMP-2 stimulation leads to elevated cartilage formation.

FIGS. 10a and 10b. The number of cells per aggregate affected aggregate formation.

(FIG. 10a) Bright field images after 6 days of aggregation in cell densities of 50, 100 or 250 cells/aggregate in the presence of or without BMP-2 displayed stable formation of aggregates of 100 and 250 cells. (FIG. 10b) Aggregation induced a decrease in cell size after disassembly of the aggregates in the presence of or without BMP-2 stimulation. The results are representative of two or more independent experiments.

Figure 11:
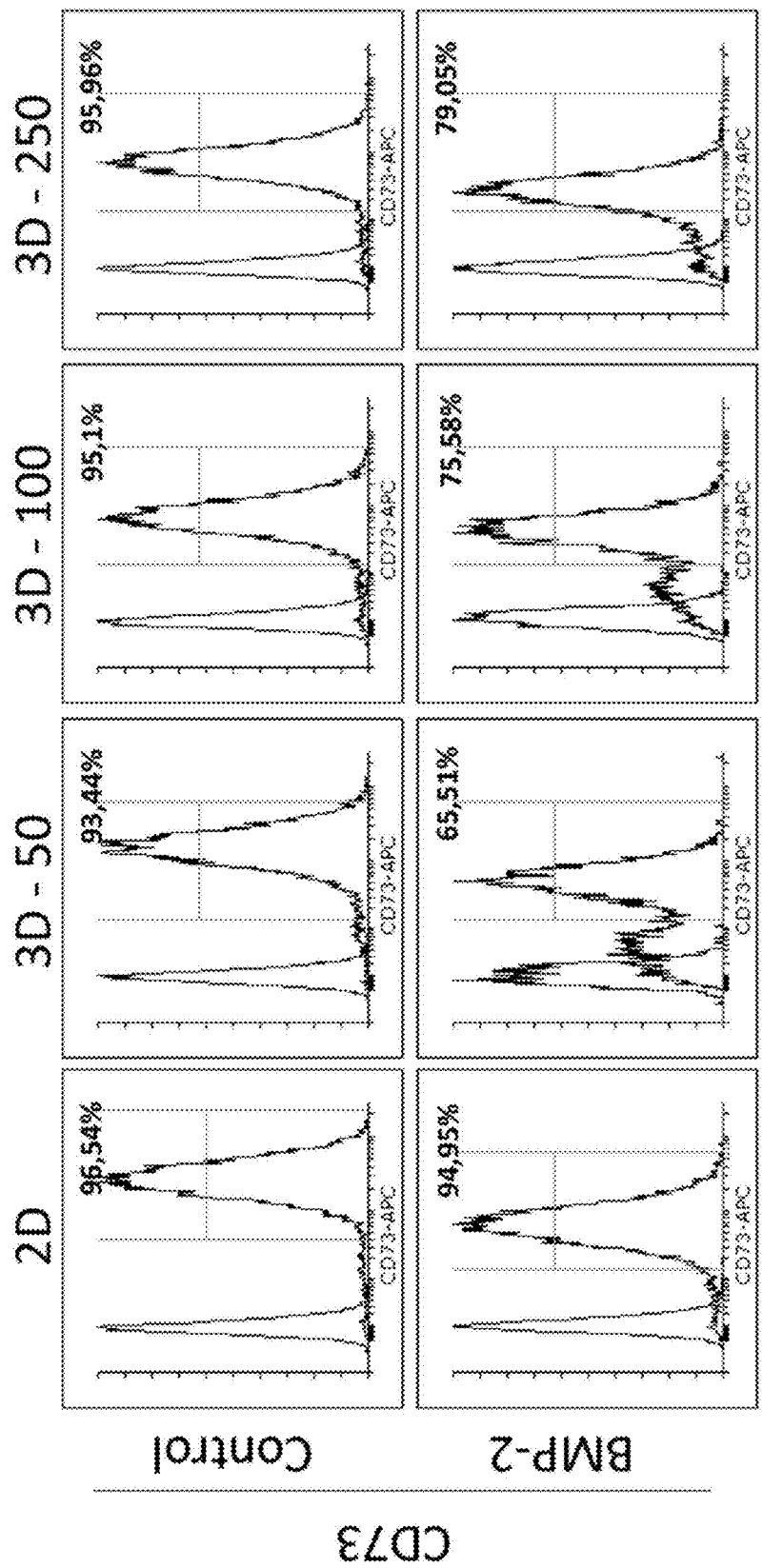
Figure 11:
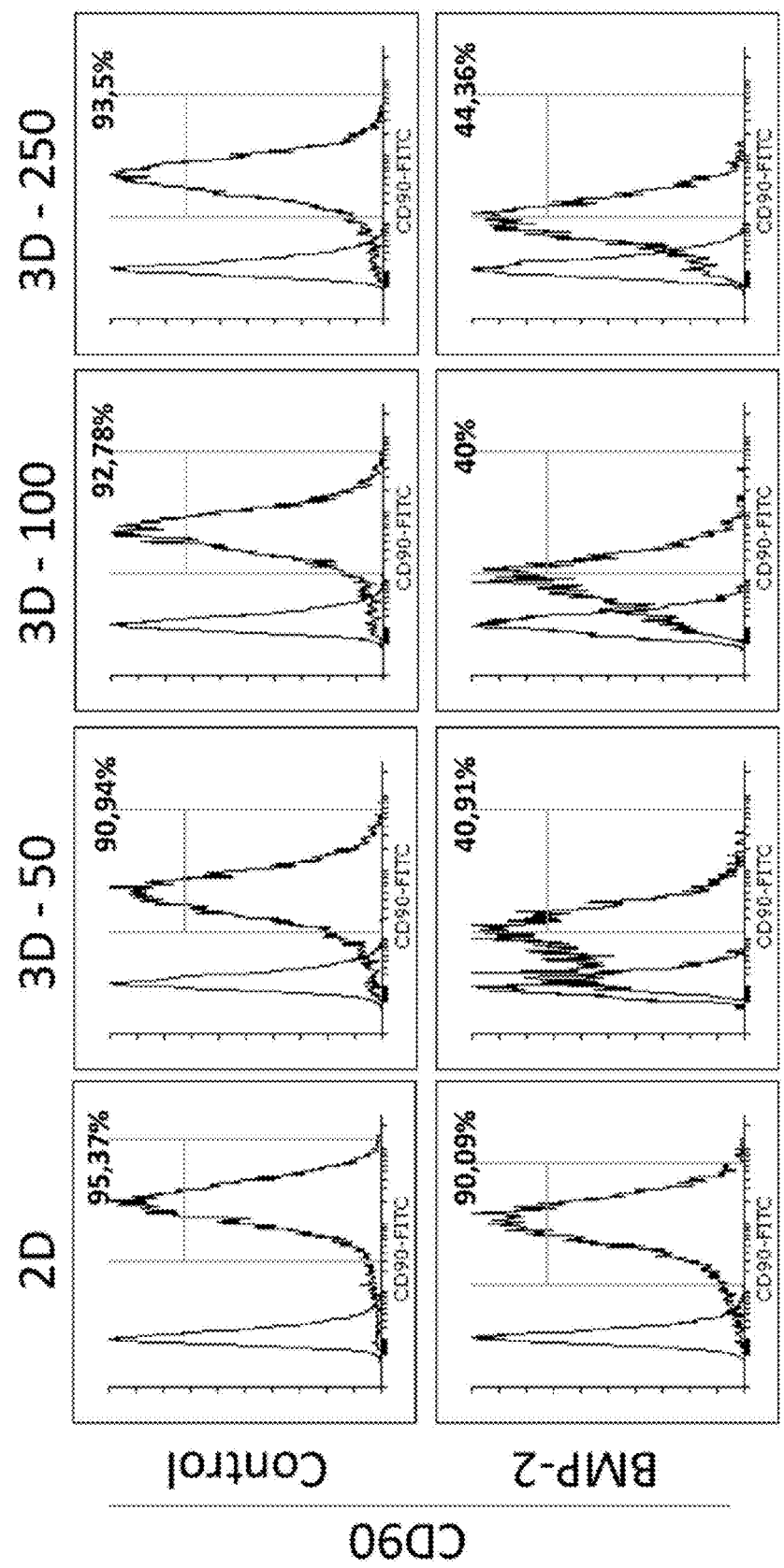
Figure 11:
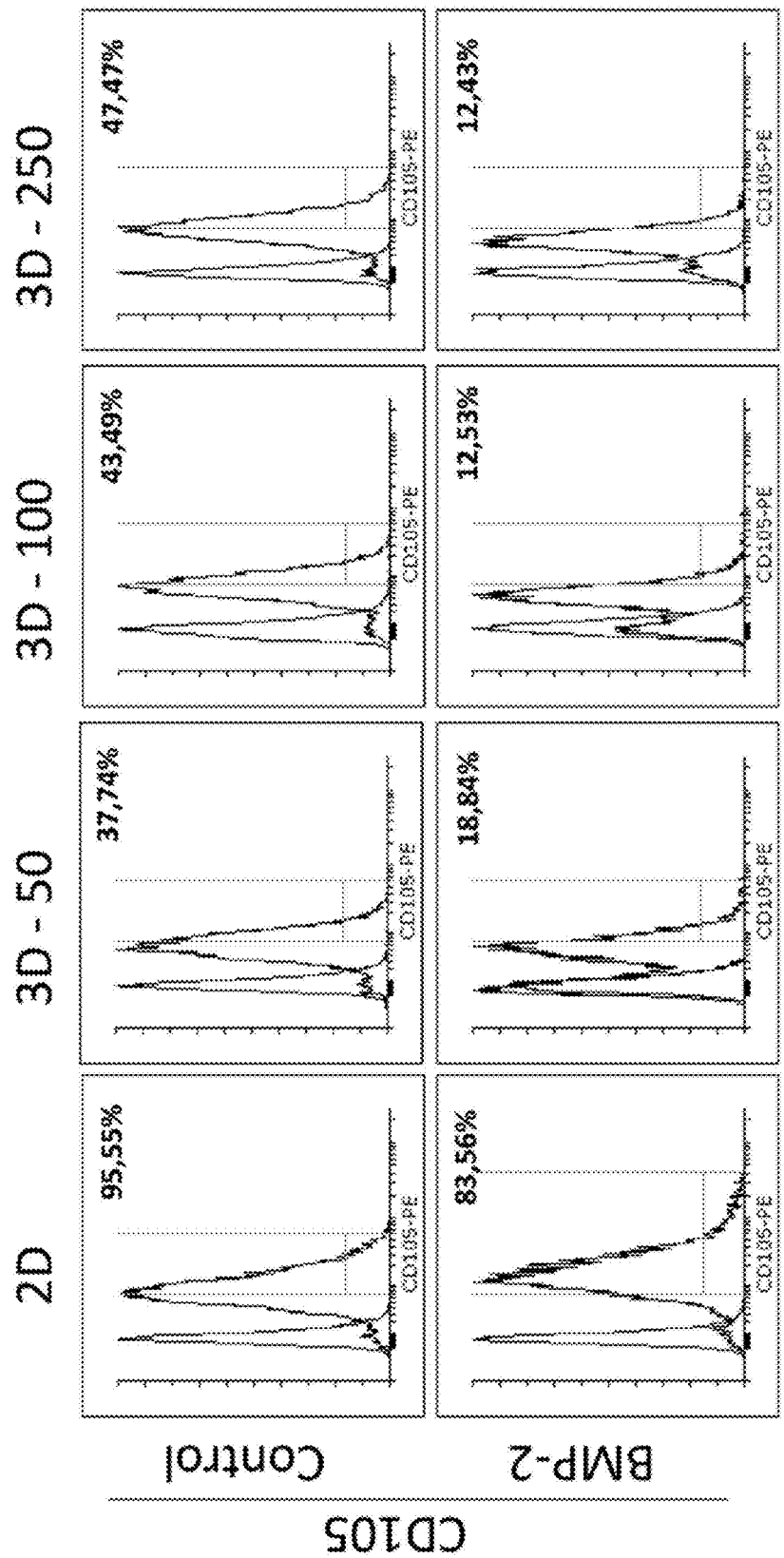

FIG. 11. Simultaneous aggregation and BMP-2 stimulation induce cell specification.

To determine the optimal size of the aggregate as an in vitro stimulated tissue for in vivo skeletal tissue repair we investigated aggregate sizes of 50, 100 and 250 cells/aggregate. Aggregation and BMP-2 induced shift in MSC marker expression of (FIG. 11(1)) CD73, (FIG. 11(2)) CD90, and (FIG. 11(3)) CD105 display a reduction when both factors are combined.

FIGS. 12a-12c. The number of cells per aggregate affected osteogenic and chondrogenic cell specification.

To determine the optimal size of the aggregate as an in vitro formed microtissue we investigated cellular phenotype after 6 days CDM pre-conditioning followed by 6 days of aggregation in sizes of 50, 100 and 250 cells/aggregate. mRNA transcript analysis of (FIG. 12a, inclusive of 12a(1)-12a(3)) chondrogenic, (FIG. 12b, inclusive of 12b(1)-12b(3)) osteogenic and (FIG. 12c, inclusive of 12c(1)-12c(3)) BMP-signalling and angiogenic markers display that both aggregation, aggregation size and BMP-2 stimulation affected cell differentiation. The results are representative of two or more independent experiments. (Statistical significance where: p<o: <0.05, oo: <0.01; or to control non BMP-stimulated conditions: *: <0.05, : <0.01, *: <0.001, or to BMP-2 2D condition: #: <0.05, ##: <0.01, ###: <0.001.

FIGS. 13a-13g. BMP-2 stimulation in combination with aggregation leads to elevated in vivo cartilage formation 1 week post implantation.

Figure 13B:
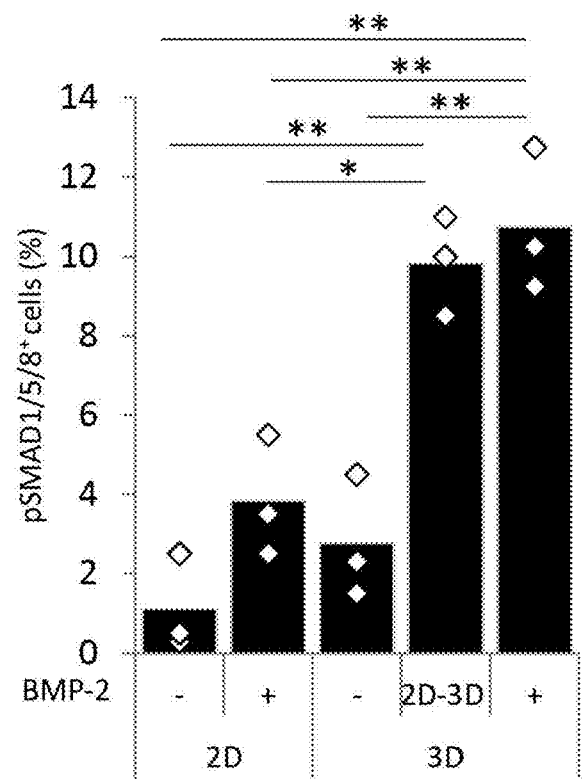
Figure 13C:
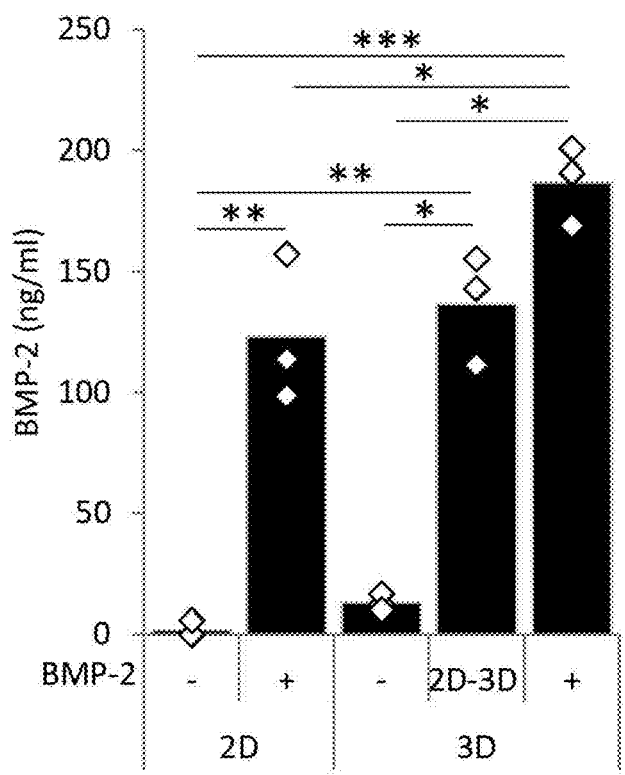
Figure 13D:
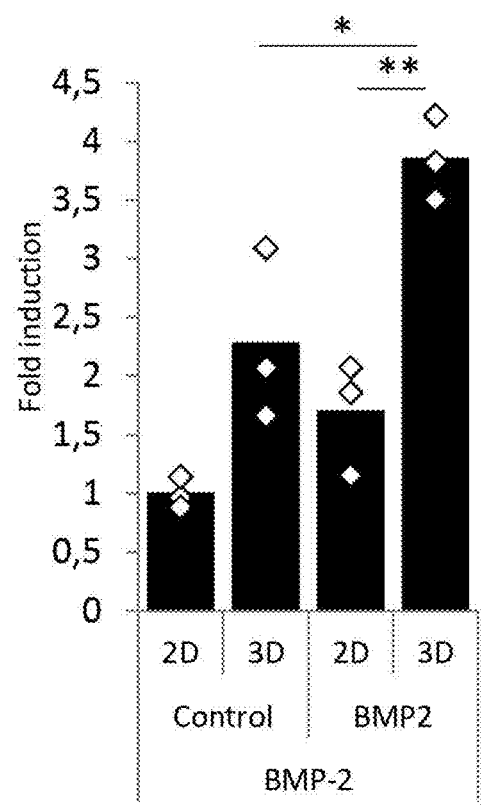

Histology and IHC on explanted constructs 1 and 3 weeks post in vivo implantation displayed that both BMP-2 stimulation and aggregation affected in vivo tissue formation. Quantification displayed that the combined stimulation of BMP-2 and aggregation elevated number of microvessels (FIG. 13a) and positive nuclei for pSmad1/5/8 (FIG. 13b). Upon BMP-2 quantification, the enhanced in vivo tissue formation and activated BMP-signalling was confirmed by BMP-2 production by stimulated cells in conditioned media (FIG. 13c). This was further confirmed by elevated expression of BMP-2 on mRNA level (FIG. 13d). (FIG. 13e) Quantified positive stained IHC for TRAP confirmed breakdown of GAG-rich areas, (FIG. 13f) quantified positive areas by IHC for S100 confirm more mature cartilage tissue in BMP-2 stimulated aggregates, (FIG. 13g) whereas quantified IHC for Ihh confirm the presence of hypertrophic chondrocytes.

Figure 14A:
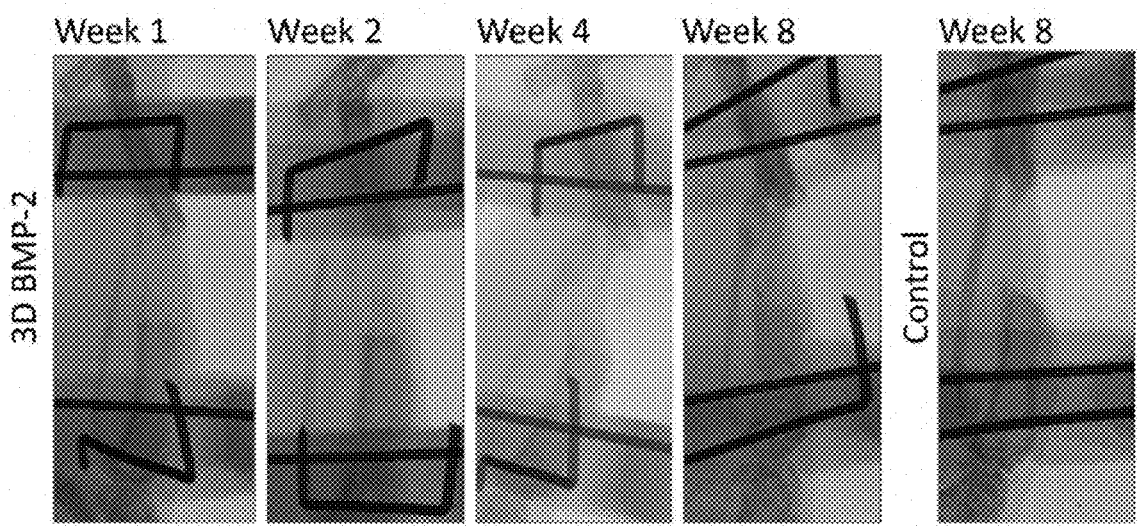
Figure 14B:
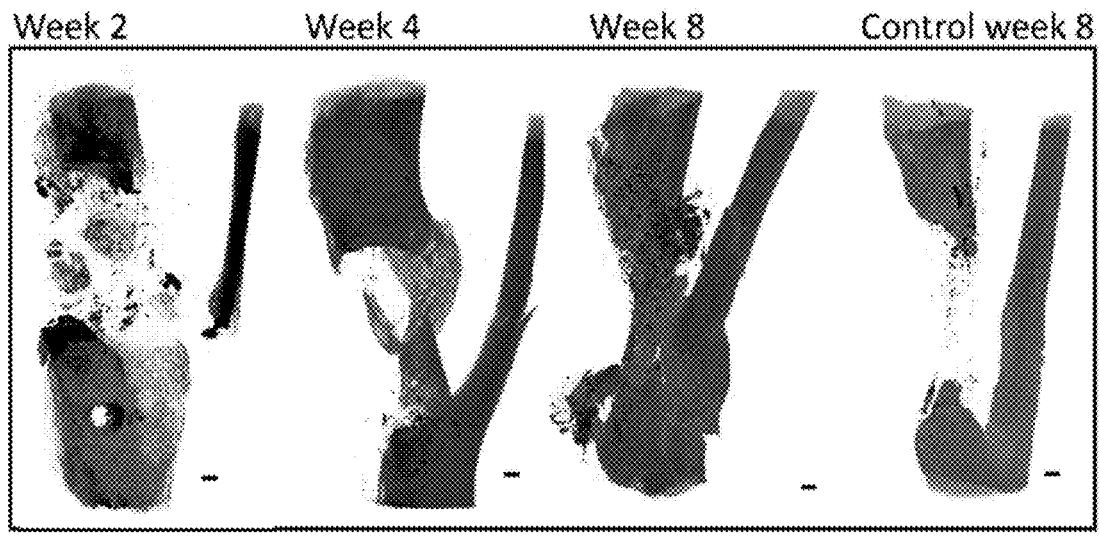

FIGS. 14a and 14b. The in vitro primed cell-based tissue construct led to the healing of a critical size long bone defect.

(FIG. 14a) In vivo x-ray monitoring of fracture healing upon transplantation of in vitro BMP-2 stimulated microaggregates. (FIG. 14b) Reconstructed images from nano-CT scanned explants displayed mineralized healing of the critical sized defect 4 weeks post transplantation.

FIGS. 15a-15d. Elevated in vivo bone formation by in vitro BMP-2 stimulated hPDCs under serum free conditions.

Figure 15A:
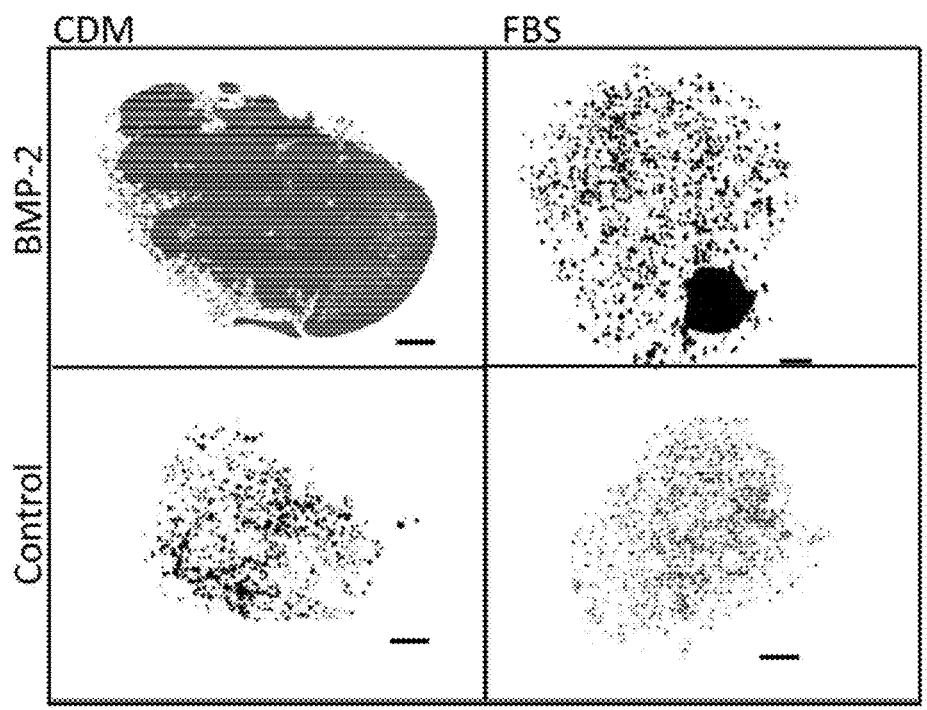
Figures 15B, 15C:
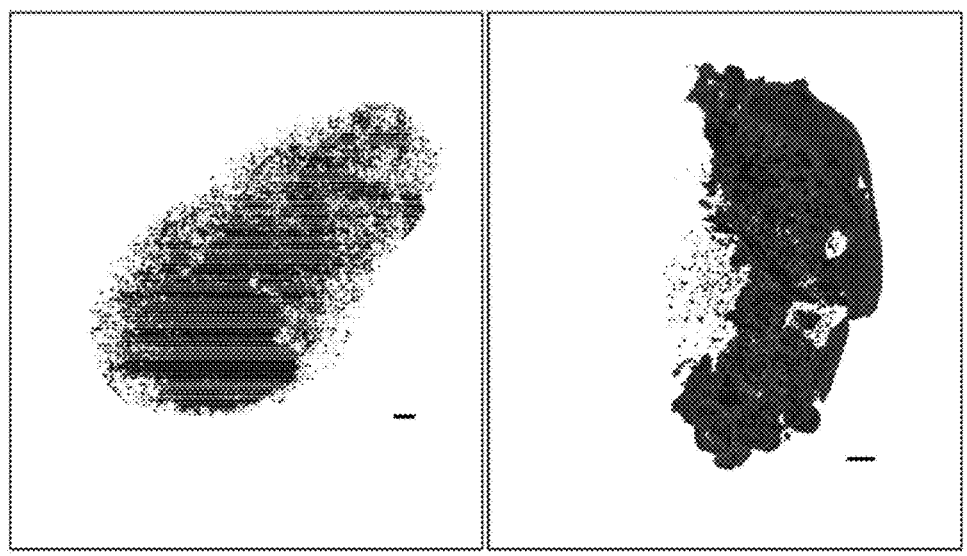
Figure 15D:
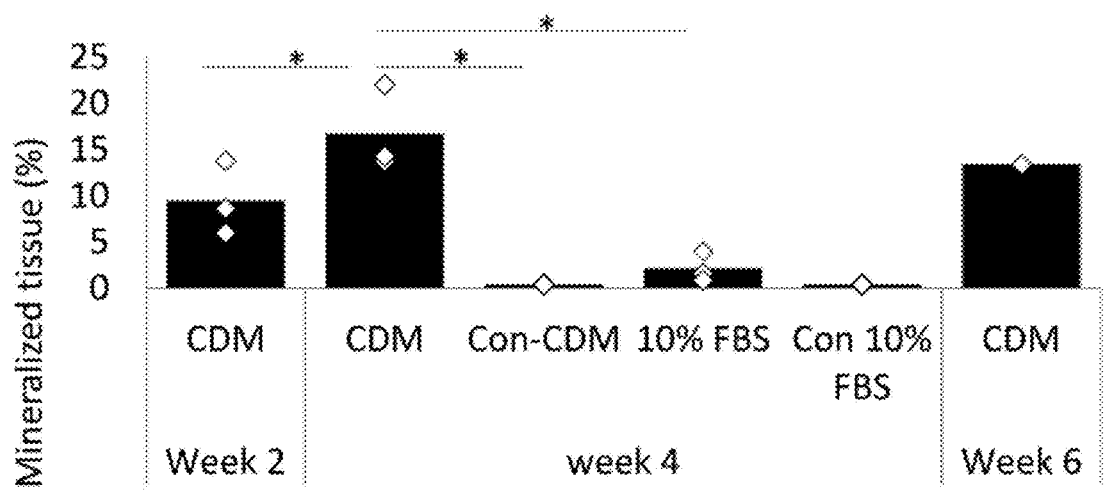

Upon in vivo implantation of in vitro BMP-2 stimulated hPDCs seeded onto CopiOs® scaffolds, constructs scanned by nano-CT for 3D visualization displayed mineralized tissue after 4 weeks of implantation, but not in non-stimulated controls where only scaffold remnants were seen (FIG. 15a). The mineralization in constructs containing serum free stimulated hPDCs had started at 2 weeks (FIG. 15b) whereas a more mineralized and dense tissue was seen in the same condition after 6 weeks (FIG. 15c). Quantification of mineralized tissue normalized to total explant volume (FIG. 15d).

DETAILED DESCRIPTION OF THE INVENTION

The present invention will be described with respect to particular embodiments but the invention is not limited thereto but only by the claims. Any reference signs in the claims shall not be construed as limiting the scope thereof.

One aspect of the present invention concerns an ATMP comprising cells, wherein the cells are stem cells, more preferably mesenchymal cells, such as periosteum derived cells. In a preferred embodiment, said cells are of mammalian in particular human origin.

Another aspect of the present invention concerns methods for producing an ATMP, comprising the culturing of cells, wherein said cells are stem cells, more preferably mesenchymal cells, such as periosteum derived cells. In a preferred embodiment, said cells are of mammalian in particular human origin.

One embodiment of the present invent relates to a method for producing an ATMP, more specifically an ATMP as further described in the present invention. An embodiment of the present invent relates to a general method for producing an ATMP comprising:
  (a) culturing stem cells in a serum free medium without BMP;
  (b) then the cells of step (a) are further cultured in aggregates;
  (c) then the cells of step (b) are further cultured in the presence of BMP; and
  (d) then the cells of step (c) are seeded to a biocompatible carrier.

In step (a) the term "without BMP" refers to said serum free medium that does not contain exogenous added BMP. During said culturing step (a), and also in step (b) and step (c), the stem cells themselves may produce BMP such that said medium may comprise endogenously produced BMP in said culturing steps. Thus in step (c) the term "are further cultured in the presence of BMP" means that (exogenous) BMP is added to the culture medium. Therefore, during step (c), at least exogenous BMP is present in the culture medium; said medium may further comprise endogenously produced BMP, wherein said endogenously produced BMP might be the same or different BMP as compared to the exogenous added BMP.

In a more specific embodiment of the present invention, including a more specific embodiment of said method, said stem cells are mesenchymal cells, such as periosteum derived cells, more specifically said cells are mammalian cells and even more specific, said cells are of human origin.

In a specific embodiment of the present invention, including a more specific embodiment of said method, said mesenchymal stem cells, such as periosteum derived cells, are characterized by their increased expression at the end of step (a) of at least one marker selected from the group consisting of CD34, FGF2, VEGF, MMP9, SOX9, CD200, ALK1, ALK2, ALK3, ALK6, BMPR2, AcvR2a and AcvR2b. In a more specific embodiment thereof, said mesenchymal stem cells, such as periosteum derived cells, are characterized by their increased expression at the end of step (a) of at least one, two, three or four markers selected from the group consisting of, SOX9, CD200, CD34, FGF2, VEGF and MMP9.

In another specific embodiment of the present invention, including a more specific embodiment of said method, said mesenchymal stem cells, such as periosteum derived cells, are characterized by their increased expression at the end of step (b) of at least one, two, three or four markers selected from the group consisting of SOX9, OSX, ID1, ACAN, OCN, DLX5, BMP-2, VEGF, COLL1, COLL2 and COLL10.

In a specific embodiment of the present invention, including a more specific embodiment of said method, said biocompatible carrier comprises collagen, calcium phosphate, carboxy methyl cellulose, a hydrogel or combinations thereof. In a more specific embodiment thereof, said biocompatible carrier is a calcium phosphate scaffold such as BioOss, Copios, Nuoss or Chronos. In another specific embodiment said biocompatible carrier is a hydrogel. In another specific embodiment said biocompatible carrier is a collagen-based scaffold. In another specific embodiment said biocompatible carrier is a carboxy methyl cellulose based scaffold.

In another specific embodiment of the present invention, including a more specific embodiment of said method, said cells are cultured in step (a) for at least 1 day and then further cultured in step (b) and (c) for at least 24 hours. Typically said culturing step (a) is about 3 to about 6 days, such as 3, 4, 5 or 6 days. Typically said culturing step (b) and (c) are between 1 to about 28 days, such as 1, 2, 3, 4, 5, 6, 7, 8, 9, 10, 11, 12, 13, 14, 15, 16, 17, 18, 19, 20, 21, 22, 23, 24, 25, 26, 27, 28 days, and more specifically said step (b) and (c) start simultaneously after step (a) and starting simultaneously includes starting on the same day or starting on the same day (within 24 hours) as step (a) ends. Starting simultaneously therefore also includes starting sequentially, such as step (c) immediately following step (b) and vice versa.

Suitable time-periods for culturing step (b) and (c) are between about 3 to about 6 days and typically said step (b) and step (c) start simultaneously. Selected time-periods for culturing step (b) and (c) are 3, 4, 5, or 6 days, including the simultaneously started step (b) and (c), such that the culturing steps in (b) and (c) are in total for example between 3 and 12 days, including 4, 5, 6, 7, 8, 9, 10, 11, 12 days. Typical total timing-values for said culturing steps (b) and (c) are about 6 days.

In a specific embodiment of the present invention, including a more specific embodiment of said method, said culturing step (a) is about 3 to about 6 days and said step (b) and (c) start simultaneously and are in total between 1 and about 28 days, more specifically are in total about 3 to about 6 days.

In a specific embodiment of the present invention, including a more specific embodiment of said method, said culturing step (b) is a culturing step in aggregates, meaning that said cells are further cultured under conditions that they form aggregates, meaning that they can form spontaneously or by manipulation (such as the method described in this invention, in the examples) aggregates of 1 to 5000 cells/aggregate. In a more specific embodiment said aggregates have a cell density of about 50, 100, or 250 cells/aggregate. Other methods of generating aggregates are well known to the skilled person. An example of such an aggregation method is described in Moreira Teixeira L. S. et al. (2012) *Eur. Cell Mater.* 23, 387-399.

In a specific embodiment of the present invention, including a more specific embodiment of said method, said BMP in step (c) is exogenously added BMP, and more specifically said BMP is selected from the group consisting of: BMP2, BMP4, BMP6, BMP7, BMP9, GDF5 (or BMP14, TGFβ, or any combinations thereof). In a more specific embodiment thereof said BMP is selected from the group consisting of: BMP2, BMP4, BMP6, BMP7, BMP9 and/or GDF5/BMP14. In another embodiment, said BMP is TGFβ1, TGFβ2 and/or TGFβ3. In a more specific embodiment thereof, said BMP is TGFβ3. In another specific embodiment, said BMP is BMP2 and/or BMP6.

In a more specific embodiment, said BMP in step (c) is used in a concentration of about 2 to 2000 ng/ml, more specifically said total BMP concentration is maximum 2000 ng/ml. Total concentration of maximum 2000 ng/ml is in the meaning of final concentration in the medium of BMP (including exogenous added BMP and endogenous produced BMP) that is not more than 2000 ng/ml. In a more specific embodiment thereof said BMP in step (c) is used in a concentration of about 2 to 1000 ng/ml, more specifically said concentration is about 100 ng/ml. Typical concentrations of exogenously added BMP in step (c) are 50 ng/ml, 100 ng/ml and 200 ng/ml. Typical examples of added BMP in step (c) are 200 ng/ml BMP2 and/or 200 ng/ml BMP6; 100 ng/ml BMP2; 100 ng/ml BMP6; and a combination of 100 ng/ml BMP2 and 100 ng/ml BMP6.

In a specific embodiment, said BMP in step (c) is BMP2 in about 100 ng/ml.

In another specific embodiment, said BMP in step (c) is BMP4 in about 100 ng/ml.

In another specific embodiment, said BMP in step (c) is BMP6 in about 100 ng/ml.

In another specific embodiment, said BMP in step (c) is BMP7 in about 100 ng/ml.

In another specific embodiment, said BMP in step (c) is BMP9 in about 100 ng/ml.

In another specific embodiment, said BMP in step (c) is BMP14 or GDF5 in about 100 ng/ml.

In another alternative embodiment, said BMP in step (c) is TGFβ, such as TGFβ3 in about 100 ng/ml.

In a specific embodiment of the present invention, including a more specific embodiment of said method, in the culturing step of said cells, more specific in step (c), at least one extra exogenous growth factor is added to said medium, preferably said at least one extra growth factor is selected from the group consisting of: TGFβ1, FGF2, GDF5 or any combination thereof. In a more specific embodiment thereof, said at least one extra growth factor is added such that the final concentration in the medium is about 0.01 ng/ml to about 100 ng/ml. In an even more specific embodiment thereof, said at least one extra growth factor is added such that the final concentration in the medium is about 0.01 ng/ml to about 10 ng/ml, and more specifically for TGFβ1 is about 0.1 ng/ml, for FGF2 is about 0.2 ng/ml, and for GDF5 is about 1 ng/ml. In a specific embodiment, said cells are cultured in step (c) with BMP together with the extra growth factors TGFβ1 at a concentration of about 0.1 ng/ml, FGF2 at a concentration of about 0.2 ng/ml, and GDF5 at a concentration of about 1 ng/ml; and more specifically wherein said BMP is a combination of BMP2 and BMP6 at a concentration of about 100 ng/ml for each BMP2 and BMP6.

In a specific embodiment of the present invention, including a more specific embodiment of said method, said cells at the end of step (c) are added to or seeded to a biocompatible carrier. Several methods of adding or seeding cells to said carriers or scaffolds are well known to the skilled person. An example of such a cell seeding on a (CaP comprising) scaffold is described in Eyckmans et al. (2010) *J Cell. Mol. Med.* 14, 1845-1856.

In a specific embodiment of the present invention, including a more specific embodiment of said method, said serum free medium comprises:

two basal cell culture media in a ratio of about 1:1 (v/v), such as Ham's F12 and DMEM Insulin, preferably at a concentration of about 6.25 µg/ml Transferrin, preferably at a concentration of about 6.25 µg/ml Selenium, preferably at a concentration of about 6.25 µg/ml α-ketoglutarate, preferably at a concentration of about $10^{-4}$ M Ceruloplasmin, preferably at a concentration of about 0.25 U/ml Cholesterol, preferably at a concentration of about 5 µg/ml Phosphatidyl ethanolamine, preferably at a concentration of about 2 µg/ml α-tochoferol acid succinate, preferably at a concentration of about $9 \times 10^{-7}$ M Reduced glutathione, preferably at a concentration of about 10 µg/ml Taurine, preferably at a concentration of about 1.25 µg/ml; and L-ascorbic acid 2-sulphate, preferably at a concentration of about 50 µg/ml.

In another embodiment thereof said medium further comprises triiodothyronine, and/or hydrocortisone, and/or parathyroid hormone, more specifically:

Triiodothyronine at a concentration of about $1.6 \times 10^{-9}$ M; and/or

Hydrocortisone at a concentration of about $1 \times 10^{-9}$ M; and/or parathyroid hormone at a concentration of about $5 \times 10^{-10}$ M.

Typically said serum free medium is a mixture of two basal cell culture media in a ratio of about 1:1 (v/v), such as Ham's F12 and DMEM, which further contains:

Insulin, preferably at a concentration of about 6.25 µg/ml

Transferrin, preferably at a concentration of about 6.25 µg/ml

Selenium, preferably at a concentration of about 6.25 µg/ml

α-ketoglutarate, preferably at a concentration of about $10^{-4}$ M

Ceruloplasmin, preferably at a concentration of about 0.25 U/ml

Cholesterol, preferably at a concentration of about 5 µg/ml

Phosphatidyl ethanolamine, preferably at a concentration of about 2 µg/ml

α-tochoferol acid succinate, preferably at a concentration of about $9\times10^{-4}$ M Reduced glutathione, preferably at a concentration of about 10 µg/ml Taurine, preferably at a concentration of about 1.25 µg/ml; and L-ascorbic acid 2-sulphate, preferably at a concentration of about 50 µg/ml.

In a specific embodiment of the present invention, including a more specific embodiment of said method, said serum free medium is a mixture of Ham's F12 and DMEM in a ratio of about 1:1 (v/v), which further contains the following compounds:

Insulin, preferably at a concentration of about 6.25 µg/ml

Transferrin, preferably at a concentration of about 6.25 µg/ml

Selenium, preferably at a concentration of about 6.25 µg/ml

α-ketoglutarate, preferably at a concentration of about $10^{-4}$ M

Ceruloplasmin, preferably at a concentration of about 0.25 U/ml

Cholesterol, preferably at a concentration of about 5 µg/ml

Phosphatidyl ethanolamine, preferably at a concentration of about 2 µg/ml

α-tochoferol acid succinate, preferably at a concentration of about $9\times10^{-7}$ M Reduced glutathione, preferably at a concentration of about 10 µg/ml Taurine, preferably at a concentration of about 1.25 µg/ml; and L-ascorbic acid 2-sulphate, preferably at a concentration of about 50 µg/ml.

Another aspect of the present invention relates to an ATMP produced by any of the methods of the present invention.

Another aspect of the present invention relates to a cellular composition comprising a serum free medium comprising at least one BMP and a biocompatible carrier with mesenchymal stem cells, such as periosteum derived cells, stimulated towards the osteochondral lineage, obtainable by the method of the present invention, said cellular composition being characterized in that the cells have an increased expression of at least one, two, three, or four markers selected from the group consisting of SOX9, OSX, ID1, ACAN, OCN, DLX5, BMP-2 VEGF, COLL1, COLL2 and COLL10.

Yet another aspect of the present invention relates to a pharmaceutical composition comprising: the ATMP according to the present invention and a pharmaceutically acceptable carrier, excipient or solution. A more specific embodiment of the present invention relates to a pharmaceutical composition comprising: the ATMP according to the present invention, and further comprising at least one extra exogenous BMP selected from the group consisting of BMP2, BMP4, BMP6, BMP7, BMP9, GDF5, or any combinations thereof and a pharmaceutically acceptable carrier, excipient or solution, wherein said extra endogenous BMP can be the same or a different BMP as the one used in culturing step (c). In a more specific embodiment thereof, said at least one extra exogenous BMP is one BMP that is different than the BMP used in in culturing step (c). In a more specific embodiment, said at least one extra exogenous BMP is added in a maximal concentration of 50 ng/mm³ biocompatible carrier.

One embodiment of the present invention relates the ATMP of the present invention for use as a medicine.

Another embodiment of the present invention relates the pharmaceutical composition of the present invention for use as a medicine.

More specific embodiments of the present invention relate to the ATMP or the pharmaceutical composition of the present invention for use as a medicine for the treatment of a subject or animal having a bone disorder, a cartilage disorder or a joint disorder. In a more specific embodiment thereof, said bone, cartilage or joint disorder is a bone fracture, a non-healing bone defect, an osteochondral defect or damaged joint surface, or a metabolic bone disease.

Typically said bone disorder is a non-healing bone defect. A specific embodiment of the present invention relates to the ATMP or the pharmaceutical composition of the present invention for use as a medicine for the treatment of a subject or animal having a non-healing bone defect, more specifically said subject is a mammal and even more specifically said mammal is a human patient.

Another aspect of the present invention relates to method of treatment of a bone, cartilage or joint disorder in an animal, comprising the administration to said animal of the ATMP or the pharmaceutical composition of the present invention.

In specific embodiments of the present invention said animal is a mammal. In more specific embodiments of the present invention said animal is a human patient.

One embodiment of the present invention concerns a method of treatment comprising administering an ATMP, which on itself comprises a therapeutically effective amount of the cells produced according to any one of the methods of this invention, to a subject with a bone disorder, said bone disorder includes a bone fracture. A preferred embodiment of the present invention relates to said method of treatment or the use of the ATMP to treat a subject, preferably a human, with a non-healing bone defect.

Alternatively, the present invention concerns the use of the ATMP produced according to any one of the methods of this invention or a pharmaceutical composition according to the present invention for use in medicine, more particularly for use in the treatment of a subject with a bone disorder. A more particular embodiment thereof relates to the treatment of a subject with a non-healing bone defect, more particularly said subject is a human patient.

In certain preferred embodiments, the subject, patient or animal is a human, more particularly a human with a bone defect, more particularly a non-healing bone defect.

Cell Culture.

In general, stem cells useful for the invention can be maintained and expanded in basal cell culture media that are available to and well-known in the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium® and RPMI-1640 Medium®. Many media are also available as low-glucose formulations, with or without sodium pyruvate. In a preferred embodiment, the stem cells are cultured in a mixture of 2 of said basal cell culture media (about 1:1, v/v). An example of said two basal media are Ham's F12 and DMEM, but the use of other combinations of said basal cell culture media are also contemplated in the present invention.

In more specific embodiments of the present invention the stem cells of the present invention are cultured in said basal cell culture media in serum-free conditions. In more specific embodiments thereof, said serum free cell culture conditions comprise the addition of the following compounds:
Insulin
Transferrin
Selenium
α-ketoglutarate
Ceruloplasmin
Cholesterol
Phosphatidyl ethanolamine
α-tochoferol acid succinate
Reduced glutathione
Taurine; and
L-ascorbic acid 2-sulphate More specifically, said compounds are in about the following concentrations in said basal culture media:
Insulin: 6.25 µg/ml
Transferrin: 6.25 µg/ml
Selenium: 6.25 µg/ml
α-ketoglutarate: $10^{-4}$ M
Ceruloplasmin: 0.25 U/ml
Cholesterol: 5 µg/ml
Phosphatidyl ethanolamine: 2 µg/ml
α-tochoferol acid succinate: $9 \times 10^{-7}$ M
Reduced glutathione: 10 µg/ml
Taurine 1.25 µg/ml; and
L-ascorbic acid 2-sulphate: 50 µg/ml In other embodiments, said serum free culture conditions further comprise: triiodothyronine, and/or hydrocortisone, and/or parathyroid hormone. More specifically the following concentrations in said basal culture media are for said additional compounds:
Triiodothyronine at about $1.6 \times 10^{-9}$ M; and/or
Hydrocortisone at about $1 \times 10^{-9}$ M; and/or
parathyroid hormone at about $5 \times 10^{-10}$ M More specifically, a serum free media useful for the culturing of the stem cells for the present invention is:
CDM, ie.:
Ham's F12 and DMEM (1:1) with the addition of:
insulin: 6.25 µg/ml;
Transferrin: 6.25 µg/ml;
Selenium: 6.25 µg/ml;
α-ketoglutarate: $10^{-4}$ M;
Ceruloplasmin: 0.25 U/ml;
Cholesterol: 5 µg/ml;
Phosphatidyl ethanolamine: 2 µg/ml;
α-tochoferol acid succinate: $9 \times 10^{-7}$ M;
Reduced glutathione: 10 µg/ml;
Taurine 1.25 µg/ml;
L-ascorbic acid 2-sulphate: 50 µg/ml;
Triiodothyronine: $1.6 \times 10^{-9}$ M;
Hydrocortisone: $1 \times 10^{-9}$ M; and
parathyroid hormone: $5 \times 10^{-10}$ M
wherein the concentrations of the compounds are the final concentrations in said medium.

A more preferred serum free medium, useful for the culturing of the stem cells of the present invention is "CDM Minimal",
which consist of:
Ham's F12 and DMEM (1:1) with the addition of:
insulin: 6.25 µg/ml
Transferrin: 6.25 µg/ml
Selenium: 6.25 µg/ml
α-ketoglutarate: $10^{-4}$ M
Ceruloplasmin: 0.25 U/ml
Cholesterol: 5 µg/ml
Phosphatidyl ethanolamine: 2 µg/ml
α-tochoferol acid succinate: $9 \times 10^{-7}$ M
Reduced glutathione: 10 µg/ml
Taurine 1.25 µg/ml; and
L-ascorbic acid 2-sulphate: 50 µg/ml
wherein the concentrations of the compounds are the final concentrations in said medium.

Another preferred serum free medium, useful for the culturing of the stem cells of the present invention is CDM Minimal with the addition of:
Triiodothyronine at about $1.6 \times 10^{-9}$ M; and/or
Hydrocortisone at about $1 \times 10^{-9}$ M; and/or
parathyroid hormone at about $5 \times 10^{-0}$ M
wherein the concentrations of the compounds are the final concentrations in said medium.

In an embodiment of the present invention, said serum free medium is CDM.

In an embodiment of the present invention, said serum free medium is CDM, wherein at least one factor is not present, said one factor that is not present is selected from the list consisting of: Triiodothyronine, Hydrocortisone and parathyroid hormone. Typical examples of said serum free media are CDM Minimal, CDM without Hydrocortisone and parathyroid hormone, CDM without Triiodothyronine and Hydrocortisone, CDM without Triiodothyronine and parathyroid hormone, CDM without Triiodothyronine, CDM without Hydrocortisone and CDM without parathyroid hormone.

In another embodiment of the present invention, said serum free medium is CDM. Minimal with the addition of Triiodothyronine at $1.6 \times 10^{-9}$ M (final concentration in said medium).

It is known to the skilled person that the concentrations of the compounds in said serum free media can be varied, maximum by 1 log scale, preferably by less than 50% or more preferably less than 20% or less than 10%. By way of example the α-ketoglutarate concentration in that medium can be between 10-5 M and $10^{-3}$ M, preferably between $1.5 \times 10^{-4}$ M and $0.5 \times 10^{-4}$ M, or more preferably between $1.2 \times 10^{-4}$ M and $0.8 \times 10^{-4}$ M or between $1.1 \times 10^{-4}$ M and $0.9 \times 10^{-4}$ M. As specified herein said basal medium can be any basal medium as contemplated by the description of the present invention, including other mixes of 2 basal media as compared to Ham's F12 and DMEM (1:1, v/v).

Definitions

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform in the disclosed invention. As an example, in case the term about is used in combination with a certain amount of days, it includes said specific amount of days plus or minus 1 day, eg. about 6 days, including any amount of days between 5 and 7. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The term "animal", "patient" or "subject" is used herein to describe an animal, especially including a domesticated mammal and preferably a human, to whom a treatment or procedure is performed. For treatment of those conditions or disease states which are specific for a specific animal such as a human patient, the term patient refers to that specific animal. In most instances, the patient or subject of the present invention is a domesticated/agricultural animal or human patient of either gender.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. "Preventing" also encompasses preventing the recurrence or relapse-prevention of a disease or disorder for instance after a period of improvement.

A 'therapeutic amount' or 'therapeutically effective amount' as used herein refers to the amount of an active compound or pharmaceutical agent (e.g., a cell-based product) effective to treat a disease or disorder in a subject, i.e., to obtain a desired local or systemic effect. The term thus refers to the quantity of the cells, the compound or the agent that elicits the biological or medicinal response in a tissue, system, animal, or human that is being sought by a researcher, veterinarian, medical doctor or other clinician. Such amount will typically depend on the specific cell type, the compound or the agent and the severity of the disease, but can be decided by the skilled person, possibly through routine experimentation. The term "prophylactically effective amount" refers to an amount of cells, an active compound or pharmaceutical agent (e.g., a cell-based product) that inhibits or delays in a subject the onset of a disorder as being sought by a researcher, veterinarian, medical doctor or other clinician.

As used herein, a "biocompatible" carrier or material is a synthetic or natural material used to replace part of a living system or to function in intimate contact with living tissue. Biocompatible materials are intended to interface with biological systems to evaluate, treat, augment or replace any tissue, organ or function of the body. The biocompatible material has the ability to perform with an appropriate host response in a specific application and does not have toxic or injurious effects on biological systems. Non-limiting examples of biocompatible materials include a biocompatible ceramic, a biocompatible polymer or a biocompatible hydrogel. Biocompatible materials include also "biodegradable" materials meaning that that material, once implanted into a host, will begin to degrade. Biocompatible carriers or materials also include synthesized materials that resemble a substance that occurs naturally in a human body and which is not substantially rejected by (e.g., does not cause an unacceptable adverse reaction in) the human body. When used in connection with tissue scaffolds, said biocompatible material means that the scaffold is substantially biologically inert (i.e., will not cause an unacceptable immune response/rejection) and is designed to resemble a structure (e.g., a bone/tissue anatomy) that occurs naturally in a mammalian, e.g., human, body and that promotes healing when implanted into the body. Non-limiting examples of biocompatible carriers useful for the ATMPs and methods of the present invention are collagen comprising carriers, carboxymethyl comprising carriers, and calciumphosphate (CaP) comprising carriers, such as BioOss®, CopiOs®, NuOss™, chronOS®, ReproBone™, IntegraMozaic™.

"ATMP" stands for Advanced Therapeutic Medicinal Products which is a term used in the field of registration where it refers to a medicine for human use that is based on genes, cells or tissue engineering. In the context of the present invention it relates more specifically to a biocompatible carrier comprising bone forming and/or cartilage forming cells.

As used herein, "synthetic" shall mean that the material or carrier is not of a human or animal origin.

As used herein and unless otherwise stated, the term "mesenchymal cells" means any cell type derived from tissues originating from the mesoderm or neural crest during embryonic development or have the phenotype as described in Dominici et al. (Dominici 2006, Cytotherapy, 8, 315-17).

As used herein and unless otherwise stated, the term "periosteum derived cells" means any cell type that is isolated from the periosteum well known to a person skilled in the art.

As used herein and unless otherwise stated, the term "cells that express a primitive mesenchymal phenotype" means any cell type originating from the mesoderm or neural crest during embryonic development or derived from stem cell differentiation or (partial) dedifferentiation such as by the IPS technology, well known to the skilled person, and which will give rise to cells that contribute to all mesenchymal tissues as known to a person skilled in the art. These primitive cells may express markers that upon genetic labeling at the moment of expression, can be found in any mesenchymal tissue at later stages of development. Examples of such markers include but are not limited to PRX1, PRX2, and Sox9.

As used herein and unless otherwise stated, the term "BMP" or "bone morphogenetic protein" refers to any member of a particular subclass (i.e. the BMP family) of the transforming growth factor-β (TGF-β) super family of proteins (see, e.g., Hoffmann et al., Appl. Microbiol Biotechnol, 57: 294-308 (2001); Reddi, J. Bone joint Surg., 83-A(Supp. 1): S1-S6 (2001); U.S. Pat. Nos. 4,968,590; 5,011,691; 5,674,844; 6,333,312). All such BMPs have a signal peptide, prodomain, and a carboxy-terminal (mature) domain. The carboxy-terminal domain is the mature form of the BMP monomer and contains a highly conserved region characterized by seven cysteines that form a cysteine knot (Griffith et al., Proc. Natl. Acad. ScL USA., 93: 878-883 (1996)). In certain embodiments of the present invention a BMP can be an alternative BMP, ie. a TGFβ such as TGFβ1, TGFβ2 or TGFβ3, especially in those embodiments where cartilage defects or cartilage diseases are envisaged to treat with said specific alternative ATMPs.

BMPs were originally isolated from mammalian bone using protein purification methods (see, e.g. Urist et al., Proc. Soc. Exp. Biol, Med., 173: 194-199 (1983); Urist et al., Proc. Natil. Acad, ScL USA, 81: 371-375 (1984); Sampath et al., Proc. Natl. Acad. ScL USA, 84: 7109-7113 (1987); U.S. Pat. No. 5,496,552). However, BMPs have also been detected in or isolated from other mammalian tissues and organ including kidney, liver, lung, brain, muscle, teeth, and gut. BMPs may also be produced using standard in vitro recombinant DNA technology for expression in prokaryotic or eukaryotic cell cultures (see, e.g., Wang et al., *Proc. Natl. Acad. ScL USA,* 87: 2220-2224 (1990); Wozney et al., *Science,* 242: 1528-1534 (1988)). Some BMPs are commercially available for local use as well (e.g., BMP-7 is manufactured and distributed by Stryker-Biotech (Hopkinton, Mass., U.S.); BMP-2 is manufactured and distributed by Wyeth (Madison, N.J., U.S.), and also by Medtronic, Inc., Minneapolis, Minn., U.S.).

BMPs normally exist as diners of the same monomeric polypeptides (homodiners) held together by hydrophobic interactions and at least one interchain (between monomers) disulfide bond. However, BMPs may also form heterodimers by combining the monomers of different degrees (lengths) of processing (e.g., a full-length, unprocessed monomer associated with a processed, mature monomer) or monomers from different BMPs (e.g., a BMP-6 monomer associated with a BMP-7 monomer). A BMP dimer of unprocessed monomers or a BMP heterodimer of one processed BMP monomer and one unprocessed BMP monomer are typically soluble in aqueous solutions, whereas a BMP homodimer comprised of two fully processed (mature) monomers is only soluble in an aqueous solution at a low pH (e.g., acetate buffer, pH 4.5) (see, e.g., Jones et al., Growth Factors, 11: 215-225 (1994)). BMPs useful in the ATMPs, compositions and methods described herein, preferably for treatment of bone disorders, are those that have osteogenic activity, i.e., the ability to initiate/stimulate bone formation. Osteogenic (or "osteoinductive") activity may be detected using any of a variety of standard assays. Such osteogenic assays include ectopic bone formation assays in which a carrier matrix coated with a BMP, seeded or non-seeded with osteoprogenitor cells are implanted at an ectopic site in a rodent, and the implant then monitored for bone formation (Sampath and Reddi, Proc. Natl. Acad. Sci USA, 78: 7599-7603 (1981)). In a variation of such an assay, the matrix maybe implanted at an ectopic site and the BMP administered to the site, by injection. Another way to assay for BMP osteogenic activity is to incubate cultured fibroblast progenitor cells with a BMP and then monitor the cells for differentiation into chondrocytes and/or osteoblasts (see, e.g., Asahina et al., Exp. Cell. Res., 222: 38-47 (1996)). BMPs that have osteogenic activity and that are therefore useful in the ATMPs, compositions and methods described herein include, but are not limited to, BMP-2, BMP-4, BMP-6, BMP-7, BMP-9, BMP-14 or GDF5, and heterodimers thereof, whether purified from a natural source, produced recombinantly by eukaryotic (e.g., mammalian, yeasts, insects, fish) or prokaryotic (e.g., bacterial) cells, or produced in whole or in part by in vitro protein synthesis methods. It is also understood that ATMPs, compositions and methods as described herein may alternatively comprise an osteogenic protein other than a member of the osteogenic BMP family described above provided such osteogenic protein is functionally equivalent to a BMP in that the protein has osteogenic activity as demonstrated in a standard osteogenic assay, such as an ectopic bone formation assay described above. Functionally equivalent proteins may include various osteogenic BMP homologues, i.e., osteogenic proteins that have an amino acid sequence that is homologous to a known osteogenic BMP (e.g., about 80% 90%, 95 or more homologous to a known osteogenic protein, such as for example a BMP-variant, more specifically a BMP6-variant, in which modification of at least one amino acid increases the proteins' solubility, hence its efficacy in inducing osteogenic cell differentiation). Such BMP homologues or BMP variants may be naturally occurring, recombinantly produced, or synthetically produced in whole or in part (see, e.g., U.S. Pat. No. 6,333,312).

Alternative BMPs useful in the ATMPs, compositions and methods described herein, preferably for treatment of cartilage disorders, are TGFβs, such as TGFβ1, TGFβ2, and TGFβ3.

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has dedifferentiated, for example, by nuclear transfer, by fusions with a more primitive stem cell, by introduction of specific transcription factors, or by culture under specific conditions. See, for example, Wilmut et al., Nature, 385: 810-813 (1997); Ying et al., Nature, 416:545-548 (2002); Guan et al., Nature, 440:1199-1203 (2006); Takahashi et al., Cell, 126:663-676 (2006); Okita et al., Nature, 448:313-317 (2007); and Takahashi et al., Cell, 131:861-872 (2007).

As used herein, the term "SFM" refers to the chemically defined media as presented in Harrisson et al., 1991 and US20010039050.

As used herein, the term BMP-Technology Medium or "CDM" is a serum free medium which consists of:
Ham's F12 and DMEM (1:1, v/v) with the addition of:
insulin: 6.25 µg/ml;
Transferrin: 6.25 µg/ml;
Selenium: 6.25 µg/ml;
α-ketoglutarate: $10^{-4}$ M;
Ceruloplasmin: 0.25 U/ml;
Cholesterol: 5 µg/ml;
Phosphatidyl ethanolamine: 2 µg/ml;
α-tochoferol acid succinate: $9 \times 10^{-7}$ M;
Reduced glutathione: 10 µg/ml;

Taurine 1.25 µg/ml;
L-ascorbic acid 2-sulphate: 50 µg/ml;
Triiodothyronine: $1.6 \times 10^{-9}$ M;
Hydrocortisone: $1 \times 10^{-9}$ M; and
parathyroid hormone: $5 \times 10^{-10}$ M
wherein the concentrations of the compounds are the final concentrations in said medium.

As used herein and unless otherwise stated, the term "bone disorders" or "bone diseases" means any medical condition that affects the bone, examples of such bone disorders include but are not limited to bone diseases such as osteoporosis, Paget's disease, congenital pseudoarthrosis, osteoarthritis, osteosarcoma, diabetes, osteopetrosis, brittle bone disease, McCune-Albright Syndrome and Neurofibramatosis and also include bone injuries such as bone fractures, delayed union fractures and non-healing bone disorders.

As used herein and unless otherwise stated, the term "non-healing bone defect" or "non-healing bone disorder" or "nonunion bone defects" means permanent failing of healing of a structural defect of the bone leading to loss of integrity. Examples of such non-union bone defects include but are not limited to atrophic, hypertrophic fractures and large bone defects as known to a person skilled in the art.

As used herein, the terms "cartilage disorder" or "cartilage disease" or "joint disorder" or "joint disease refer to developed or genetic inherited disorders of cartilage and/or joints such as spondylo-, ankelo- and osteoarthritis.

As used herein, the terms "aggregates" or "microaggregates" refer to cells that condense together, spontaneously or by manipulation (such as described in the example section and detailed description in Materials and Methods), to aggregates of 1 to 5000 cells/aggregate. Individual aggregates can then be combined, 1 to $>1*10^{10}$ to custom size, depending of defect size. Typical amounts of cells per aggregate are about 50, about 100, about 150, about 200 or about 250 cells per aggregate. Other methods of generating aggregates or microaggregates are well known to the skilled person. An example of such an (micro)aggregation method is described in Moreira Teixeira et al. 2012, cited above. For a large defect of 3-4 cm one would need about 400 million cells. For treatments using aggregates of cells one may need somewhat less cells, eg, with aggregates of about 250 cells per aggregate, one would need about 1 million aggregates for such large bone defects.

Unless defined otherwise, all technical and scientific terms used herein have the same meaning as commonly understood by one of ordinary skill in the art in the field of the invention. Any methods and materials similar or equivalent to those described herein can also be used in the practice or the present invention, but the preferred methods and products are described herein.

Examples

Development of a Cell Base Translational Approach Based on BMP-Technology.

1.1 Serum Affects hPDC Proliferation and BMP-2 Induced Differentiation.

1.1.1 Serum Level Affects Proliferation in hPDCs.

Figure 1B:
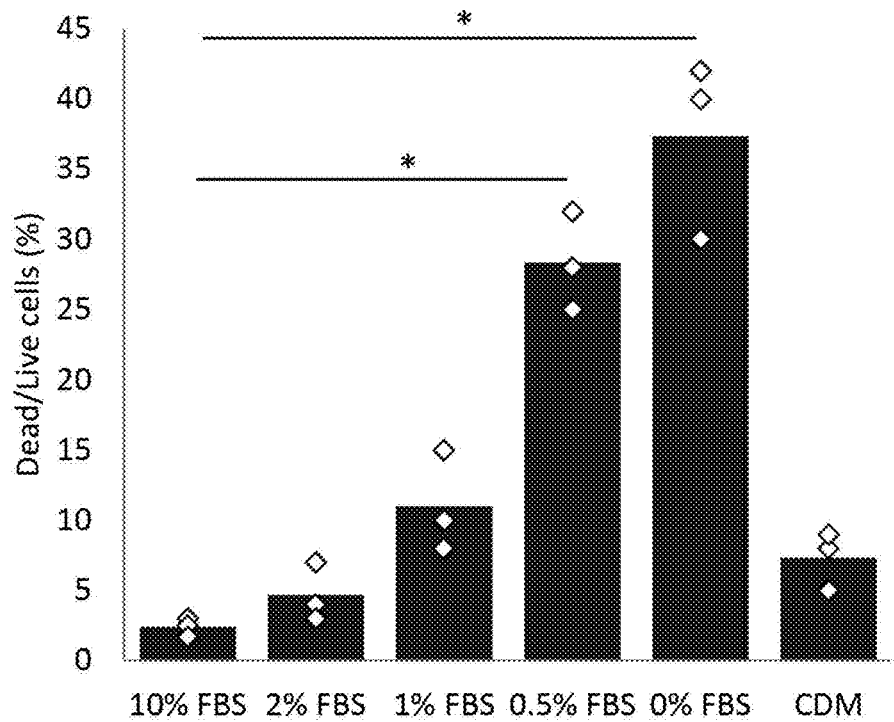

To assess the effect of different serum levels on cell viability and proliferation, we measured DNA content in hPDCs for 21 days. After 24 h, cells cultured in 1% FBS or less already displayed a significant reduction in DNA content as compared to cells cultured in 10% FBS, FIG. 1a. This trend was maintained and further elevated during the culture period. Live/dead staining in cells cultured for 3 days displayed higher fraction of dead cells in media containing 0% FBS, FIG. 1b. Cell morphology in the same condition displayed morphological differences depicted by less elongated cells. Cells cultured in CDM displayed similar viability to cells cultured in 1% FBS, however, cell morphology was similar to cells cultured in media containing 10% FBS. This trend was further elevated throughout the culture period. Therefore, media containing 1% FBS along with CDM were selected for further studies as promising media conditions for BMP-technology, while media with 10% FBS was selected as the control condition.

1.1.2 BMP-2 Induced Proliferation and ALP-Activity.

Figure 1C:
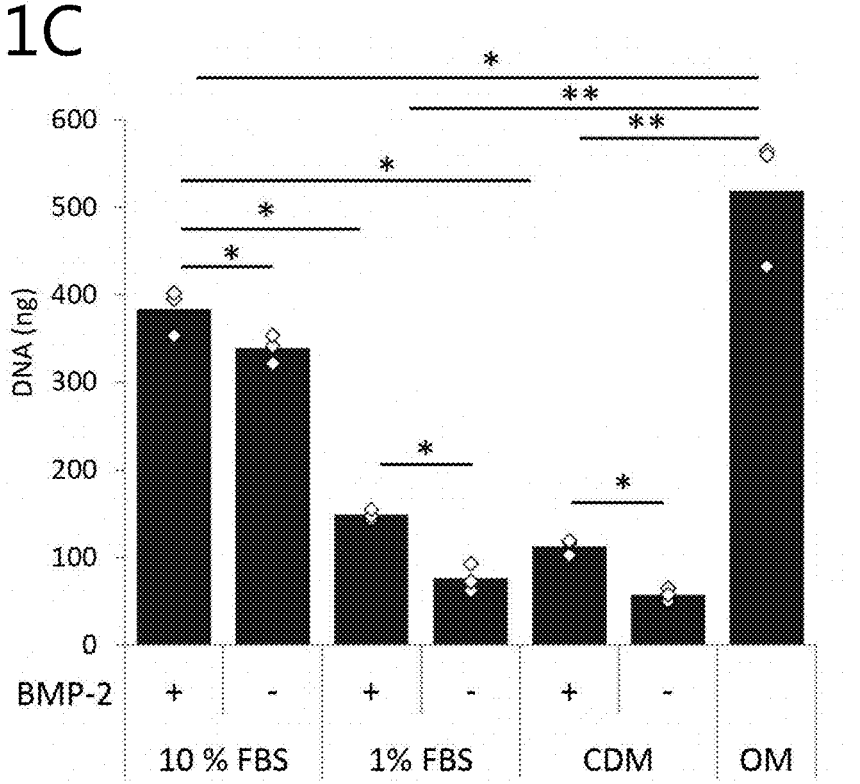
Figure 1D:
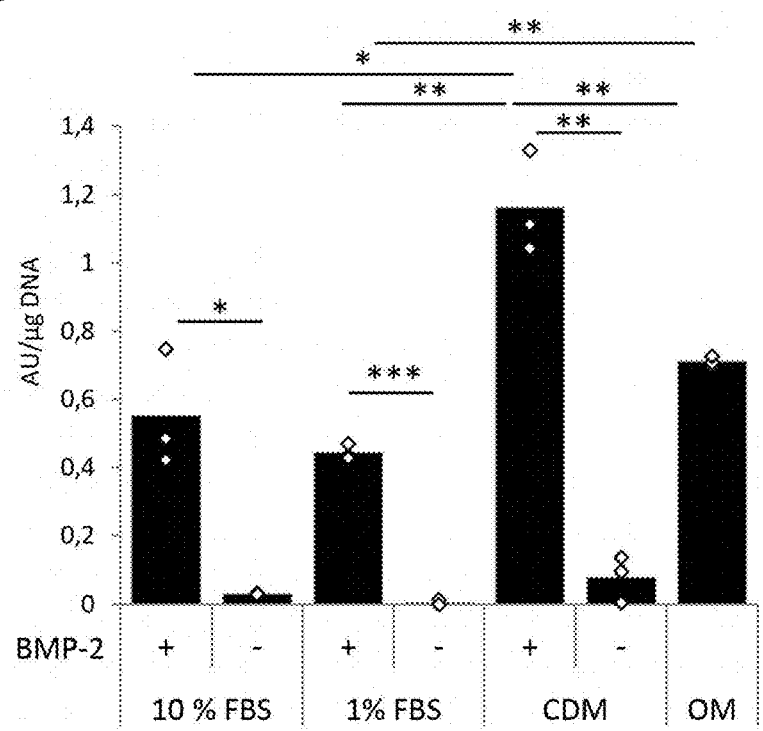

After 6 days of stimulation in BMP-2-supplemented CDM or media containing 1% or 10% FBS, a difference in cell morphology could be seen. In BMP-2 supplemented media containing FBS, flat cells were detected in combination with cellular condensations. Cells cultured in BMP-2 supplemented CDM displayed a more polygonal cell shape together with mineralisation areas throughout the culture plate (black arrows). In all BMP-2 supplemented conditions, higher confluency could be seen, indicating a proliferative effect by the addition of BMP-2. This was confirmed by an elevated DNA content observed in all media conditions supplemented with BMP-2, compared to non-supplemented conditions, FIG. 1c. In BMP-2 supplemented media a 1.2-, 2- and 3-fold elevated DNA content could be seen in media containing 0% FBS, 1% FBS and CDM, respectively. Furthermore, BMP-2 stimulation induced elevated ALP-activity in all media conditions, an in vitro marker for osteogenesis, FIG. 1d. A 6-, 4- and 8.5-fold elevated ALP activity was seen in cell stimulated with BMP-2 supplemented media containing 10%-, 1%- or CDM, respectively. Moreover, stimulation of hPDCs in BMP-2 supplemented CDM induced a 2-fold higher activity as compared to serum containing conditions.

Figure 1E:
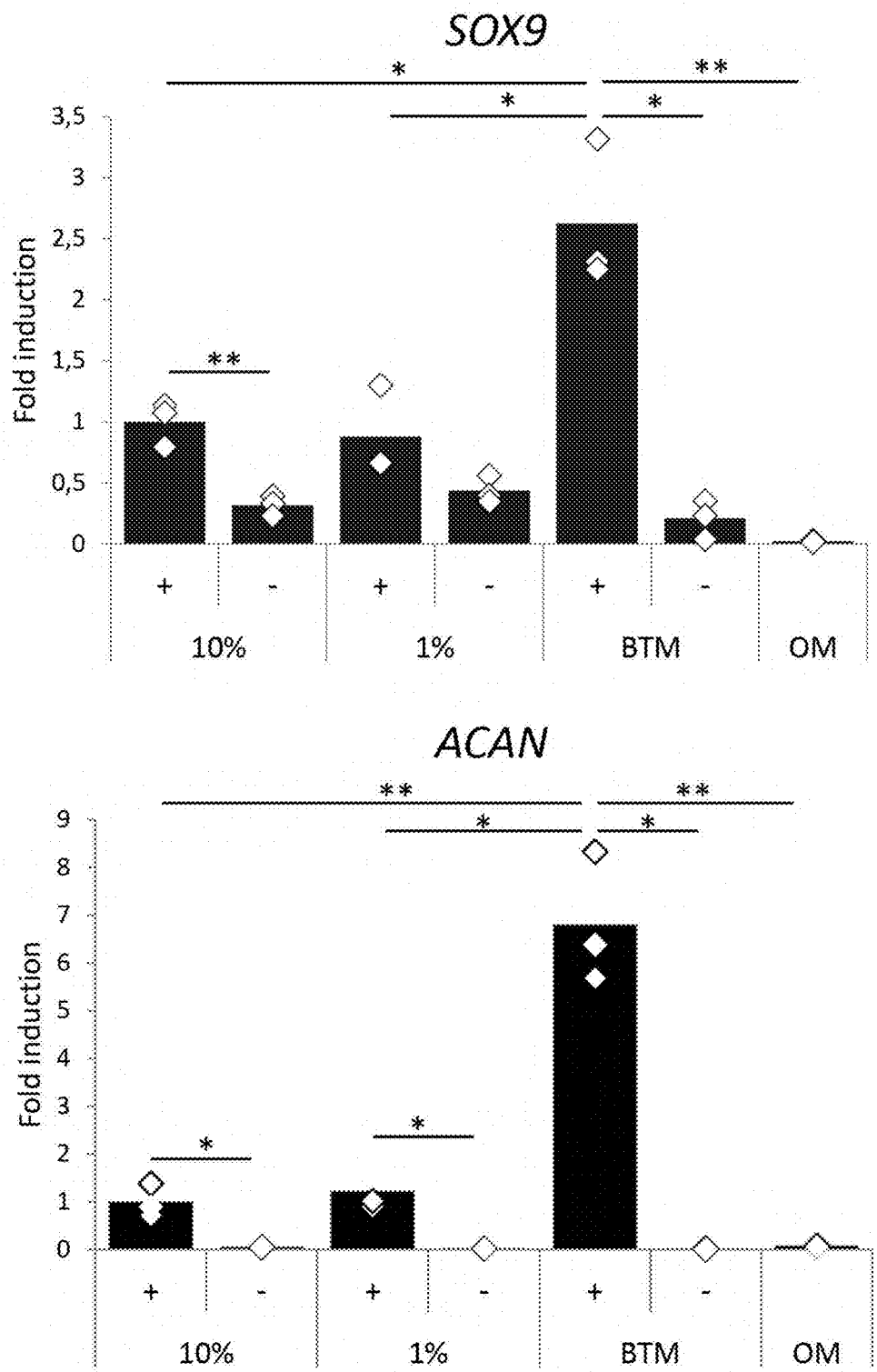
Figure 1F:
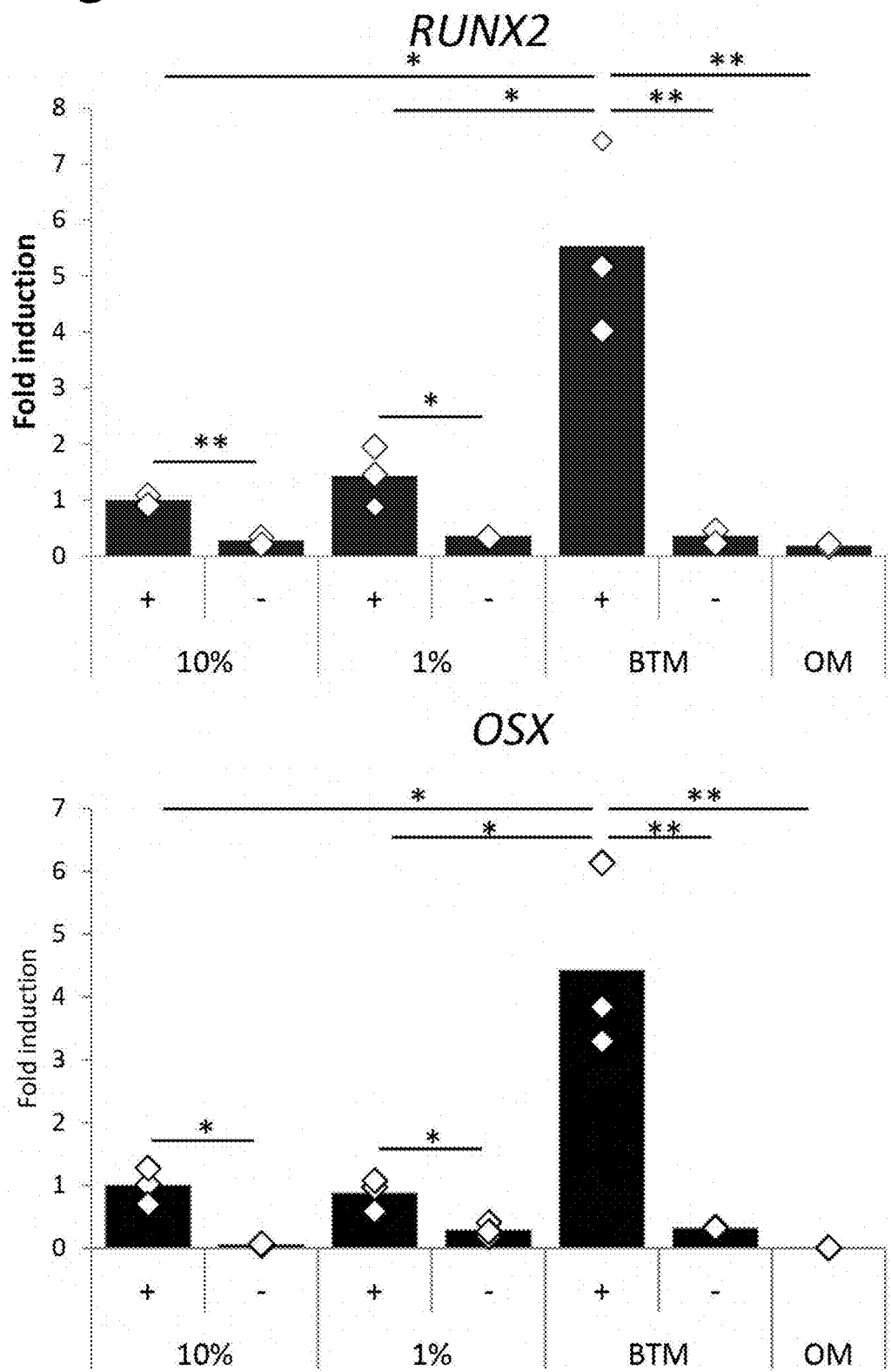

1.1.3 Serum Level Affects BMP-2 Induced Osteochondrogenic Differentiation.

mRNA transcript analysis was used to investigate the effect of serum level on in vitro chondrogenesis, osteogeneis and BMP signalling after BMP-2 stimulation for 6 days, FIGS. 1e-1g. The early chondrogenic marker sex determining region Y-box 9 (Sox9) was upregulated in all conditions stimulated with BMP-2, however, a 2.5-fold elevation was seen in cells stimulated with BMP-2 supplemented CDM as compared to serum containing conditions, FIG. 1e. Similarly, BMP-2 stimulation in all conditions induced expression of Aggrecan and over a 7-fold elevation was seen in cells stimulated with BMP-2 supplemented CDM, as compared to serum conditions. Runx2 and Osterix are early and mid-stage markers for osteogenic differentiation, respectively. BMP-2 stimulation induced a 5-fold up-regulation of both markers in media containing serum, FIG. 1f. In BMP-2 supplemented CDM, an 11-fold up-regulation was depicted, compared to non-supplemented CDM. Moreover, a 5- and 4.5-fold higher expression of Runx2 and Osterix, respectively, was depicted in BMP-2 supplemented CDM as compared to serum containing conditions. The transcriptional regulator distal-less homeobox 5 (Dlx5) was upregulated upon BMP-2 stimulation in all conditions, a phenomenon that was a 5-fold higher in BMP-2 supplemented CDM, FIG. 1g. This trend was also seen for the downstream BMP-target gene ID1, FIG. 1g.

1.1.4 BMP-Release by Stimulated Cells.

An important aspect when analysing cell differentiation state is not only to look at gene expression analysis which reflects differentiation state of the cell, but also to investigate protein secretion, since these are factors that will affect the fracture environment upon implantation. Therefore, BMP-secretion in BMP-2 stimulated hPDCs was measured by a Luciferase signal activated upon ID1 expression in an ID1 reporter cell line, FIG. 1h. The signal was a 72-fold higher in conditioned media (CoM) collected from hPDCs stimulated with 10% FBS media supplemented with BMP-2 compared to non-supplemented media. There was no difference in BMP-activity in conditioned media or freshly made stimulation media (FrM). CoM media collected from hPDCs stimulated in 1% FBS media displayed a 56-fold increased signal as compared to the non-supplemented media. However, this was a 1.2-fold lower as compared to FrM. Analysis of CoM from cells stimulated in CDM displayed a 160-fold elevated signal compared to control cells. Interestingly, this signal was 1.2-fold elevated as compared to FrM.

1.2 Development of a Two-Step Culture Regimen.

Due to the significant effect on chondrogenic and osteogenic differentiation upon BMP-2 supplementation in CDM, we hypothesised that an additional pre-culture prior to BMP-2 stimulation could further improve this effect.

1.2.1 Pre-Culture in CDM Affects Cellular Phenotype.

To investigate the effect of serum free pre-culture in CDM for 6 days, fluorescence activated cell sorting (FACS) analysis was performed. A less decrease in cell size (FSC-A) could be seen in cells cultured in CDM pre-cultured cells following synchronisation as compared to cells cultured in 10% FBS. In addition, a higher and more narrow peak in cellular granularity (SSC-A) could be seen in CDM pre-cultured cells. Cells pre-cultured in media containing 10% FBS remained 98.9% positive for MSC markers CD73, CD90 and CD105 and 93% were negative for hematopoietic markers CD14, CD20, CD34 and CD45. On the other hand, cells pre-cultured in CDM for 6 days displayed a reduced level of positivity for the MSC markers, 81.4% and only 22.3% of these were negative for the hematopoietic markers. To gain further knowledge on which of the hematopoietic markers the CDM pre-cultured cells were positive for, single cell staining for the four markers were performed which displayed that 70% of the cells were positive for CD34. This phenomenon was not seen in cells cultured in 10% FBS or human bone marrow stromal cells pre-cultured in CDM.

1.2.2 Pre-Culture in CDM Affects hPDCs Cell Cycle.

Figure 2A:
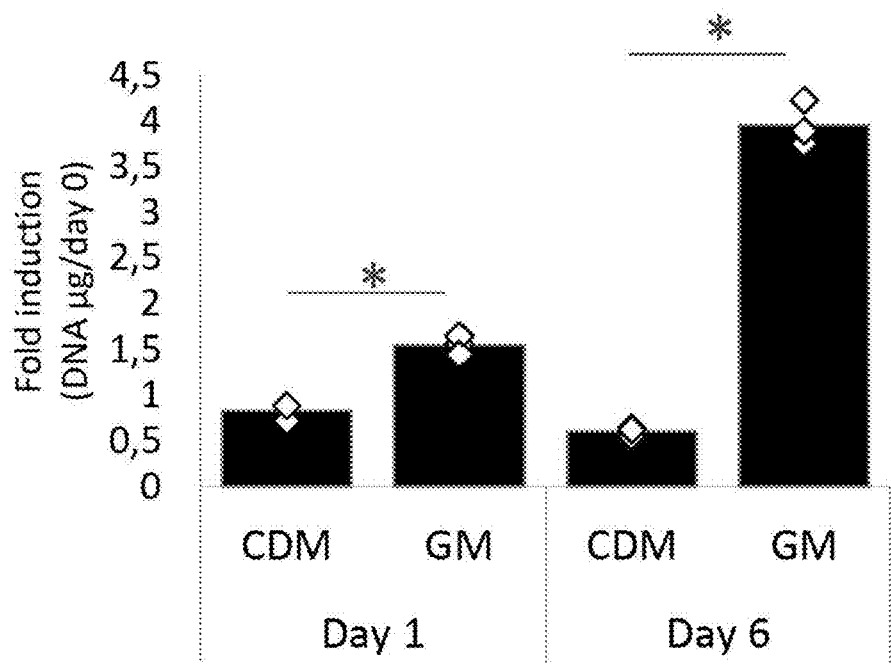
FIGS. 2a-2g. Serum free pre-conditioning for 6 days affected cellular identity.
Figure 2B:
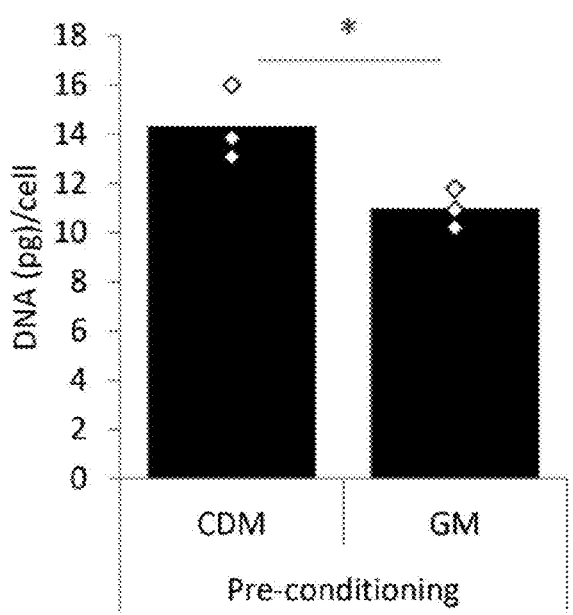

Upon cell-cycle analysis, CDM pre-culture induced a decrease of cells in G0-G1 phase (90.2 vs 95.2), an increase in S-phase (6.0 vs 1.64) and G2-M phase (3.11 vs 2.77) as compared to cells cultured in 10% FBS. Upon cell count and DNA measurements, the ratio of DNA:Cell is less than 0.5 in CDM pre-cultured cells, FIGS. 2a and 2b.

1.2.3 Serum-Free Pre-Culture Changes Cellular Phenotype.

Figure 2E:
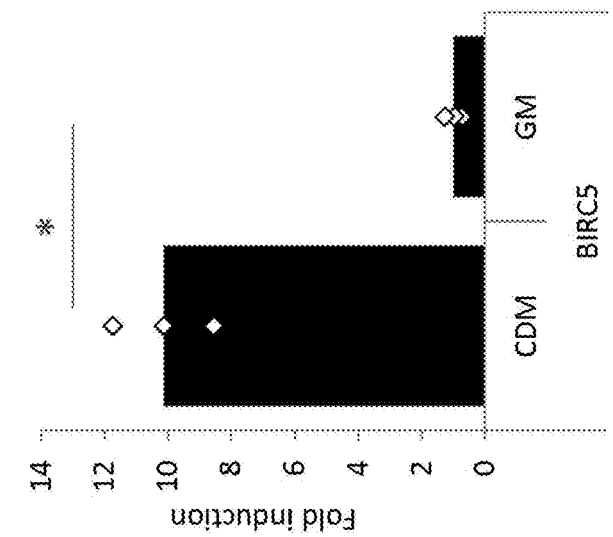
Figure 2D:
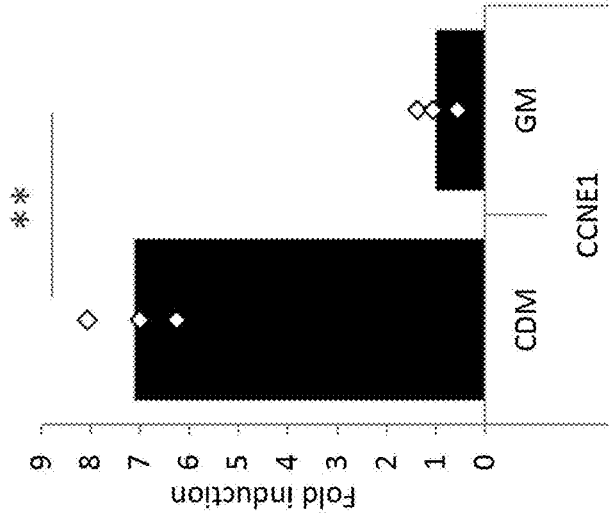
Figure 2C:
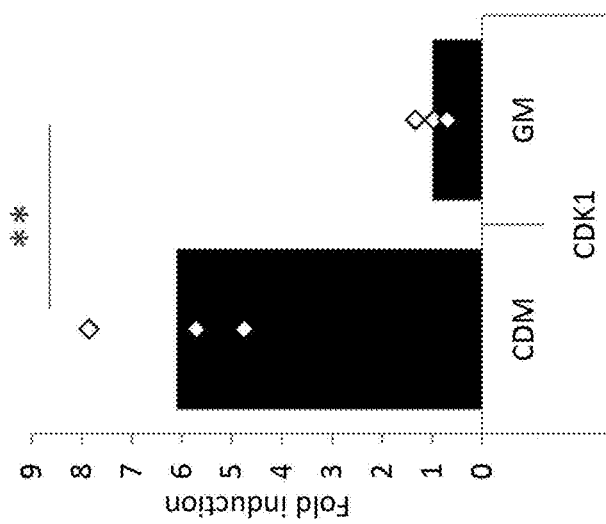
Figure 2F:
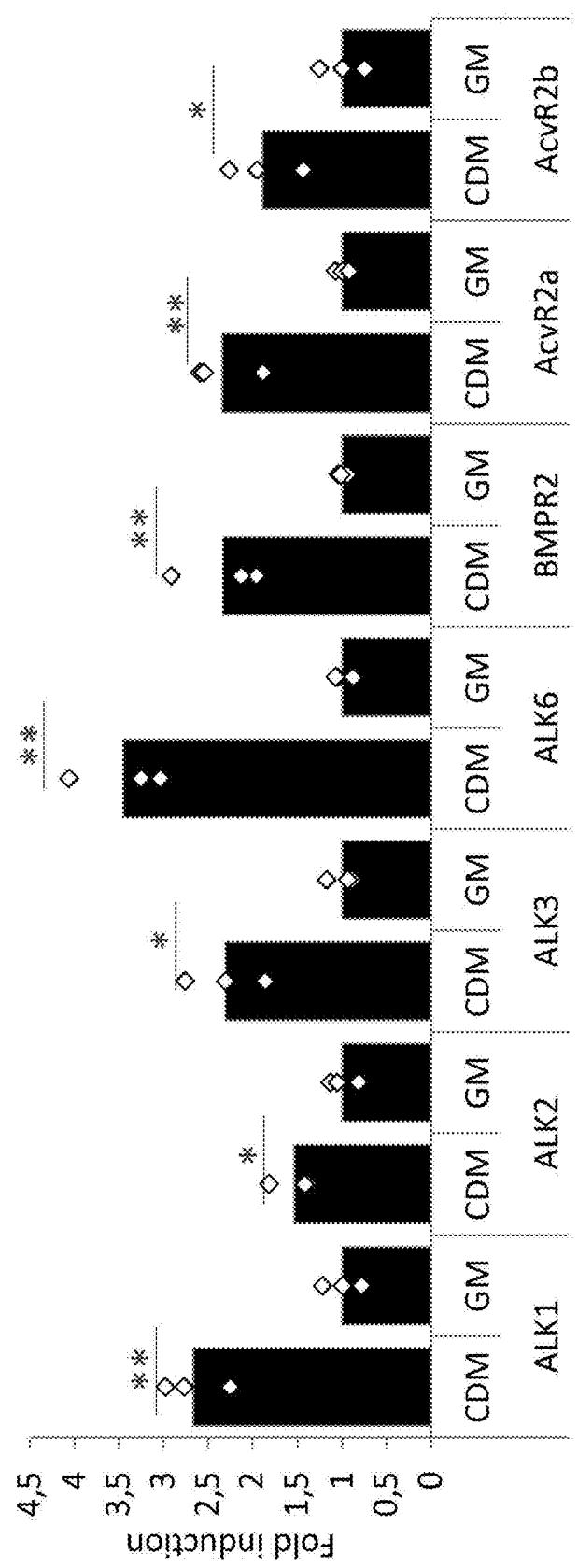
Figure 2G:
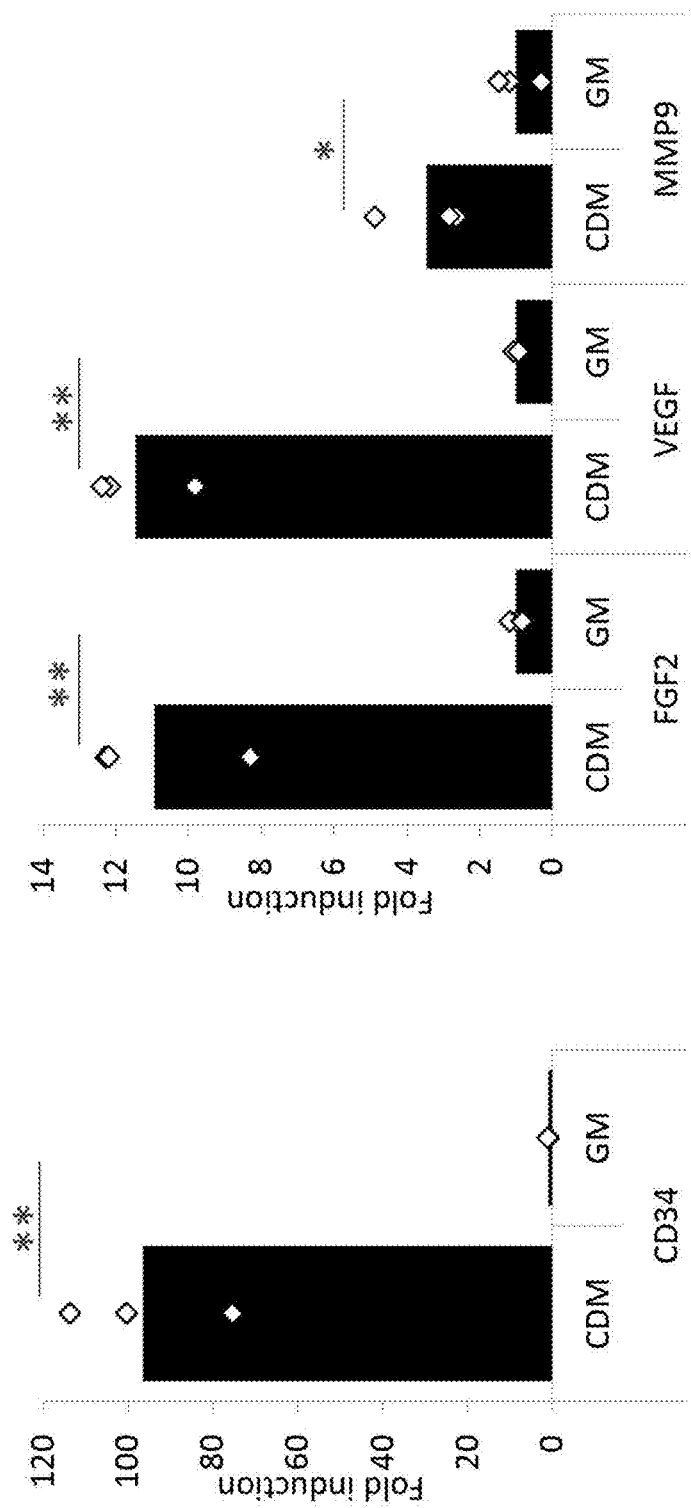

In addition to FACS analysis, mRNA transcript analysis was performed on the pre-cultured cells to investigate the effect on marker genes. To investigate whether adaptations in the cell cycle were caused by the pre-conditioning, expression levels of cell cycle markers Cyclin-dependent kinase 1 (CDK1), Cyclin E1 (CCNE1), and baculoviral inhibitor of apoptosis repeat-containing 5 (BIRC5) were determined. Expression of CDK1, essential for cell cycle progression during S and G2 phases, displayed a 6-fold upregulation in CDM pre-conditioned cells (FIG. 2c). Similarly, we found a 7-fold increased transcript level of CCNE1, required for G1/S transition (FIG. 2d). Interestingly, 10-fold increased level of BIRC5, a negative regulator of apoptosis during the G2/M-phase was seen in CDM pre-conditioned cells (FIG. 2e). CDM pre-cultured cells displayed an increased expression of both BMP-type 1 (Alk1, Alk2, Alk3 and Alk6) and type 2 (BMP-R2, AcvR2a and AcvR2b) receptors, in comparison to the cells pre-cultured in media containing 10% FBS, FIG. 2f. In addition, the FACS data was confirmed at the mRNA level since over a 100-fold increased expression of CD34 was displayed in CDM pre-cultured cells, FIG. 2g. Moreover, these cells also demonstrated a 10-, 12- and 4.6-fold increased FGF2, VEGF and MMP9 expression, respectively, FIG. 2g.

1.2.4 Serum Free Pre-Culture Affects BMP-2 Induced Differentiation.

The effect of the CDM pre-culture upon 24 h, 3 or 6 days of BMP-2 stimulation in CDM was next investigated. Bright field images displayed morphological differences upon BMP-2 stimulation between the two pre-culture conditions. BMP-2 stimulated cells pre-cultured in media containing 10% FBS displayed a heterogeneous cell population with a fraction of elongated cells resembling proliferating cells (resembling non-stimulated cells), and the other fraction possessing a more polygonal cell shape resembling a differentiating cell. Interestingly, cells pre-cultured under serum free conditions in CDM followed by BMP-2 stimulation displayed a more homogenous cell population with the majority of the cells exhibiting a differentiated, polygonal shape. ALP-activity, a marker of mineralisation displayed a 3-fold increase in cells pre-cultured in CDM upon 3 days of BMP-2 stimulation, this was further elevated to a 13-fold after 6 days which was 1.5-fold higher as compared to cells pre-cultured in 10% FBS, FIG. 3a. To investigate temporal chondrogenic and osteogenic differentiation, mRNA transcripts were analysed, FIGS. 3b-3d. After 24 h of BMP-2 stimulation, up-regulation of Sox9 was seen in BMP-2 stimulated samples, this effect was maintained in day 3 and 6 samples. After 3 days of stimulation, cells pre-cultured in CDM displayed a 1.6-fold increased expression compared to cells pre-cultured in 10% FBS, this elevation was increased to 2-fold at day 6. Similarly, the osteogenic marker Osterix displayed a similar up-regulation by CDM pre-cultured cells with a 1.6- and a 1.9-fold increase after 3 and 6 days respectively, as compared to cells pre-cultured in 10% FBS. Additional data supporting these differentiation profiles by expression of Collagen type 2 (Coll2A1), Collagen type 10 (Coll10A1), Runx2, Collagen type 1 (Coll1A1) is presented in FIGS. 4a(1)-4a(4), respectively. Activated BMP-signalling was confirmed by ID1 expression, a 2.5- and 2-fold higher expression was seen in CDM pre-cultured cells after 3 and 6 days respectively, as compared to cells pre-cultured in serum containing conditions. This correlated to a similar expression profile of the transcriptional regulator Dlx5 (FIG. 4a(5)).

1.2.5 Pre-Cultured Cells Undergo Dual Differentiation.

Since the investigated mRNA transcripts suggested a more robust chondrogenic as well as osteogenic differentiation in cells pre-cultured in CDM, we further investigated whether there was a fraction of the cells that differentiated towards a specific lineage. A combined IHC for Sox9 and Osterix in combination with DAPI as a nuclear stain displayed cells positive for Sox9 in both pre-culture conditions but a larger fraction of Osterix-positive cells in CDM pre-cultured cells. Upon quantification of merged z-stack images for the three channels, cells pre-cultured in CDM followed by BMP-2 stimulation displayed elevated positivity for both Sox9 and Osterix, mainly in combination, FIG. 3e.

1.2.6 Elevated Effect of CDM Pre-Culture Upon Stimulation with Several BMPs.

Intriguingly, the phenomenon of elevated effect upon BMP-2 stimulation after the CDM pre-culture was not only specific for BMP-2. In fact, this was consistent with a range of BMPs including BMP-4, BMP-6, BMP-7, BMP9 and GDF5. Upon analysis of Sox9 and Osterix expression, over a 2-fold increased expression was seen for all BMPs in cells pre-cultured in CDM as compared to 10% FBS, FIGS. 5a and 5b. A similar phenomenon was seen upon analysis of the BMP-target gene ID1, FIG. 5c. The elevated osteochondrogenic differentiation was further supported by analysis of Aggrecan, Osteocalcin, Dlx5, BMP-2 and VEGF, FIG. 5d.

1.2.7 Modification of CDM Composition Further Improves the Differentiation Profiles.

Specific components in CDM, which potentially could inhibit the BMP-induced osteochondrogenic differentiation, were hypothesized to be hydrocortisol/hydrocortisone, parathyroid hormone and/or triiodothyronine. Therefore, these were removed, one by one, resulting in a modified CDM-media. The effect was investigated by mRNA transcript analysis on 2D stimulated cells. An elevated effect was seen on differentiation profiles of cells stimulated with media where hydrocotisol or parathyroid hormone was depleted, FIGS. 6a-6j.

1.2.8 The $CD34^+$ Cell Population Displayed a More Potent Osteochondrogenic Potential.

Figure 7A:
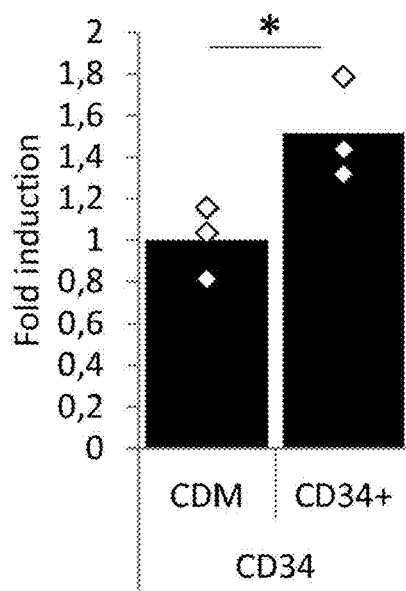
Figure 7B:
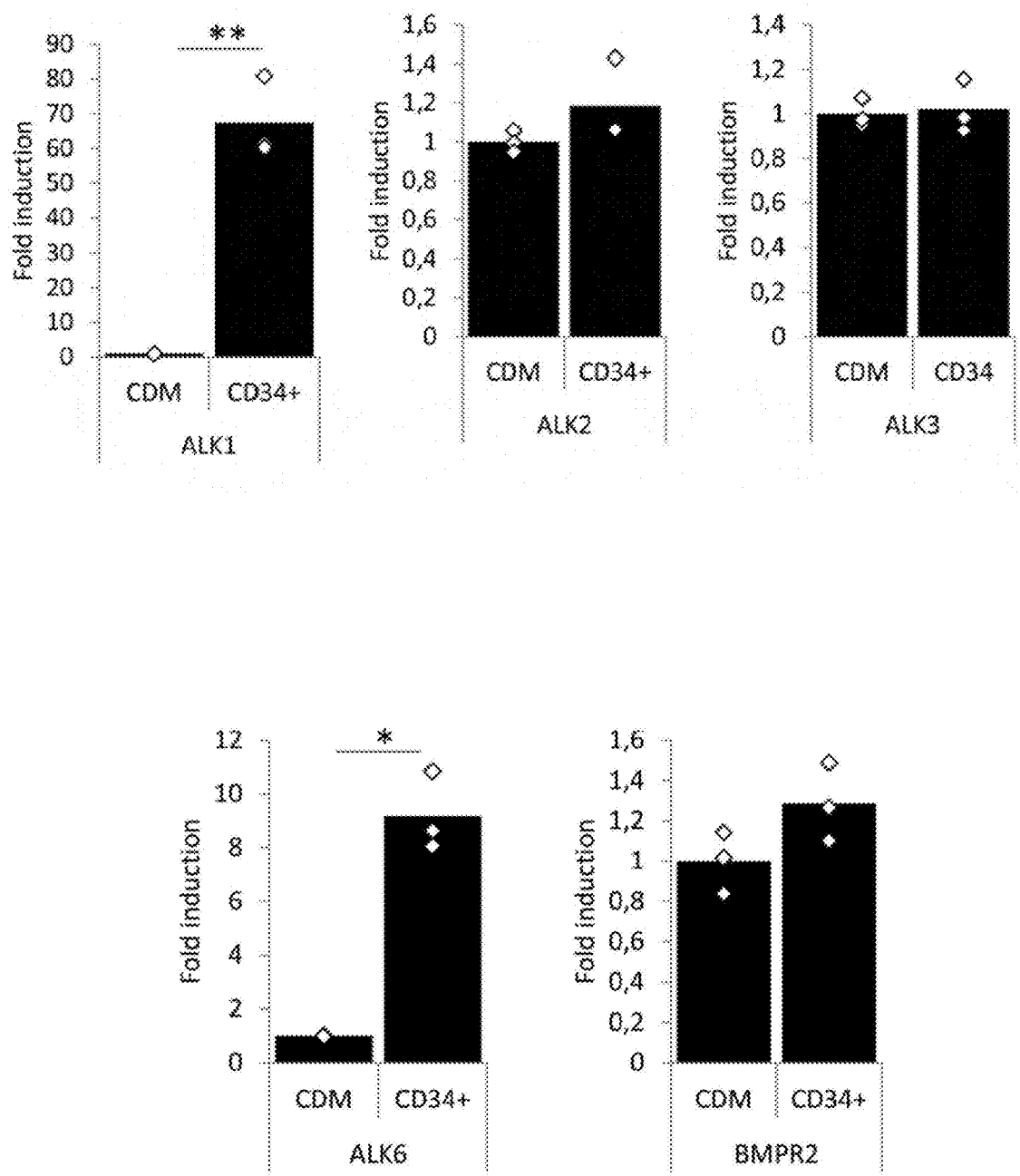
Figure 7C:
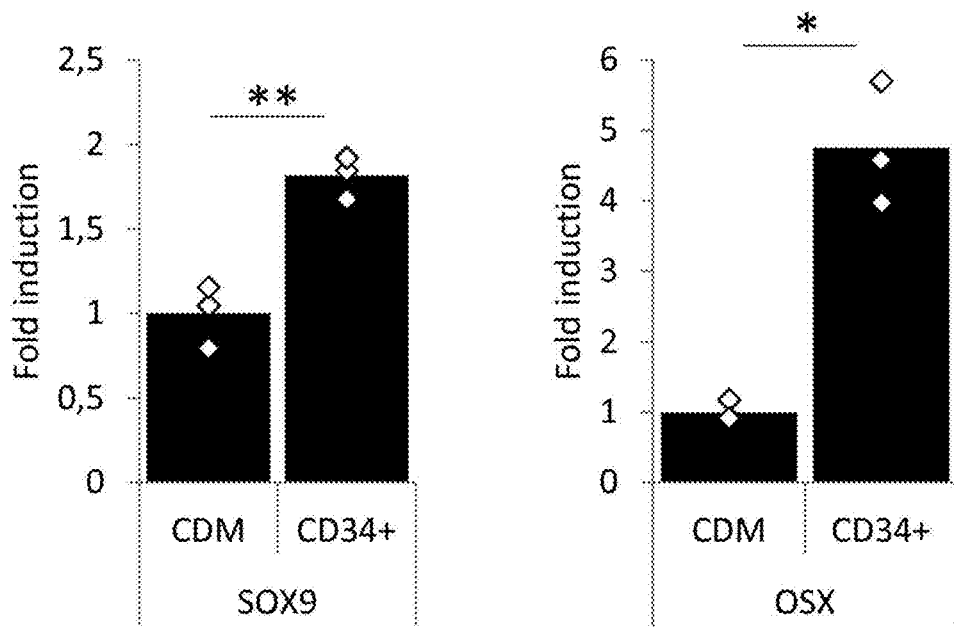
Figure 7D:
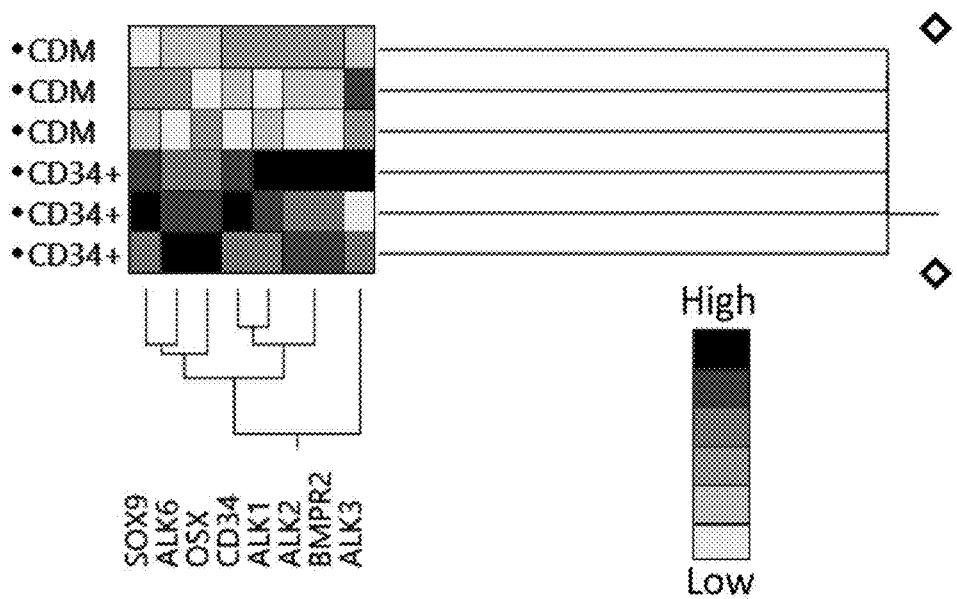
Figure 7E:
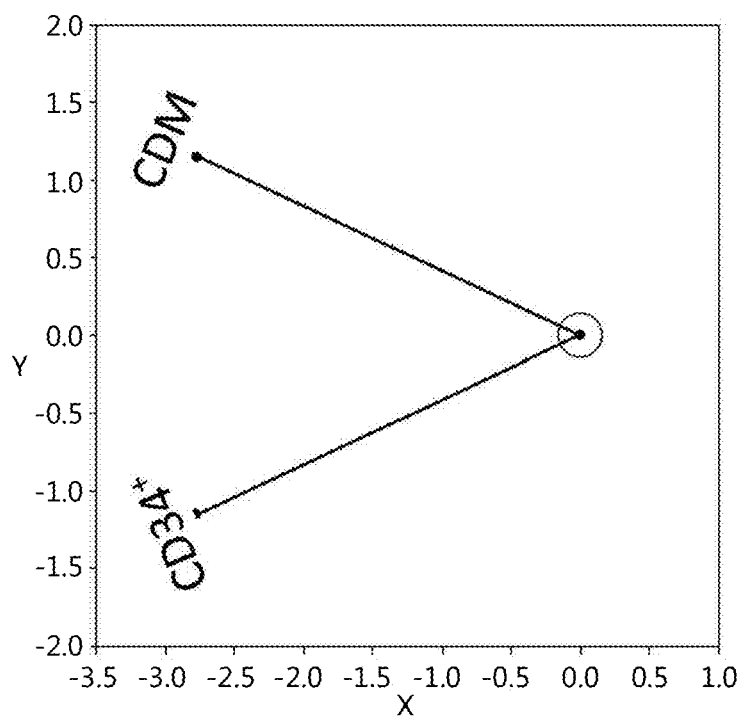

In order to investigate whether it was the $CD34^+$-cell population that were more BMP responsive, $CD34^+$ cells were sorted and compared to the total CDM population. On mRNA transcript level, elevated CD34 expression was confirmed (FIG. 7a). Interestingly, an upregulated expression of BMP-receptors ALK1 and ALK6 was also seen, whereas an upregulated trend was detected for ALK2 and BMPR2 and no difference for ALK3 (FIG. 7b). Upon BMP-2 stimulation, it was shown tha tthe $CD34^+$ population displayed a 2- and 5-fold elevated expression of SOX9 and OSX respectively (FIG. 7c). Cluster analysis displayed correlation between elevated CD34, ALK1, ALK2 ALK6, BMRP2, SOX9 and OSX expression (FIG. 7d) and specific grouping of the $CD34^+$ population was depicted in a constellation plot (FIG. 7e). Combined, these data indicate that the increased osteochondrogenic response is related to the $CD34^+$ cell population.

The improved effect of serum free pre-conditioning was not age or gender dependent.

Figure 8A:
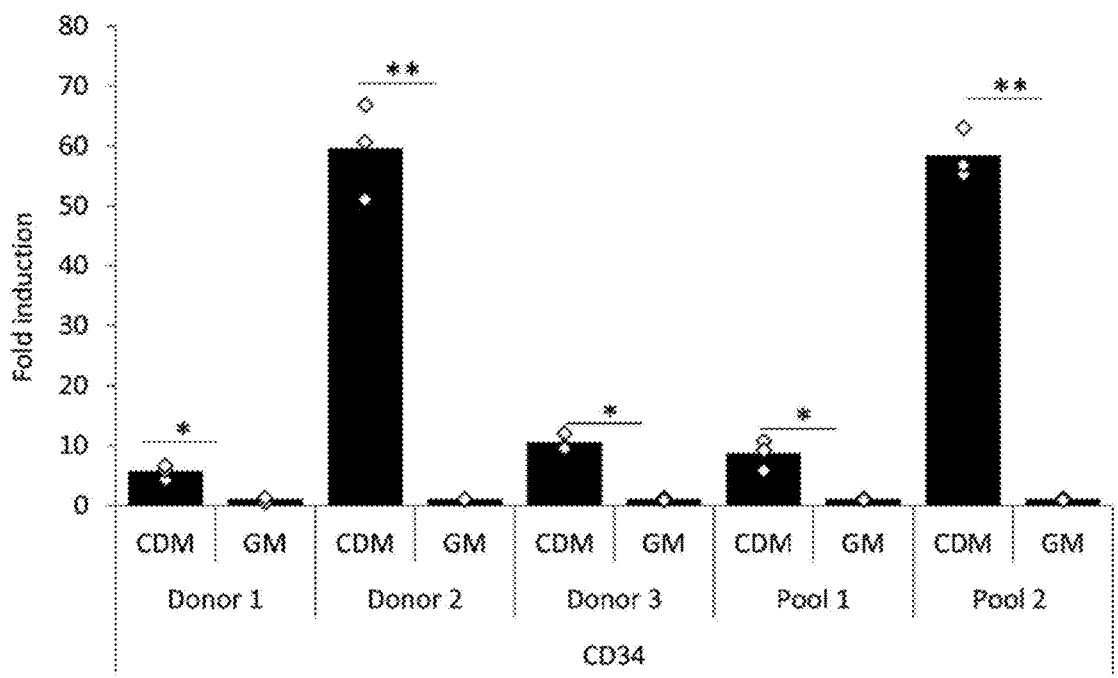
Figure 8C:
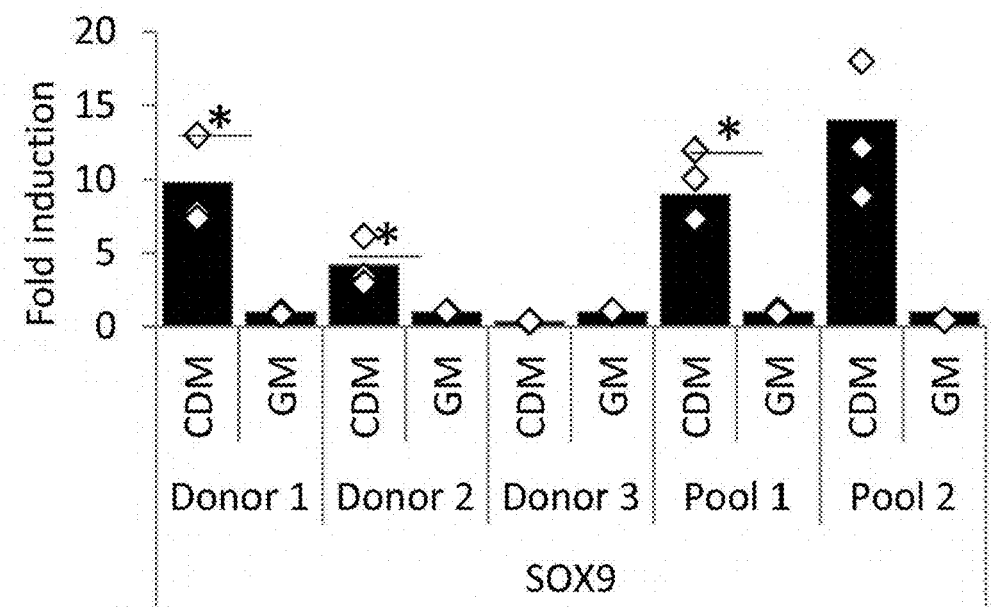
Figure 8D:
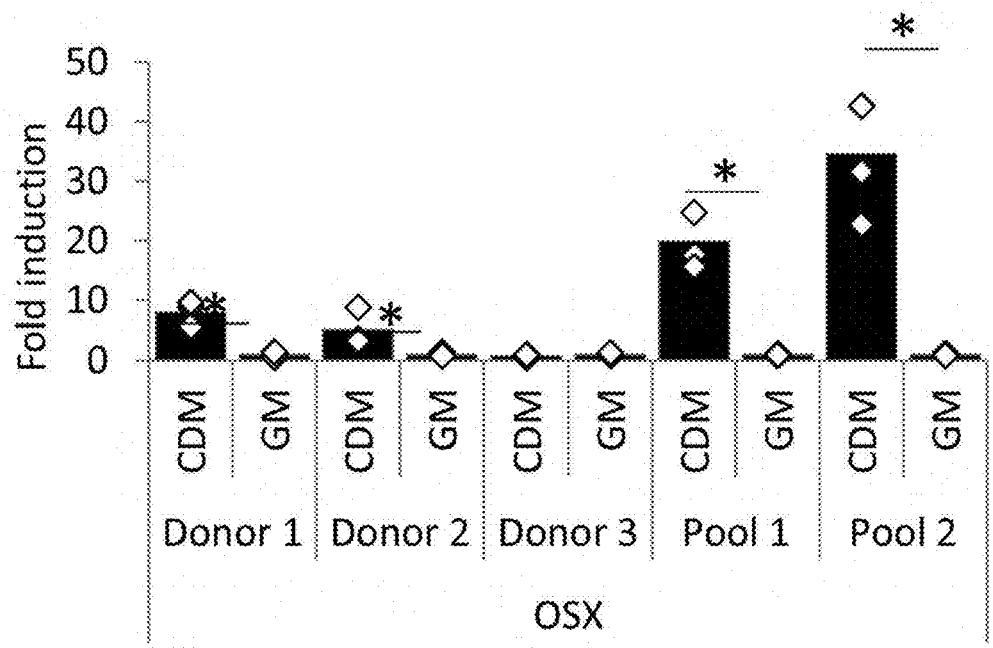
Figure 8E:
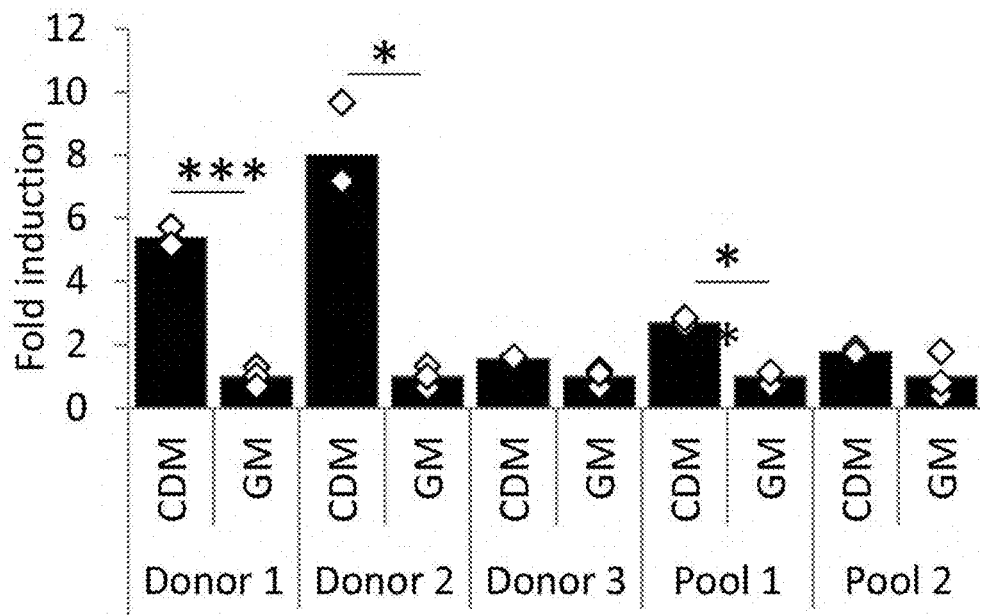
Figure 8F:
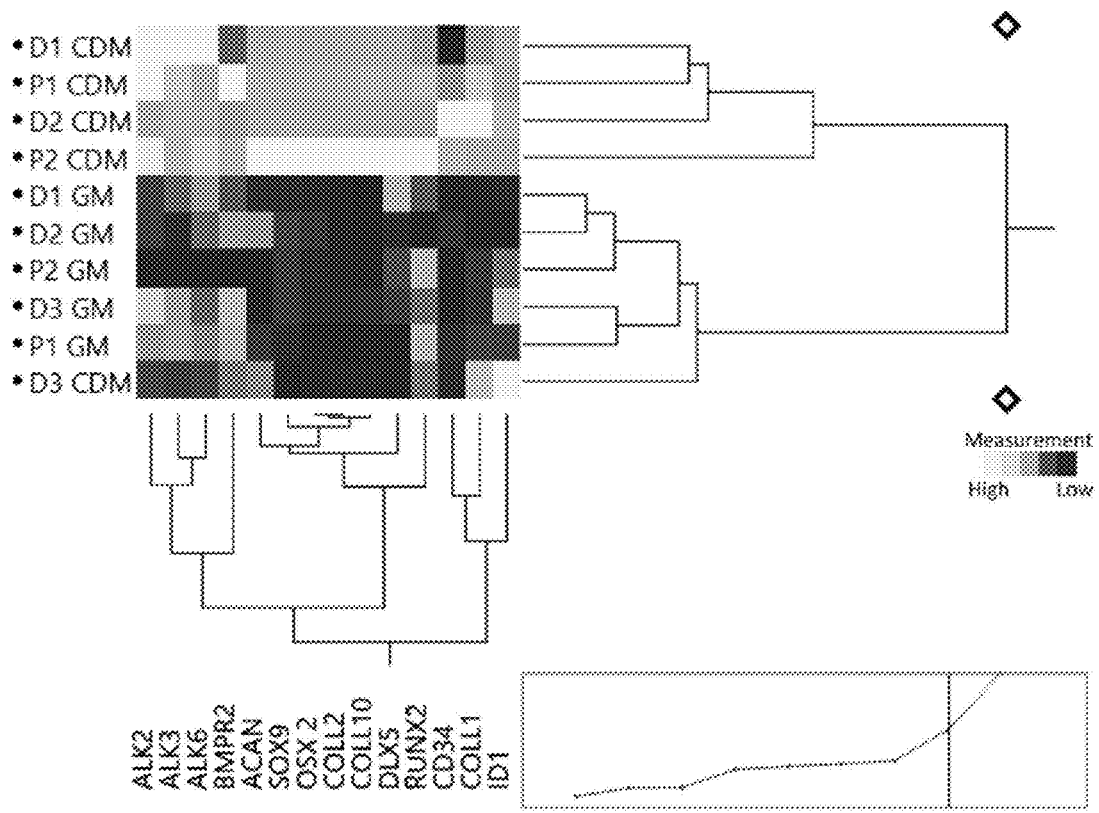
Figure 8G:
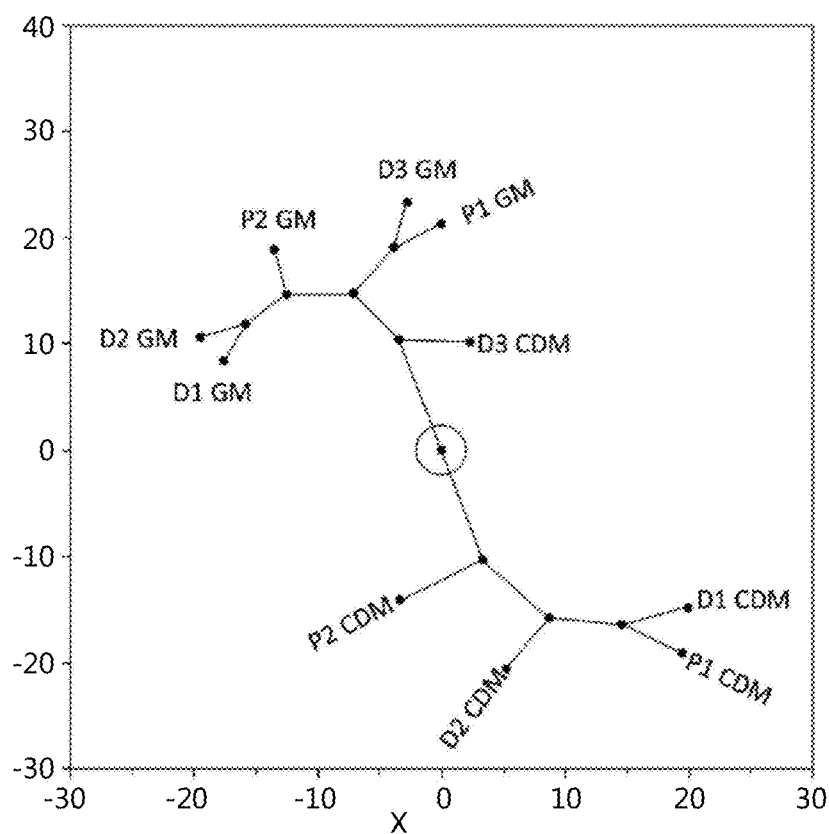

Moreover, the effect of the serum free pre-conditioning was confirmed in young and adult donors (D1-3) as well as in two cell pools with a different age average (P1-2) in which an elevated CD34 expression was correlated to enhanced expression of BMP-receptors (FIGS. 8a and 8b). In addition, elevated osteochondrogenic differentiation upon BMP-2 stimulation was confirmed by elevated SOX9 (FIG. 8c), OSX (FIG. 8d) and ID1 (FIG. 8e) expression. Importantly, with ID1 expression as an example, the coefficient of variance was a 5-, 2-, 8-, 6- and 14-fold higher in serum conditions for the D1, D2, D3, P1 and P2 populations, respectively, as compared to the serum free CDM conditions. Interestingly, the effect of the pre-conditioning led to a specific cluster correlation depending on the pre-conditioning (FIG. 8f). A constellation plot displayed that the improved potential is independent of young or adult donors and gender, but potentially affected by combined donor characteristics such as age and gender (FIG. 8g).

1.3 In Vivo Evaluation of Serum Free Pre-Culture on BMP-2 Induced Cartilage Matrix Production by hPDC.

To investigate the effect of the pre-culture regimen, BMP-2 stimulated cells were encapsulated in a collagen type 1 gel and implanted ectopically in vivo for 3 weeks to evaluate the pre-culture regimen for its suitability as a cartilage intermediate. H&E staining displayed denser staining in BMP-2 stimulated explants, which was further elevated in CDM pre-cultured cells. Fibrous tissue was mainly depicted in non-stimulated cells. Glycosaminoglycan (GAG)-rich matrix was investigated by Alcian blue (AB) staining, which confirmed presence of GAGs in BMP-2 stimulated explants. Upon quantification of the intensity of the staining, a more mature matrix, reflected by higher intensity of the stain, was displayed in CDM pre-cultured cells followed by BMP-2 stimulation, FIG. 9. In addition, cellular condensations could be found between GAG-rich areas. Staining for Masson's Trichrome, in which intensity increases with collagens density, confirmed the findings from AB.

1.4 Bioinspired Formation of 3D Microtissues Combined with BMP-Technology.

In regenerative medicine, a pure cell-based product is suitable for translational applications since growth factor delivery and/or allogeneic materials are excluded and tissue-development is purely driven by implanted cells. Therefore, we further developed the culture regimen to a 3D bio-mimicking system, cell aggregates. The size of the aggregate affects mechanical stimulation on the cells, nutrient flux and cell-cell interaction forces. Therefore we initially determined an optimal aggregate size through an in vitro screening between 50, 100 and 250 cells/aggregate. Pre-cultured cells were aggregated with or without BMP-2 stimulation for 6 days and investigated by microscopy, mRNA transcript analysis, histology and IHC. As control to the aggregates, 2D BMP-2 stimulated cells and non-stimulated cells were included in the study. Bright field images displayed most robustly formed aggregates in the 250 cells/aggregate size, FIG. 10a. In conditions of 50 and 100 cells/aggregate higher size variability was seen as well as debris formation. Interestingly, aggregation in combination with or without BMP-2 stimulation reduced expression of MSC markers and reduced cell size, FIG. 10b and FIG. 11. Upon gene expression analysis, the combined effect of BMP-2 stimulation and aggregation displayed an up-regulated expression of chondrogenic markers Sox9, Coll2a and Aggrecan, FIG. 12a, as compared to non-stimulated cells. The most elevated expression was found in 2D stimulated cells. Between the BMP-2 stimulated aggregates, Sox9 expression did not display differences in expression levels between the different sizes. Coll2 expression decreased with increased aggregate size, whereas increased expression level with increasing aggregate size was seen for Aggrecan. For osteogenic markers Runx2, Alkaline Phosphatase (ALP) and Osterix aggregation in combination with BMP-2 stimulation had an elevated effect, which was further increased with aggregate size, FIG. 12b. Enhanced expression in 250 cells/aggregate was a 2-fold and 5-fold in ALP and Osterix, respectively, as compared to 2D stimulated cells. The up-regulated differentiation profile could be correlated to expression of the transcriptional regulator Dlx5 and BMP marker gene ID1, FIG. 12c. In addition, we investigated VEGF expression which was upregulated upon BMP-2 stimulation, further enhanced with increasing aggregate size. Next, we confirmed gene expression data by IHC for Sox9 (red) and Osterix (green) with DAPi (blue) as a nuclear marker. Merged Z-stack images confirmed elevated Sox9 stain upon BMP-2 stimulation and increased positive stain for Osterix with increasing aggregate size.

1.5 In Vivo Evaluation of 3D Constructs Based on Cellular Aggregation.

Based on the in vitro analysis, 250 cells/aggregate were selected for in vivo evaluation. In total, five conditions were included for implantation: aggregates with and without BMP-2 stimulation for 6 days, 2D stimulated or non-stimulated cell and a final condition where cells had been stimulated in 2D cultures with BMP-2 for 6 days followed by aggregation without BMP-2 stimulation for 24 h. All conditions were encapsulated in a collagen type 1 gel and subcutaneously implanted in NMRI$^{mu/mu}$ mice for 1 and 3 weeks, subsequently explanted and investigated by histology and IHC.

1.5.1 In Vivo Tissue Formation 1 Week Post Implantation.

Upon analysis of week 1 explants, H&E staining displayed micro vessel formation which upon quantification was shown to be enhanced in samples including BMP-2 stimulation, indicating a synergistic effect when combined, FIG. 13a. No bone spicules could be found in any of the conditions. AB staining revealed a cartilaginous matrix, rich in GAG content in BMP-2 stimulated cells, aggregates and again, elevated intensity of the stain was seen by the synergistic effect of the two factors when combined. This data was confirmed by Masson's Trichrome (MT) stain which displayed a more mature matrix tissue with denser collagen content in conditions combining BMP-2 stimulation and aggregation.

1.5.2 Endogenous BMP-2 Production BMP-2 Stimulation and Aggregation.

Interestingly, IHC for pSmad1/5/8 displayed active BMP-signalling in explants which had been stimulated with BMP-2 or aggregated, depicted by brown nuclei. In addition, a synergistic effect of both factors combined was seen in form of increased number of positive nuclei. This data was confirmed by quantification of positive nuclei normalized to total number of nuclei, FIG. 13b. Due to the active BMP-signalling, we hypothesized that the combined stimulation of BMP-2 and aggregation stimulated endogenous production of BMP-2. Therefore, we investigated the presence of BMP-2 in conditioned media (FIG. 13c) by enzyme-linked immunosorbent assay (ELISA). With fresh stimulation media as control, the combined effect of BMP-2 stimulation and aggregation displayed 1.5-fold higher BMP-2 level in conditioned media. In addition, aggregation itself induced BMP-2 production (FIG. 13c), confirmed by gene expression data (FIG. 13d).

1.6 In Vivo Tissue Formation 3 Weeks Post Implantation.

Figure 13E:
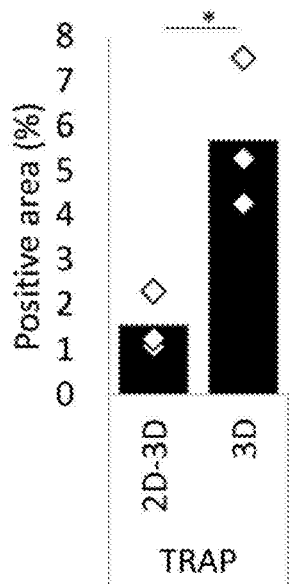
Figure 13F:
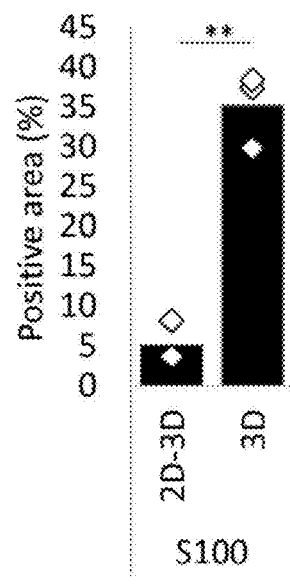
Figure 13G:
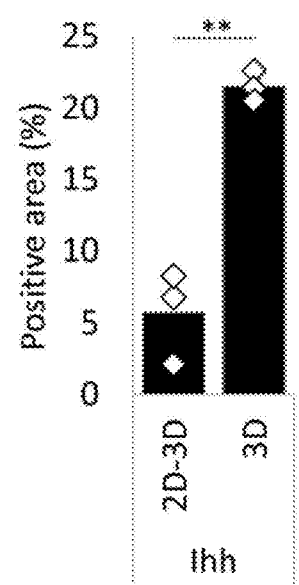

After three weeks post implantation in vivo, H&E staining displayed presence of condensations of hypertrophic chondrocytes in BMP-2 stimulated aggregates, a phenomenon that was not seen in 2D stimulated cells followed by aggregation. An AB stain confirmed the formation of a dense matrix rich in GAGs, and the presence of hypertrophic chondrocytes were confirmed in BMP-2 stimulated aggregates. These findings were further supported by a MT staining. To analyse remodelling of the cartilaginous matrix, Tartrate-resistant acid phosphatase (TRAP) staining was performed which displayed positive areas in close vicinity to GAG-rich areas and hypertrophic chondrocytes. Upon quantification, the BMP-2 stimulated aggregates displayed a 2-fold higher percentage of TRAP$^+$ area (FIG. 13e). Remodelling of the cartilage intermediate was further confirmed by IHC for DIPEN, the cryptic epitope of ACAN, typically exposed upon its degradation. To further characterize the cartilaginous tissue, quantification of positive stained IHC for S100 confirmed a 6-fold higher positive area in BMP-2 stimulated aggregates (FIG. 13f). Furthermore, a mature cartilaginous tissue was confirmed by quantification of IHC for Indian hedgehog (Ihh), expressed by (pre)hypertrophic chondrocytes (FIG. 13g). These data confirm the in vivo maturation and reveal that the combined approach of cell aggregation and exposure to BMP-2 induced in vivo tissue development in a process resembling the early stages of endochondral bone formation.

1.7 Healing of a Critical Size Long Bone Defect.

Based on the ectopic endochondral-mimetic development of the in vitro primed microtissues, the orthotopic behaviour was next assessed in a critical size tibia defect. Upon transplantation, the in vitro BMP-2 stimulated aggregates led to bridging within 4 weeks as assessed by X-ray analysis (FIG. 14a). Non-unions were confirmed in 4 out of 5 controls up to 8 weeks post the creation of the defects. Full bridging by a mineralized matrix at 4 and 8 weeks was confirmed by nano-CT scanned explants (FIG. 14b). The implants were qualitatively analysed using histology and IHC. H&E and SafraninO/Fast green staining revealed cartilage intermediate two weeks post implantation. In the centre of the cartilaginous callus, hypertrophic chondrocytes were present whereas a mineralized tissue had started to form in the periphery, the latter being visualized by MT staining. The early cartilage intermediate displayed positivity for TRAP, suggesting remodelling into bone, a process that was maintained at week 4 and 8. Moreover, the cartilage callus displayed positivity for human Osteocalcin (hOCN), confirming the contribution of donor cells. At 4 weeks, a fully mineralized bridging was observed, even though the MT staining showed also less mature mineralized zones. This mineralized tissue stained positive for hOCN. After 8 weeks, the mineralized matrix displayed less zones of immature bone tissue which was also confirmed to be positive for hOCN. In addition, qualitative analysis confirmed the absence of cartilage or osseous tissue in control non-unions as well as a negative staining for hOCN. These data demonstrated a successful in vivo bridging of the in vitro primed cell-based construct in a critical sized long bone defect.

Discussion

The development of well characterized cell based advanced therapeutic medicinal products (ATMPs) plays a crucial role in the translation of biologically functional bone grafts. Nowadays, ATMPs are expected to repair, replace and/or regenerate damaged or missing tissue in a cost-efficient manner. In particular for bone regenerative strategies, ATMPs are expected to heal existing or predicted non-unions, thereby reducing the long term suffering and the cost of patient care. Cell based ATMPs are typically based on three basic elements: osteogenic cells, osteoinductive growth factors and osteoconductive biomaterials. Ideally, the chosen combination forms a biomimetic environment that drives the cells into formation of a new functional tissue. The development of ATMPs requires expertise from several disciplines including biology and engineering and is therefore a multidisciplinary process. Biology provides crucial information on the underlying molecular signalling mechanisms and understanding of cellular behaviour while engineering is employed to mimic these processes. Optimally, this can be achieved by creating a stimulating microenvironment which upon activation leads to a self-sustained tissue with the spatiotemporal release of crucial molecules and facilitates integration within the host. For bone tissue engineering strategies, BMP-technology is a well explored field due to the growth factors' potent bone forming capacity. This has led to extensive research and subsequent development of products involving members of the BMP-family. Some of them have been approved by the FDA and have been used in the clinical setting. In these products BMPs are combined with a collagen sponge leading to a burst release of the BMP and hence requires supra-physiological levels of the growth factor to reach sufficient healing. Unfortunately, this has been reported to lead to uncontrolled bone formation/resorbtion and negative side effects such as cancer and male sterility. For critical fractures, the healing through a cartilage intermediate, induced by BMPs, is attractive, since this may allow earlier stabilization of the fracture. We have developed a cell-based strategy where BMPs are coated within physiological levels onto partly osteoinductive CaP scaffolds, followed by seeding of hPDCs. Upon in vivo implantation, these constructs induced in vivo bone and bone marrow formation, through a cartilage intermediate (unpublished results of the inventors). Hierarchical clustering displayed that CaP-scaffold characteristics affected BMP-induced differentiation. This was reflected by variations between the different BMPs' potency on 2D stimulated cells and the influence by the CaP-environment on activated signalling pathways in 3D, subsequently affecting in vivo tissue formation. Therefore a more pure cell-based strategy is more suitable in the development of translational ATMPs. Initially for this approach, the use of a relevant cell culture media is essential as it needs to maintain cell survival, be optimal for BMP-technology and meet the need for clinical translation. Therefore, as a first step, we identified that the serum free CDM and the standard culture media containing 1% FBS maintain cell survival rather than induce cell proliferation. Subsequently, these were selected to further investigate the effect on osteo/chondrogenic differentiation by BMP-2 supplementation. We saw a powerful, enhanced effect on both osteogenic and chondrogenic differentiation after 6 days of BMP-2 stimulation in the serum free condition, which also could be correlated to enhanced BMP-signalling. In addition, the removal of serum did not only elevate the potency on differentiation, analysis of conditioned media from the stimulated cells on an ID1-reporter cell line confirmed secretion of BMPs by the stimulated cells. This phenomenon is an important feature for the in vivo setting, since BMP-secretion by the cells upon in vivo implantation will stimulate host cells in the fracture environment to contribute to the fracture healing. After implantation, it has previously been reported that in vitro expanded cells often undergo apoptosis, suggested to be due to the radical switch in environment. In vitro, cells face culture conditions rich in nutrients and high in $O_2$, and need to instantly adapt to a compromised in vivo setting with no or low level of blood vessels leading to absence of both $O_2$ and nutrients. Our method however, by the introduction of an additional pre-culture step in the serum-free CDM leads to an adaptation and/or selection of more robust progenitor cells. This leads to a further enhanced differentiation upon BMP-stimulation. Hence, cells were first cultured in the serum-free CDM or in standard culture media containing 10% FBS for 6 days followed by BMP-2 stimulation in CDM for another 6 days. After the 6 days of CDM pre-culture, a dramatic shift in MSC marker expression was seen. Cells became negative for MSC markers CD73, CD90 and CD105 but positive for the hemangiopoietic marker CD34. In regards to skeletal tissue engineering, this is interesting since previous studies have revealed higher vascular gene expression and elevated angiogenic response in $CD34^+$ than in $CD34^-$ cells, concluding that CD34 expression correlates with enhanced vasculogenic and angiogenic potential. The CDM pre-cultured cells that became $CD34^+$ also witnessed an enhanced expression of angiogenic markers such as FGF2, VEGF and MMP-9. Interestingly, an elevated expression of BMP type 1 and 2 receptors was also seen, as this might lead to cells being more responsive to BMP-stimulation. However, this is contradictory to previous reports on adipocyte derived stem cells where $CD34^-$ cells displayed elevated expression of BMP-receptors together with an elevated response to BMP-stimulation in vitro. Encouragingly, the serum free pre-culture of hPDCs displayed an earlier initiation of, as well as an elevated osteochondrogenic response to BMP-2 stimulation as compared to serum containing conditions. In fact, this was not only valid for BMP-2, but also upon stimulation of BMP-4, BMP-6, BMP-7, BMP-9 and GDF5. Since the elevated osteogenic as well as chondrogenic gene expressions were seen simultaneously, IHC for Sox9 and Osterix displayed that it is mainly the same cell that is positive for both markers. Encouragingly, the elevated differentiation capacity seen in vitro could be correlated to an elevated GAG production in vivo, 3 weeks post subcutaneous implantation.

We found that a biomimicking system in form of cell aggregation provides the basis to a system that potently drives the formation of a cartilage intermediate upon implantation. Initially, we investigated the optimal size of the aggregate since this affects nutrient supply, cell-cell interactions and mechanical stimulation in form of forces applied by the aggregated cells. Interestingly, osteogenic differentiation was more affected by the size of the aggregate than chondrogenic differentiation. This could potentially be because of the elevated forces exerted by the increased number of cells more effectively stimulating the osteogenic phenotype. Histology on aggregates stimulated for 6 days in vitro, confirmed that no GAG-rich tissue or mineralization was present at this stage. Strikingly, samples treated with either BMP-2 or aggregated, displayed micro vessel formation, along with the presence of cartilaginous matrix and cells positive for pSmad1/5/8 only 1 week post implantation. Upon quantification, a synergistic effect was seen by the combined BMP-2 stimulation and aggregation. The surprisingly active BMP-signalling indicated endogenous BMP-production by the aggregates. To investigate this, we analysed BMP-2 secretion by the aggregates in conditioned media as well as within cell lysates at the $6^{th}$ day of BMP-2 stimulation, but also in samples collected 24 h after the stimulation was stopped. By using fresh stimulation media as control, we saw that BMP-2 stimulation as well as aggregation induced an endogenous production of BMP-2, since levels in these conditions were elevated as compared to the stimulation media in day 6 samples. Moreover, in day 7 samples, after 24 h of BMP-2 depletion from the media, BMP-2 was still detected in the conditioned media. This explains the active BMP-signalling in in vivo samples, depicted by pSmad1/5/8 IHC. Since BMP-2 stimulation has been stopped, aggregates continue to produce BMP-2 and hence maintain differentiation. This data displays that all in vivo events come from the in vitro stimulation and are purely driven by implanted cells. Together with the week 1 in vivo data, the synergistic effect of BMP-2 stimulation and aggregation leads to enhanced cartilage formation through elevated differentiation driven by endogenously expressed BMPs. Moreover, this finding is of interest for future clinical translation since in this setting, no recombinant growth factors will be implanted in the patient, which comes with the concerns of control and safety of the ATMP. So far the achievements in the (pre)clinical setting revealed that the use of exogenous high amounts of BMPs resulted in toxic side effects. Therefore, it is necessary to keep the concentrations of the BMPs to more physiological relevant concentrations. Thus in our invention, we use a pre-stimulation of the cells with exogenous BMPs, leading to an improved cellular behaviour in the ATMP and keeping the total concentration BMPs (which comprises endogenous BMPs) in the ATMP to more physiological relevant levels. In some embodiments of the present invention, extra exogenous BMPs are coated on the biocompatible carriers in a low concentration, preferably lower than 50 ng BMP/mm$^3$. In comparison to previous reports where BMP-technology is used, the remaining cartilage matrix and lack of de novo bone tissue formation might seem disadvantageous. This is rather due to the implemented system, since no growth factors or osteoinductive material was implanted hence a less potent but more controlled effect is seen.

Moreover, assessment in a critical long bone defect displayed successful bridging four weeks post transplantation. Qualitative analysis at two weeks displayed a process resembling a process of endochondral bone healing. Encouragingly, transplanted cells actively contributed to both the intermediate cartilage tissue as well as the bridging bone, depicted by IHC for hOCN. A reduced hOCN positive staining was seen in the later time points, suggesting that host derived cells are involved in the remodelling of the newly formed bone tissue.

It is a general concern, especially with clinical translation in mind, that phenomena and responses seen in the in vitro situation are hardly reflected in vivo. In this study, the in vitro data is also reflected in the in vivo situation. Subsequently, this work displays the enhanced in vitro and in vivo effects of replacing standard culture media containing bovine serum to a serum free chemically defined media for BMP-technology strategies within the field of bone tissue engineering. Standard in vitro cell culture work today involves the use of xenogenic serum such as FBS due to availability and cost effectiveness in comparison to allogenic serum. In addition to limited clinical translation of work performed under these conditions, the variability of the non-isogenic serum leads to an uncontrolled experimental outcome depending on batch-batch differences. This is due to the unpredictability of protein, cytokine and hormone composition in the serum, which is specific for each individual and allogenic serum is therefore not suitable. The optimal solution may be the use of isogenic serum, but this requires blood collection directly from the patient, not feasible for in vitro research, and may also not be suitable in a traumatic situation. Therefore, the replacement of vital components in the serum with chemically defined factors is a suitable strategy to use as a serum replacement in the development of robust clinically translatable bone forming constructs.

Materials and Methods

Cell Isolation.

Periosteal biopsies (0.5 cm$^2$) were harvested from the medial side of the proximal tibia of male and female adolescent and adult patients during total knee replacement surgery or distraction osteogenesis. The periosteum was stripped from the tibia with a periosteal lifter. Specimens were transported in growth medium (GM) consisting of high-glucose Dulbecco's Modified medium (DMEM, Invitrogen, Merelbeke, Belgium) supplemented with 10% FBS (Gibco, Merelbeke, Belgium) and antibiotic-antimyocotic solution (100 units/ml penicillin, 100 µg/ml streptomycin and 0.25 µg/ml amphotericin B; Invitrogen, Merelbeke, Belgium). The biopsies were digested over night at 37° C. in 0.2% type IV collagenase (Invitrogen, Merelbeke, Belgium) in GM. Subsequently, periosteal cells were collected by centrifugation and seeded in T25 flask in GM. Non-adherent cells were removed after five days by changing the medium, remaining cells were expanded in monolayer in GM. Upon confluence, hPDCs were trypsin released (0.25% trypsin, 1 mM EDTA; Invitrogen, Merelbeke, Belgium) and replated with a seeding density of 5000 cells/cm$^2$. From passage two, hPDCs from six different donors were pooled with 6*10$^6$ cells from each donor. For cryopreservation, hPDCs were suspended in DMEM with 20% FBS and 10% DMSO (Sigma, Bornem, Belgium) and stored in liquid nitrogen. Cells were thawed, cultured upon confluence and further handled for analysis. The ethical committee for Human Medical Research (KU Leuven) approved all procedures, and the patient informed consents were obtained.

Serum Level Affects hPDC Proliferation.

In vitro expanded pooled cells were seeded at a cell seeding density of 5 000 cells/cm$^2$ in 24-well plates and left over night for cell attachment. Thereafter, cells were washed three times in phosphate buffered saline (PBS) (BioWhittaker, Lonza, Verviers, Belgium) followed by 16 h incubation in medium containing 0.1% FBS for cell synchronization. Next, the monolayers were again washed three times with FBS and subsequently growth medium (GM) containing, 10-, 5-, 2-, 1-, 0.5- or 0% FBS was applied to the wells. In addition, two serum free media were included in the study, one commercially available serum free medium (Lonza, Verviers, Belgium) and one in house developed chemically defined medium, previously shown to maintain the chondrogenic phenotype in rabbit articular chondrocytes, patent US20010039050 with the removal of the growth factor cocktail (ie. removal of PDGF, EGF, and bFGF) as well as (3-Glycerophosphate and lineolic acid and was defined as BMP-Technology Medium (CDM). Cells were stimulated with the different media compositions for 21 days and samples for DNA quantification were taken at day: 0, 1, 3, 6, 12 and 21. For sampling, media was removed and the monolayers were washed three times in PBS followed by 5 min incubation in 0.05% TritonX-100. After three cycles of freeze thawing −80° C. to 4° C., samples were sonicated on ice 3×3 seconds followed by centrifugation to remove cell membrane remnants. The supernatants were collected and DNA content was measured using Quant-i™ PicoGreen® dsDNA assay (Invitrogen) (n=3) according to the manufacturer's instructions.

Serum Level Affect BMP-2 Induced Differentiation.

Cells were seeded at a cell seeding density of 10 000 cells/cm$^2$ in 24 well plates and left over night for attachment. Next, the monolayers were washed three times with PBS followed by 16 h incubation in GM containing 0.1% FBS for cell synchronization. Following, cells were again washed three times with PBS to remove serum remnants and replaced by stimulation media which were selected based on the proliferative capacity from the in vitro proliferation study. GM containing 10% and 1% were selected together with the CDM and subsequently supplemented with 100 ng/ml BMP-2 (Medtronics, Minneapolis, Minn., U.S). Media was changed after 24 h, on day 3 and 5 and cells were stimulated for a six day period and samples were collected for DNA, Alkaline phosphatase (ALP)-activity and gene expression analysis. As a negative control, cells were stimulated with the same media but un-supplemented with BMP-2. As a positive control, to ensure hPDCs ability to differentiate towards the osteogenic lineage, standard osteogenic medium (GM with 10% FBS supplemented with 100 nM dexamethasone, 10 mM (3-Glycerophosphate and 50 mM ascorbic acid 2-sulfate (Sigma)) was used.

DNA and ALP-Activity Analysis.

After six days of stimulation in the monolayers, cells were washed three times with PBS followed by 5 min incubation in 0.05% TritonX-100. Lysed cells were collected and sonicated on ice bath 3*3 see, followed by centrifugation to remove cell membrane remnants. DNA quantification was performed as previously described in section 4.1.2. ALP-activity was measured using a commercially available kit (Kirkegaard & Perry, Guilford, UK), according to the manufacturer's instructions. Absorbance was measured at 620 nm and absorbance units (AU) were normalized to amount of DNA per sample, n=3.

Gene Expression Analysis.

After six days of stimulation in the monolayers, cells were washed three times with PBS followed by homogenisation in RLT buffer (Qiagen, Venlo, The Netherlands) supplemented with 3.5 µl β-Mercapto-EtOH and RNA extraction performed using the RNeasy kit (Qiagen, Venlo, Netherlands) according to the manufacturer's instructions. Complementary DNA (cDNA) was obtained by reverse transcription of 500 ng of total RNA with Oligo (dT)20 as primer (Superscript III; Invitrogen, Merelbeke, Belgium). Quantitative PCR was performed on a Rotor-Gene 6000 system (Corbett, Westburg, Leusden, The Netherlands) using a SybrGreen detection system. The two step reaction, 94° C. for 3 s and 60° C. for 40 s, was cycled 40 times and relative gene expression was calculated using the $2^{-\Delta CT}$ method.

BMP-Secretion by Differentiated Cells.

An ID1-reporter cell line, C2C12Bre was in vitro expanded to passage 5 and seeded in a 96 well plate at a cell density of 10 000 cells/cm$^2$ and left for cell attachment for 24 h. Thereafter, cells were washed three times in PBS followed by 16 h incubation in GM containing 0.10% FBS for cell synchronization. Next, cells were washed three times with PBS to remove serum remnants, thereafter, 100 µl conditioned media, collected at day 6 from the stimulated hPDCS, were applied in duplicates to the seeded C2C12Bre cells. Freshly made stimulation media was used as a baseline reference. After 14 h of stimulation, the C2C12Bre cells were washed three times with PBS and thereafter lysed for luciferase measurements with 45 µl of 1× cell lysis buffer (BD Pharmingen). 20 µl of the lysate was transferred in duplicates to a 96-well plate and assayed for luciferase activity using a LUMIstar Galaxy luminometer (BMG Labtechnologies). Luciferase activity was reported as relative luciferase units (RLU).

Development of a 2-Step Stimulation Regimen:

Pre-Conditioning Affects Cellular Phenotype.

Prior to BMP-stimulation, a pre-conditioning step was included where cells upon confluency were washed in PBS, synchronized for 16 h in GM containing 0.1% FBS. Next, cells were washed repeatedly in PBS to remove FBS remnants and pre-conditioned for 6 days in CDM or GM containing 10% FBS as control. After the 6 days, cellular phenotype was investigated by Fluorescence-activated cell sorting (FACS) and mRNA transcript analysis.

Facs Analysis.

Prior to the in vitro evaluation, flowcytometry was performed to characterize the expression of stemness markers on human periosteal cells by using human MSC Phenotyping kit (Lot #130-095-198, Miltenyi Biotec, NL). The extracellular staining was performed according to manufacturer's instruction. In brief, 100 µl of cell suspension (up to 1×10$^6$) were mixed with 10 µl of MSC Phenotyping Cocktail and incubated for 10 min in dark at 4° C. After staining, the cells were washed and analyzed using BD FACS Canto™ cell analyser (BD Biosciences, San Jose, Calif.) with FlowJo V10 software.

BMP-Stimulation of Pre-Conditioned Cells.

Following pre-conditioning in CDM or GM containing 10% BMP, cells were seeded and stimulated with 100 ng/ml BMP-2 (Medtronics, Minneapolis, Minn., U.S), BMP-4, BMP-6, BMP-7, BMP-9 or GDF5 (Peprotech, London, UK).

Immunohistochemistry.

BMP-2 stimulated cells were investigated by dual immunohistochemistry for Sox9 (Rabbit polyclonal, NovusBiologicals) and Osterix (Monoclonal Mouse IgG2B, R&D Systems). Primary antibodies with respective dilutions of 1:1000 and 1:200 were incubated overnight at 4° C. on plate rotator. Next, cells were incubated in secondary antibodies: Alexa 488 anti-mouse, (1:500) together with Biotinylated SP-conjugated goat anti rabbit 1:500 was incubated on plate rotator in dark for 90 min. After repeated washing, incubation with Streptavidin Alexa 555 (1:500) (Jackson ImmunoResearch) and DAPI (1:2500) for 90 minutes on plate rotator in dark. After repeated washing, samples were mounted in Mowiol for microscopic analysis by confocal imaging using Olympus FluoView FV1000 and visualized by Z-stacking 35 images of 26.22 micrometer.

In Vivo Implantation of Pre-Conditioned Cells.

Eight-week-old, female NMRI nu−/− mice were maintained in isolator cages in pathogen-free conditions. Preconditioned cells for 6 days followed by another 6 days of BMP-2 stimulation in 2D cultures were enzymatically released and incorporated in collagen type I hydrogel (5 mg/mL, BD Biosciences), with a cell density of 10 million cells per ml in 100 µl gels. Cells pre-conditioned in media containing 10% FBS followed stimulation with or without BMP-2 supplementation were used as controls, keeping the same cell density per ml. After gelation, the constructs were implanted subcutaneously into the back of anesthetized nude mice. Three weeks post implantation, the mice were sacrificed and the samples were excised. All samples were fixated using 4% paraformaldehyde for 1 hour at room temperature and processed for histologic and immunohistochemical evaluation. For each condition and time point four individual replicates were implanted and evaluated. All procedures on animal experiments were approved by the local ethical committee for Animal Research (KU Leuven). The animals were housed according to the guidelines of the Animalium Leuven (KU Leuven).

Evaluation of In Vivo Tissue Formation:

Histology.

All samples were fixated using 4% paraformaldehyde for 1 hour. All samples were dehydrated, embedded in paraffin, cut into 5 micrometer sections using a microtome (Microm HM360 Prosan) and stained for histology. To visualize glycosaminoglycans samples were stained with acidic Alcian Blue (pH=1, Merck) and counterstained with nuclear fast red (Vector Laboratories). General cell morphology was visualized using heamatoxyline (SigmaAldrich) and eosin staining (Klinipath). To visualize general tissue morphology, sections were stained with Masson's Trichrome (SigmaAldrich). Histological sections were microphotographed using (IX83P22F, Olympus).

Bioinspired Cell-Based 3D System.

3D Microwell Fabrication and Cell Aggregation.

A patterned silicon wafer was fabricated using standard soft lithographic techniques. In short, using a 25.000 DPI photoplot printer (Koenen, Germany) we fabricated a custom designed mask containing an array of 125.000 circles, each with a diameter of 200 micrometers and a minimal inter-circle space of 100 micrometers. This mask was used to photo-pattern SU-8 photoresist on top of a silicon wafer. The patterns structures had a controlled height of 50, 100 or 150 micrometers. Using replica molding, a master mold of micropatterned polydimethylsiloxane (Sylgard 184, Dow Corning) was fabricated. Using the mold, disks of 3% agarose microwell were fabricated for non-adherent cell culture. Inserts of 1.5 cm were punched out of the disks using a sterile biopsy puncher, placed in 24 well culture plates and sterilized using ultra violet light for 30 minutes. Scanning electron microscopy demonstrated the robustness and accuracy of the fabrication process. This method allows for high throughput production of microaggregates with controlled cell density per aggregate. The cells were detached using TripLE (Life Technologies), counted, washed and reseeded in a 24 well plate containing a microwell insert. By varying the thickness of the initial SU8 pattern, we could control the depth of agarose microwells. We demonstrated that low depth microwells (e.g. 66 micrometers) could form microaggregates but not retain them their original microwell, which could be achieved in higher depth microwell e.g. 150 micrometer. Microaggregates could be cultured up to at least 21 days in the microwells when thrice a week 1.5 ml of the medium was refreshed. To create aggregates composed of 50, 100 or 250 cells, the microwells were covered in 2 ml of serum free medium containing 100.000, 200.000 or 500.000 cells, respectively.

In vitro evaluation of micro aggregate size.

In vitro expanded cells were pre-conditioned as described hereabove and subsequently detached using TripLE (Life Technologies), counted, washed and reseeded in a 24 well plate containing a microwell insert. To create aggregates composed of 50, 100 or 250 cells, the microwells were covered in 2 ml of CDM containing 100.000, 200.000 or 500.000 cells, respectively. Microaggregates were cultured for 6 days with or without BMP-2 supplementation as described hereabove. 2D stimulated cells were used as control. Gene expression analysis, histology and IHC were performed as described hereabove.

In Vivo Implantation.

To evaluate the aggregates in vivo performance, identical procedure as described hereabove was performed. Aggregates were collected and encapsulated in a Collagen type 1 gel, 100 µl, 5 mg/ml, so in total $1*10^6$ cells/gel were implanted subcutaneous in NMRI$^{nu/nu}$ mice. 2D stimulated cells followed by 24 h aggregation without BMP-2 stimulation were included as controls. Subsequently, constructs were collected and implanted subcutaneously in the back at the cervical region of NMRI$^{nu/nu}$ mice. At three weeks post implantation, samples were harvested and analysed quantitatively by CT for in vivo bone formation and qualitatively by histology and immunohistochemistry. For orthotopic evaluation, CDM pre-conditioned hPDC were stimulated as aggregates in the presence of BMP-2 for 6 days. Subsequently after washing, the aggregates were collected and implants of 30 µl collagen type 1 gels (5 mg/mL, BD Biosciences) containing 1200 aggregates/gel were prepared. Subsequently, a critical size long bone defect was created in the right hind tibiae of NMRI$^{nu/nu}$ mice, allowing to examine the regenerative bone-forming potential of the in vitro prepared construct as previously described (Van Gastel, N et al., Stem cells 32, 2407-2418, 2014). In total, 6 constructs were implanted, 3 for week 8, 2 for week 4 and 1 for week 2. As control for the critical defect, 5 fractures were made where one was excluded from the study due to surgical error with remnants of bone spicules in the fracture. At harvest, samples were fixated using 2% paraformaldehyde for 12 h. Explants from the orthotopic model were analysed by ex vivo nano-CT as previously described (Bolander et al., European cells & materials 30,11-25, 2016) and samples were processed for IHC and histology. All procedures on animal experiments were approved by the local ethical committee for Animal Research (KU Leuven). The animals were housed according to the guidelines of the Animalium Leuven (KU Leuven).

Evaluation of In Vivo Performance:

Histological Analysis.

Histological analysis was performed as described hereabove. In addition, TRAP stain was performed to localize osteoclast activity. Sections were dewaxed and rehydrated through alcohols to PBS. Incubate sections in TRAP Buffer containing: 0.1 M Acetate buffer, 0.3M Sodium tartrate and 1% Triton X-100 for 20 min. The incubate sections in TRAP stain containing 0.5 ml/ml naphtol AS-MX phosphate and 1.1 mg/ml Fast red violet LB in TRAP buffer for 10 min at 37° C. Samples were counterstained in hematoxylin and mounted with aqueous mounting medium.

Immhunohistochemistry.

Detection of active BMP-signalling was done using immunohistochemistry with a rabbit Phospho-Smad1 (Ser463/465)/Smad5 (Ser463/465)/Smad9 (Ser465/467) (Cell signalling, Leiden, NL) according to the manufacturer's instructions and a peroxidase-conjugated goat anti-rabbit secondary antibody (Jackson Immunoresearch Laboratories, De Pinte, Belgium) diluted 1:2000 and 3,30-diaminobenzidine (Sigma) as a chromogenic substrate, Haematoxylin was used for counterstain.

Investigation of Endogenous BMP-2 Production.

Endogenous production of BMP-2 was analysed by a human BMP-2 ELISA development kit (Peprotech, London, U.K). Conditioned media from 6 days in vitro stimulated conditions, samples were then washed in non-supplemented CDM 3 times 1 hour, left over night and conditioned media were again collected, labelled day 7. Fresh stimulation media was used as baseline. For reading, media were diluted 1:500 since the kit is developed to detect 63-2000 µg/ml. The ELISA was performed according to the manufacturer's instructions.

Statistical Analysis.

Data are expressed as individual data points with average in bars. Statistical significance was determined using student T-test to compare between independent groups. Statistical significance is indicated on all graphs as follows: *:$p<0.05$, : $p<0.01$, *: $p<0.001$ (n=3).

2. Improved In Vivo Bone Forming Capacity of Serum Free In Vitro BMP-2-Primed Human Periosteum Derived Cells Seeded on a Ceramic Scaffold.

2.1 The Serum Level in Culture Medium Affected hPDC Proliferation In Vitro.

In search for a medium that maintains cell viability without inducing proliferation, hPDCs were cultured in media containing 0-10% FBS including one commercial serum free medium (SFM) and one in-house developed serum free chemically defined medium (CDM) as well as a standard osteogenic medium (OM) as control for the cell population. The DNA content was measured at different time points during culture and over a time span of 21 days. After 24 h and onwards, cells cultured in CDM or GM containing 0-, 0.5- or ~1% FBS, displayed a significant lower DNA content compared to cells cultured in 10% FBS, FIG. 1a. On day 3, a significantly higher DNA content was seen in cells cultured in SFM, as compared to standard basal serum free growth medium (GM). This phenomenon was further increased on day 6 and onwards. At this time point, the OM media had also displayed a significantly higher DNA content as compared to cells stimulated in standard GM. A live/dead staining after 3 days displayed a higher fraction of dead cells in GM containing 0.5- or 0% FBS. Cells cultured in CDM displayed a similar viability compared to cells cultured in 1% FBS. These observations were confirmed upon quantification, FIG. 1b. Since GM containing 1% FBS together with CDM do maintain cell viability without inducing proliferation, these were selected for further studies where GM containing 10% FBS was used as the standard control condition.

2.1.2 BMP-2-Stimulation Induced DNA Content and ALP-Activity.

After 6 days of stimulation in BMP-2-supplemented media, the culture displayed a homogenous population of polygonal cells with areas of mineralisation throughout the culture plate. In all BMP-2 supplemented conditions confluency was observed, indicating a proliferative effect by the addition of BMP-2. This was confirmed by an elevated DNA content measured in all media conditions supplemented with BMP-2, compared to non-supplemented conditions and to the positive control in OM, FIG. 1c. Furthermore, when investigating alkaline phosphatase (ALP)-activity, an in vitro marker for osteogenesis, BMP-2 stimulation induced a 4-fold elevation in all media conditions, FIG. 1d. This phenomenon was 2-fold higher in CDM as compared to serum containing conditions.

2.1.3 Serum Level Affected BMP-2 Induced Differentiation.

To investigate the effect of serum levels on BMP-2 induced differentiation, mRNA transcript analysis of transcriptional regulators and markers of chondrogenesis and osteogenesis was performed. The early chondrogenic marker sex determining region Y-box 9 (SOX9) displayed over a 2-fold elevated expression in all conditions stimulated with BMP-2, however, the CDM-condition displayed a 2.5-fold elevation as compared to BMP-2 stimulated cells under serum containing conditions, FIG. 1e. Similarly, the cartilage matrix marker Aggrecan (ACAN), displayed an increased expression in all BMP-2 stimulated cells and was over a 7-fold higher in CDM compared to serum conditions, FIG. 1e. In addition, the expression of both markers in the OM-condition was significantly lower. Interestingly, the early and mid-stage osteogenic markers Runt-related transcription factor 2 (RUNX2) and Osterix (OSX) displayed also a BMP-2 induced upregulation, FIG. 1f. Again, the expression was over a 4-fold higher in BMP-2 supplemented CDM, as compared to serum containing conditions. The increased differentiation profiles correlated with the upregulation of the transcriptional regulator Distal-less homeobox 5 (DLX5) in all conditions, a phenomenon that was a 5-fold higher in BMP-2 supplemented CDM, FIG. 1g. This trend was also observed for the downstream BMP-target gene inhibitor of differentiation 1 (ID1), FIG. 1g.

2.1.4 Endogenous BMP-Production by Stimulated hPDCs.

Figure 1H:
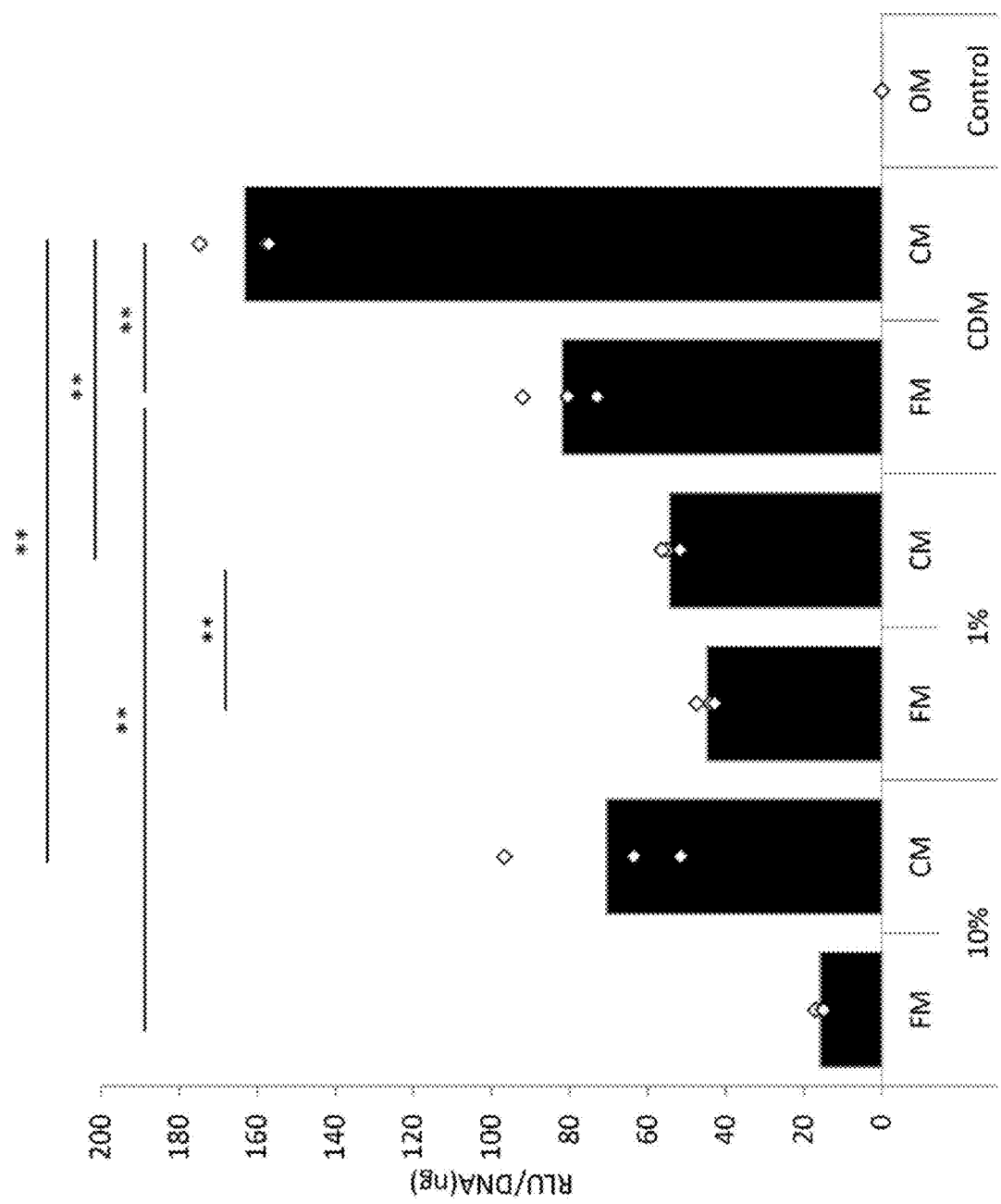

To confirm that the changes in gene expression translated into changes at the protein level, BMP-secretion by BMP-2 stimulated hPDCs was measured by a Luciferase signal activated upon ID1 expression in an ID1 reporter cell line, FIG. 1h. Conditioned media (CM) from hPDCs stimulated in CDM supplemented with BMP-2 induced a 1.2-fold elevated signal as compared to fresh stimulation media (FM) and CM from hPDCs stimulated in the presence of FBS. There was no difference in signal between CM and FM collected from hPDCs stimulated in 10% FBS media and a 1.2-fold lower signal was seen in CM from cells stimulated in the 1% FBS condition, as compared to FM.

2.2 Enhanced In Vitro Differentiation Resulted in Elevated In Vivo Bone Formation.

To evaluate the increased effect seen in BMP-stimulation of hPDCs under serum free conditions in an in vitro and an in vivo setting, stimulated cells were seeded onto a CaP-carrier with no bone forming capacity when seeded with non-stimulated hPDCs. Subsequently, constructs were implanted in an ectopic NMRInu/nu mouse model for 2, 4 and 6 weeks. Analysis of 3D reconstructed nano-CT scans displayed various tissue formation profiles by the different constructs in 4 week explants, FIG. 15a. In control explants, only remnants of CaP-grains from the scaffold can be seen. These were also seen in constructs containing BMP-2 stimulated cells, where additional zones of mineralized tissues were detected, even to a larger extent in cells stimulated under serum free conditions. Since higher and more homogenous de novo bone formation was seen in constructs containing hPDCs cultured in BMP-2 supplemented CDM, these constructs were also evaluated at 2 weeks displaying the onset of mineralization, FIG. 15b. This mineralized tissue seen at 2 and 4 weeks further matured based on morphology and density after 6 weeks, FIG. 15c. Upon quantification, a 10-fold higher amount of mineralized matrix was observed at 4 weeks in constructs seeded with hPDC stimulated with BMP-2 under serum free conditions, FIG. 15d. The amount of mineralized matrix was a 1.5-fold higher at 4 weeks as compared to 2 weeks, FIG. 15d.

2.3 Serum Free BMP-2 Stimulation Induced hPDC-Mediated Endochondral Bone Formation.

Qualitative tissue analysis was carried out by histology and IHC. At 4 weeks, de novo bone tissue was found in sections containing BMP-2 stimulated cells, depicted by H&E staining and confirming the earlier described nano-CT data. Active remodelling was suggested by areas positive for TRAP staining in the BMP-2 stimulated constructs. In BMP-2 supplemented CDM conditions, areas of different maturity were confirmed by a Masson's Trichrome (MT) staining, as reflected by intensity in blue for different densities and red stain for immature bone tissue. Moreover, this staining displayed bone marrow infiltration in the zones of early mineralized tissue and the IHC staining for human OCN (hOCN) confirmed the contribution of implanted cells. In week 2 explants of cells stimulated in BMP-2 supplemented CDM, Safranin and Toluidine blue confirmed the presence of remaining cartilaginous tissues indicated by light red and purple stain, respectively. Active tissue remodelling was shown by a TRAP staining, suggesting the remaining cartilage tissue being remodeled into bone. Contribution to de novo formed bone by the implanted cells was confirmed by IHC for hOCN. As indicated by the nano-CT-analysis, explants from 6 weeks displayed a mature mineralized tissue. This was confirmed by the H&E staining and the MT-staining. After 6 weeks of implantation, TRAP-positivity was mainly observed in areas lining the bone tissue which stained positive for human OCN.

Discussion

Limited treatment alternatives are available for organs or tissues lacking adequate biological conditions to self-regenerate. As of yet, the success of cell-based Advanced Therapy Medicinal Products (ATMPs) has been hampered partially due to a non-reliable biological potency of the implant. Possibly, this could be due to the design, since, in terms of cell-based treatment of critical bone fractures, the standard cell source today is bone marrow derived mesenchymal stem cells (BMSC). However, bone marrow injuries exclusively heal by intramembranous ossification, and BMSCs do not give rise to chondrocytes in the fracture callus. Since long bone fractures heal through a cartilage intermediate, periosteum derived cells, the major contributing cell source to the cartilaginous callus, may be a more clinically relevant cell source [6]. Another reason for the unpredictable implant behaviour may be poorly defined culture media compositions. Consequently, we defined a serum free chemically defined medium (CDM), relevant for clinical translation and able to maintain hPDC viability. Upon supplementation with BMP-2, CDM-stimulated hPDCs displayed a powerful enhanced osteochondrogenic differentiation profile in vitro. In addition, analysis of conditioned media suggested secretion of BMPs by the stimulated cells. This finding may be of relevance for the in vivo setting, since endogenous BMP-secretion attracts and stimulates host cells in the fracture environment to contribute to fracture healing. Encouragingly, when seeding the in vitro monolayer-stimulated cells onto CaP-scaffolds followed by in vivo transplantation, a process resembling endochondral bone formation was seen. This is in line with previous findings where BMP-ligands were coated onto CaP-scaffolds with different Ca2+-release kinetics. The synergistic effect of BMP-2 or BMP-6 stimulation with high Ca2+-release from the biomaterial led to ossicle formation. However, coating of biomaterials with recombinant growth factors and implanting the coated construct in vivo, remains a challenge for clinical translation mostly due to the high supraphysiological concentrations of growth factors needed. In the current invention, these hurdles are overcome by limiting the use of recombinant proteins to the in vitro priming of the cells. For the healing of a complex bone fracture, a construct that is able to induce bone tissue formation via a cartilage intermediate which is subsequently remodeled into bone and which did not depend on the addition of exogenous growth factors is attractive, since this mimics natural fracture healing. These findings are therefore of relevance in the development of clinical cell-based constructs for bone tissue regeneration specifically and in general for regenerative medicine.

Materials and Methods

Cell Culture, Proliferation and Viability.

The isolation and in vitro expansion of human periosteum derived cells (hPDCs) to passage 5 was performed in growth medium (GM) according to previously described protocols (De Bari et al., Arthritis Rheum 54, 1209-1221, 2006). For the cell proliferation experiments, cells were seeded in a density of 5 000 cells/cm$^2$ and cultured in modified GM containing 10-, 5-, 2-, 1-, 0.5- or 0% foetal bovine serum (FBS) or in 2 distinct serum free media for 6 days. One was a commercially available (Lonza, Verviers, BE) and one was a modified in-house developed medium (patent US20010039050), where the growth factor cocktail, β-Glycerophosphate and lineolic acid were removed. As control, standard osteogenic medium (OM) (GM with 10% FBS supplemented with 100 nM dexamethasone, 10 mM β-Glycerophosphate and 50 mM ascorbic acid 2-sulfate (Sigma-Aldrich, Diegem, BE)) were included. After 6 days culture, cell viability was evaluated with a live/dead assay (Invitrogen, Merelbeke, BE). The ethical committee for Human Medical Research (KU Leuven) approved all procedures, and the patient informed consents were obtained.

In Vitro BMP-Stimulation.

For BMP-2 stimulation, hPDCs were seeded at a cell seeding density of 10 000 cells/cm$^2$ and stimulated with BMP-2 (100 ng/ml, Medtronics, Minneapolis, US) supplemented media (1% or 10% FBS or the serum free CDM) (n=3) 6 days. At the end of the culture, samples were collected for DNA, Alkaline phosphatase (ALP)-activity and gene expression analysis. As a positive control, cells were cultured in OM.

DNA and ALP-Activity Analysis.

To evaluate the DNA content and the ALP activity of the cells, the monolayers were lysed in 0.05% TritonX-100 (Thermo Scientific, Doornveld, BE). The DNA content was measured in duplicates using the Quant-i™ PicoGreen® dsDNA assay (Invitrogen, Merelbeke, BE) (n=3) according to the manufacturer's instructions. The ALP-activity was measured in duplicates using a commercially available kit (Kirkegaard & Perry, Guilford, UK), according to the manufacturer's instructions. The absorbance was measured at 260 nm and absorbance units (AU) were normalized to the amount of DNA per sample, n=3.

Gene Expression Analysis.

Monolayers were washed followed by RNA isolation, complementary cDNA synthesis and quantitative PCR, performed as previously described (Bolander et al., European cells & materials 30, 11-25, 2016), with primer sequences as listed in table 1.

BMP-Secretion by Differentiated Cells.

In order to estimate the secretion of active BMPs by the stimulated cells, an ID1-reporter cell line, C2C12Bre, was seeded at a cell density of 10 000 cells/cm$^2$ and stimulated in 100 µl conditioned media collected at day 6 from the stimulated hPDCS. Fresh stimulation media was used as a base-line reference. After 14 h, the C2C12Bre cells were washed and lysed for luciferase measurements with 45 µl of 1× cell lysis buffer (BD Pharmingen, Erembodegem, BE). 20 µl of the lysate was transferred in duplicates to a 96-well plate and assayed for luciferase activity using a LUMIstar Galaxy luminometer (BMG Labtechnologies, Temse, BE). The luciferase activity was reported as relative luciferase units (RLU).

Construct Preparation and In Vivo Implantation.

A clinical grade CaP-based material, Copios® (Zimmer, Wemmel, BE), was selected as the CaP-scaffold based on previous work and punched out to cylinders of 35 mm$^3$ (Bolander et al., European cells & materials 30,11-25, 2016). Monolayer cultures of hPDCs stimulated with BMP-2 supplemented CDM or GM containing 10% FBS were washed and trypsin-released (1 mM EDTA; Invitrogen). Scaffolds were drop-seeded with 50×10$^3$ hPDCs/mm$^3$ and constructs were incubated for 24 hours at 37° C. and 5% CO$_2$ to allow cell attachment. Thereafter, the cell-seeded constructs were implanted subcutaneously in the cervical region of NMRI$^{nu/nu}$ mice (Janvier, Genest Saint Isle, FR). For in vivo bone formation, explants were harvested 2, 4 or 6 weeks post implantation, fixed in 4% paraformaldehyde and stored in PBS until further analysis. For the week 6 samples, only one construct could be retrieved, thus only used for qualitative assessment of tissue maturation. 3D quantification by nanofocused computed tomography (nano-CT) and processing for qualitative analysis was performed as previously described (Bolander et al., European cells & materials 30,11-25, 2016). All animal procedures were approved by the local ethical committee for Animal Research (KU Leuven). The animals were housed according to the guidelines of the Animalium Leuven (KU Leuven).

Qualitative Evaluation of In Vivo Formed Tissue.

Qualitative assessment of in vivo skeletal tissue formation was performed as previously described (Bolander et al., European cells & materials 30,11-25, 2016), with following modifications: the presence of cartilaginous matrix was investigated by SafraninO and Toluidine blue staining. Deparaffinised sections were either immersed in 0.25% SafraninO or 1% Toluidine blue (Merck, Damstadt, DE), followed by a rinsing step in acetic acid or isopropanol, respectively. The sections were then counterstained in fast green, washed, dehydrated and cleared in xylene and mounted in PerTex. To analyse the maturity of the formed bone, a Masson's Trichrome staining was performed using a commercial kit according to the manufacturer's instructions (Sigma-Aldrich).

Statistical Analysis.

Data are expressed as individual data points with bars representing the average value. Statistical significance was determined using a non-paired unequal variance student t-test to compare between independent groups. Statistical significance is indicated on all graphs as follows: *:$p<0.05$, : $p<0.01$, *: $p<0.001$, n=3 if nothing else stated.

The invention claimed is:

1. A method for producing a cellular composition with in vivo bone forming potential, the method comprising the steps of:
   a. culturing periosteum derived mesenchymal stem cells in a serum-free medium, the serum-free medium being without a BMP (Bone Morphogenetic Protein) in that the serum-free medium does not contain an exogenous added BMP;
   b. culturing the periosteum derived mesenchymal stem cells obtained after step (a) in a serum-free medium in the presence of a BMP, thereby differentiating the periosteum derived mesenchymal stem cells into cells with an osteochondrogenic phenotype; and
   c. seeding and/or encapsulating the cells with an osteochondrogenic phenotype obtained after step (b) on or into a biocompatible carrier, wherein the serum-free medium in step (a) and step (b) each comprise two basal cell culture media in a ratio of about 1:1 (v/v), and comprise insulin, transferrin, selenium, α-ketoglutarate, ceruloplasmin, cholesterol, phosphatidyl ethanolamine, α-tochoferol acid succinate, reduced glutathione, taurine, and L-ascorbic acid 2-sulphate.

2. The method according to claim 1, wherein step (b) is performed under conditions allowing the aggregation of cells.

3. The method according to claim 1, wherein said biocompatible carrier comprises natural or biomimetic collagen, calcium phosphate, carboxy methyl cellulose or combinations thereof.

4. The method according to claim 1, wherein said biocompatible carrier is a calcium phosphate scaffold comprising one or more of: a sterile, biocompatible porous bone mineral substitute, a synthetic bone graft substitute including calcium phosphate, dibasic and purified Type I bovine collagen, a natural porous bone mineral matrix for use as a dental bone substitute, or a synthetic, radiopaque, resorbable, and osteoconductive β-tricalcium phosphate bone void filler.

5. The method according to claim 1, wherein step (a) and step (b) are performed for at least 24 hours.

6. The method according to claim 1, wherein step (a) is performed for about 3 to about 6 days, and step (b) is performed for between 1 to about 28 days.

7. The method according to claim 1, wherein step (a) is performed for about 6 days and step (b) is performed for 1 to about 28 days.

8. The method according to claim 1, wherein said BMP includes BMP2, BMP4, BMP6, BMP7, BMP9, GDF5, and TGFβ, or a combination thereof.

9. The method according to claim 1, wherein said BMP is BMP2, BMP6, or a combination of BMP-2 and BMP-6.

10. The method according to claim 1, wherein the periosteum derived mesenchymal stem cells are cultured in the presence of said BMP in a concentration of about 2 to 2000 ng/ml within the serum-free medium.

11. The method according to claim 1, wherein the periosteum derived mesenchymal stem cells are cultured in the presence of said BMP in a concentration of about 100 ng/ml within the serum-free medium.

12. The method according to claim 1, wherein the serum-free medium in step (a) and step (b) each further comprise one or more of ceruloplasmin, triiodothyronine, hydrocortisone, and parathyroid hormone.

13. The method according to claim 1, wherein the osteochondrogenic phenotype is defined by expression of the chondrogenic marker SOX9 and the osteogenic marker Osterix.

14. A method for producing a cellular composition with in vivo bone forming potential, the method comprising the steps of:
   a. culturing periosteum derived mesenchymal stem cells in a serum-free medium, the serum-free medium being without a BMP (Bone Morphogenetic Protein) in that the serum-free medium does not contain an exogenous added BMP;
   b. culturing the periosteum derived mesenchymal stem cells obtained after step (a) in a serum-free medium in the presence of a BMP, thereby differentiating the periosteum derived mesenchymal stem cells into cells with an osteochondrogenic phenotype; and
   c. seeding and/or encapsulating the cells with an osteochondrogenic phenotype obtained after step (b) on or into a biocompatible carrier.

15. The method according to claim 14, wherein said biocompatible carrier comprises natural or biomimetic collagen, calcium phosphate, carboxy methyl cellulose or combinations thereof.

16. The method according to claim 14, wherein said biocompatible carrier is a calcium phosphate scaffold comprising one or more of: a sterile, biocompatible porous bone mineral substitute, a synthetic bone graft substitute including calcium phosphate, dibasic and purified Type I bovine collagen, a natural porous bone mineral matrix for use as a dental bone substitute, or a synthetic, radiopaque, resorbable, and osteoconductive β-tricalcium phosphate bone void filler.

17. The method according to claim 14, wherein said BMP is BMP2, BMP4, BMP6, BMP7, BMP9, GDF5, and TGFβ, or a combination thereof.

18. The method according to claim 14, wherein the periosteum derived mesenchymal stem cells are cultured in the presence of said BMP in a concentration of about 2 to 2000 ng/ml within the serum-free medium.

19. The method according to claim 14, wherein the serum-free medium in step (a) and step (b) each further comprise one or more of ceruloplasmin, triiodothyronine, hydrocortisone, and parathyroid hormone.

20. The method according to claim 14, wherein the osteochondrogenic phenotype is defined by expression of the chondrogenic marker SOX9 and the osteogenic marker Osterix.

* * * * *